(12) United States Patent
Divita et al.

(10) Patent No.: US 11,713,336 B2
(45) Date of Patent: *Aug. 1, 2023

(54) PEPTIDES AND NANOPARTICLES FOR INTRACELLULAR DELIVERY OF MOLECULES

(71) Applicant: AADIGEN, LLC, Pacific Palisades, CA (US)

(72) Inventors: Gilles Divita, St André de Sangonis (FR); Neil Desai, Pacific Palisades, CA (US)

(73) Assignee: Aadigen, LLC, Pacific Palisades, CA (US)

( * ) Notice: Subject to any disclaimer, the term of this patent is extended or adjusted under 35 U.S.C. 154(b) by 187 days.

This patent is subject to a terminal disclaimer.

(21) Appl. No.: 16/930,091

(22) Filed: Jul. 15, 2020

(65) Prior Publication Data

US 2021/0032290 A1 Feb. 4, 2021

Related U.S. Application Data

(63) Continuation of application No. 15/539,619, filed as application No. PCT/EP2015/081197 on Dec. 23, 2015, now Pat. No. 10,745,440.

(30) Foreign Application Priority Data

Dec. 24, 2014 (FR) ..................... 1403004

(51) Int. Cl.
| | |
|---|---|
| *C07K 7/08* | (2006.01) |
| *C12N 15/87* | (2006.01) |
| *A61K 47/69* | (2017.01) |
| *A61K 47/64* | (2017.01) |
| *A61K 31/713* | (2006.01) |
| *C12N 15/113* | (2010.01) |
| *A61K 38/00* | (2006.01) |

(52) U.S. Cl.
CPC .............. *C07K 7/08* (2013.01); *A61K 31/713* (2013.01); *A61K 47/64* (2017.08); *A61K 47/6929* (2017.08); *C12N 15/113* (2013.01); *C12N 15/1137* (2013.01); *C12N 15/87* (2013.01); *A61K 38/00* (2013.01); *C12N 2310/14* (2013.01); *C12N 2310/141* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | |
|---|---|---|
| 7,514,530 B2 | 4/2009 | Divita |
| 8,822,647 B2 | 9/2014 | Jensen |
| 9,376,468 B2 | 6/2016 | Divita |
| 9,579,395 B2 | 2/2017 | Divita |
| 9,598,465 B2 | 3/2017 | Divita |
| 9,834,581 B2 | 12/2017 | Divita |
| 10,111,965 B2 | 10/2018 | Divita |
| 10,118,944 B2 | 11/2018 | Divita |
| 10,189,876 B2 | 1/2019 | Divita |
| 10,745,440 B2 | 8/2020 | Divita |
| 2009/0281041 A1 | 11/2009 | Debnath |
| 2010/0099626 A2 | 4/2010 | Divita |
| 2015/0051266 A1 | 2/2015 | Kochenderfer |
| 2015/0080320 A1 | 3/2015 | Desai |
| 2017/0081661 A1 | 3/2017 | Divita |
| 2019/0002499 A1 | 1/2019 | Divita |
| 2019/0046652 A1 | 2/2019 | Divita |
| 2019/0077833 A1 | 3/2019 | Divita |

FOREIGN PATENT DOCUMENTS

| | | |
|---|---|---|
| CN | 104080480 A | 10/2014 |
| EP | 1795539 A1 | 6/2007 |
| WO | 2007000584 A1 | 1/2007 |
| WO | 2007069090 A2 | 6/2007 |
| WO | 2007069090 A3 | 2/2008 |
| WO | 2008036929 A2 | 3/2008 |
| WO | 2008036929 A3 | 11/2008 |
| WO | 2012137150 A2 | 10/2012 |
| WO | 2012137150 A3 | 12/2012 |
| WO | 2013150338 A1 | 10/2013 |
| WO | 2013173307 A1 | 11/2013 |
| WO | 2014053622 A1 | 4/2014 |
| WO | 2014053624 A1 | 4/2014 |
| WO | 2014053629 A1 | 4/2014 |
| WO | 2014053880 A1 | 4/2014 |
| WO | 2014099671 A1 | 6/2014 |
| WO | 2014127261 A1 | 8/2014 |

OTHER PUBLICATIONS

Terashima et al. (Journal of Agricultural and Food Chemistry; 2011,59,11234-11237).*
Akinc, A. et al. (May 11, 2010). "Development of Lipidoid-siRNA Formulations For Systemic Delivery To The Liver," Mol. Ther. 17(5):872-879.
Barre-Sinoussi, F. et al. (May 20, 1983) "Isolation of a T-Lymphotropic Retrovirus from a Patient at Risk for Acquired Immune Deficiency Syndrome (AIDS)," Science 220(4599):868-871.
Batzer, M.A. et al. (Sep. 25, 1991). "Enhanced Evolutionary PCR Using Oligonucleotides With Inosine At The 3'-Terminus," Nucleic Acid Res. 19(18):5081.
Brooks, P.C.et al., (Apr. 22, 1994) "Requirement of Vascular Intergrin αvβ3 for Angiogenesis," Science 264:569-571.
Burshell, J. et al., (Oct. 15, 1987) "Development and Characterization of Breast Cancer Reactive Monoclonal Antibodies Directed to the Core Protein of the Human Milk Mucin," Cancer Res. 47:5476-5482.

(Continued)

*Primary Examiner* — Julie Ha
*Assistant Examiner* — Tara L Martinez
(74) *Attorney, Agent, or Firm* — Morrison & Foerster LLP

(57) ABSTRACT

The present invention pertains to peptides and peptide-containing complexes/nanoparticles that are useful for stabilizing and delivering cargo molecules such as nucleic acids.

25 Claims, 18 Drawing Sheets

Specification includes a Sequence Listing.

(56) References Cited

OTHER PUBLICATIONS

Calegari, F. et al., (Oct. 29, 2002) "Tissue-Specific RNA Interference in Postimplantation Mouse Embryos with Endoribonuclease-Prepared Short Interfering RNA," Proc. Natl. Acad. Sci. USA 99:14236-14240.
Crombez, L. et al. (2009, e-pub. May 29, 2009). "Targeting Cyclin B1 Through Peptide-Based Delivery of siRNA Prevents Tumor Growth," Nucleic Acid Research 37(14):4559-4569.
Crombez, L. et al. (Jan. 2009). "A New Potent Secondary Amphipathic Cell-Penetrating Peptide for siRNA Delivery Into Mammalian Cells," Mol. Ther. 17(1):95-103.
Crowet, JM.et al. (Feb. 2013, e-pub. Sep. 19, 2012). "Modeling of Non-Covalent Complexes of the Cell-penetrating Peptide CADY and its siRNA Cargo," BBA 1828(2):499-509.
Deshayes, S. et al. (2005; e-pub. Jun. 17, 2005). "Cell-penetrating Peptides: Tools for Intracellular Delivery of Therapeutics," Cell Mol Life Sci. 62:1839-1849.
Deshayes, S. et al. (2008, e-pub. Oct. 25, 2007). "Delivery of Proteins and Nucleic Acids Using a Non-Covalent Peptide-Based Strategy," Adv. Drug Deliv. Rev. 60:537-547.
Dokurno, P. et al., (1998) "Crystal Structure at 1.95 A Resolution of the Breast Tumour-specific Antibody SM3 Complexed with its Peptide Epitope Reveals Novel Hypervariable Loop Recognition," J. Mol. Biol. 284:713-728.
European Notice of Allowance (Decision to Grant) dated Apr. 4, 2019 for EP Application No. 15825938.2 filed Jun. 20, 2017, two pages.
European Notice of Allowance (Intention to Grant) dated Nov. 14, 2018 for EP Application No. 15825938.2 filed Jun. 20, 2017, five pages.
European Notice of Allowance (Intention to Grant) dated Sep. 19, 2018 for EP Application No. 15825938.2 filed Jun. 20, 2017, five pages.
Futreal, A.P. et al. (Oct. 7, 1994) "BRCA1 Mutations in Primary Breast and Ovarian Carcinomas" Science 226:120-122.
Girling, A. et al., (1989). "A Core Protein Epitope of the Polymorphic Epithelial Mucin Detected by the Monoclonal Antibody SM-3 os Selectivly Exposed in a Range of Primary Carcinomas," Int. J. Cancer 43:1072-1076.
Glover, D.J. et al. (Apr. 2005, e-pub. Mar. 10, 2005). "Towards Safe, Non-Viral Therapeutic Gene Expression in Humans," Nat. Rev. Genet. 6:299-310.
Gondeau, C. et al. (Apr. 8, 2005, e-pub. Jan. 11, 2005). "Design of a Novel Class of Peptide Inhibitors of Cyclin-Dependent Kinase/Cyclin Activation," J.Biol Chem. 280(14):13793-13800.
Gump, J.M. et al. (Oct. 2007). "TAT Transduction: The Molecular Mechanism and Therapeutic Prospects," Trends .Mol Med 13(10):443-448.
Hanahan, D. (1997). "Signaling Vascular Morphogenesis and Maintenance," Science 277:48-50.
Hareuveni, M. et al., (1990). "A Transcribed Gene, Containing a Variable Number of Tandem Repeats, Codes for a Human Epithelial Tumor Antigen," Eur. J. Biochem 189:475-486.
Harris, J.D. et al., (1994). Gene Therapy for Cancer Using Tumour-Specific Prodrug Activation, Gene Therapy 1:170-175.
He, L. et al. (Jun. 28, 2007). "A MicroRNA Component of the p53 Tumour Suppressor Network," Nature 447 (7148):1130-1134, 15 pages.
Heitz, F. et al. (2009). "Themed Section: Vector Design and Drug Delivery Review. Twenty Years of Cell-Penetrating Peptides: From Molecular Mechanisms to Therapeutics," British Journal of Pharmacology 157:195-206.
Ibraheem, D. et al. (Jan. 1, 2014; e-pub. Nov. 25, 2013). "Gene Therapy and DNA Delivery Systems," Int J Pharm 459(1-2):70-83.
International Preliminary Report on Patentability dated Jul. 6, 2017 for PCT Application No. PCT/EP2015/081197 filed on Dec. 23, 2015, six pages.
International Search Report dated Apr. 12, 2016 for PCT Application No. PCT/EP2015/081197 filed on Dec. 23, 2015, four pages.
Ji, Q. et al. (Aug. 28, 2009). MicroRNA miR-34 Inhibits Human Pancreatic Cancer Tumor-Initiating Cells, PloS One 4(8):e6816, pp. 1-13.
Kanai, F. et al., (Feb. 1, 1997). "In Vivo Gene Therapy for Alpha-Fetoprotein_Producing Hepatocellular Carcinoma by Adenovirus-Mediated Transfer of Cytosine Deaminase Gene," Cancer Res. 57:461-465.
Kawasaki, H. et al. (2003). "siRNAs generated by recombinant human Dicer induce specific and significant but target site-independent gene silencing in human cells," Nucleic Acids Res. 31(3):981-987.
Kim, Y-W. et al. (2011, e-pub. May 12, 2011). "Synthesis of All-Hydrocarbon Stapled α-Helical Peptides by Ring-Closing Olefin Methathesis," Nature Protocols 6(6):761-771.
Knight, S.W. et al. (Sep. 21, 2001). "A Role for the Rnase III Enzyme DCR-1 in RNA Interference and Germ Line Development in Caenorhabditis elegans," Science 293:2269-2271.
Konate, K. et al. (Apr. 27, 2010). "Insight into the Cellular Uptake Mechanism of a Secondary Amphipathic Cell-Penetrating Peptide for siRNA Delivery," Biochemistry 49(16):3393-3402.
Kurzawa, L. et al. (2010, e-pub. Feb. 25, 2010). "PEP and CADY-Mediated 1-23 Delivery of Fluorescent Peptides and Proteins Into Living Cells," Biochimica Et Biophysica Acta 1798(12):2274-2285.
Mery, J. et al. (Jul./Aug. 1992). "Disulfide Bond as Peptide-Resin Linkage in Boc-Bzl SPPS, for Potential Biochemical Applications," Peptide Research 5(4):233-240.
Michael, S.I. et al. (1995). "Addition of a Short Peptide Ligand to the Adenovirus Fiber Protein," Gene Therapy 2:660-668.
Mickan, A. et al. (2014). "Rational Design of CPP-based Drug Delivery Systems: Considerations from Pharmacokinetics," Current Pharmaceutical Biotechnology 15(3):200-209.
Miki, Y. et al. (Oct. 7, 1994). "A Strong Candidate for the Breast and Ovarian Cancer Susceptibility Gene BRCA1," Science 226:66-71.
Morris, M.C. et al. (1997). "A New Peptide Vector for Efficient Delivery of Oligonucleotides Into Mammalian Cells," Nucleic Acids Res. 25(14):2730-2736.
Morris, M.C. et al. (2007, e-pub. Mar. 5, 2007) "A Non-Covalent Peptide-Based Carrier for in vivo Delivery of DNA Mimics," Nucleic Acids Research 35(7):e49, 10 pages.
Morris, M.C. et al. (Dec. 2001). "A Peptide Carrier for the Delivery of Biologically Active Proteins Into Mammalian Cells," Nat. Biotechnol. 19:1173-1176.
Nakase, I. et al. (Dec. 2004). "Cellular Uptake of Arginine-Rich Peptides: Roles for Macropinocytosis and Actin Rearrangement," Molecular Therapy 10(6):1011-1022.
Ohtsuka, E. et al. (Mar. 10, 1985). "An Alternative Approach to Deoxyoligonucleotides as Hybridization Probes by Insertion of Deoxyinosine at Ambiguous Codon Positions," J. Biol. Chem. 260(5):2605-2608.
Polakis, P. (1995) "Mutations In The APC Gene and Their Implications for Protein Structure And Function," Curr. Opin. Genet. Dev. 5:66-71.
Robertson, H.G. et al. (Jan. 10, 1968). "Purification and Properties of Ribnuclease III from *Escherichia coli*," J. Biol. Chem. 243:82-91.
Roisin, A. et al. (Mar. 5, 2004—e-pub. Dec. 10, 2003) "Inhibition of HIV-1 Replication by Cell-penetrating Peptides Binding Rev." J. Biol. Chem. 279(10):9208-9214.
Rome, C. et al. (2013). "Near-Infrared Optical Imaging of Nucleic Acid Nanocarriers In Vivo," Methods Mol. Biol. 948:49-65.
Rothbard, J.B. et al. (2004; e-pub. Jul. 20, 2004). "Role of Membrane Potential and Hydrogen Bonding in the Mechanism of Translocation of Guanidinium-Rich Peptides into Cells," Journal of American Chemical Society 126 (31):9506-9507.
Schrewe, H. et al. (Jun. 1990). "Cloning of the Complete Gene for Carcinoembryonic Antigen: Analysis of Its Promoter Indicates a Region Conveying Cell Type-Specific Expression," Mol. Cell. Biol. 10(6):2738-2748.
Shukla, R.S. et al. (2014; Aug. 26, 2014). "Peptides Used in the Delivery of Small Noncoding RNA," Molecular Pharmaceuticals 11(10):3395-3408.

(56) References Cited

OTHER PUBLICATIONS

Stamey, T.A. et al., (Oct. 8, 1987). "Prostate-Specific Antigen As A Serum Marker For Adenocarcinoma Of The Prostate," New England J. Med. 317, 909-916.

Thomas, A. et al. (2006, e-pub. Oct. 3, 2006). "Prediction of Peptide Structure: How Far are We?" Proteins 65:889-897.

Vile, R.G. et al. (Sep. 1, 1993). "Use of Tissue-Specific Expression of the Herpes Simplex Virus Thrymidine Kinase Gene to Inhibit Growth of Established Murine Melanomas Following Direct Intratumoral Injection of DNA," Cancer Res. 53:3860-3864.

Wooster, R. et al. (Dec. 21-28, 1995). "Identification of the Breast Cancer Susceptibility Gene BRCA2," Nature 378:789-792.

Written Opinion of the International Searching Authority dated Apr. 12, 2016 for PCT Application No. PCT/EP2015/081197 filed on Dec. 23, 2015, four pages.

Yang, D. et al. (Jul. 23, 2002, e-pub. Jul. 2, 2002). "Short RNA Duplexes Produced By Hydrolysis With *Escherichia coli* RNase III Mediate Effective RNA Interference In Mammalian Cells," PNAS USA 99:9942-9947.

Yin, H. et al. (Aug. 2014). "Non-Viral Vectors for Gene-Based Therapy," Nature Reviews Genetics 15:541-555.

Zhou, Z. et al. (Dec. 2010). "Research Advanced on Cell Penetrating Peptides in Cancer Therapy," 18 (12):2479-2500. (Translation of the Abstract Only).

\* cited by examiner

SEQUENCE LISTING

```
<160> NUMBER OF SEQ ID NOS: 41

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Any Amino Acid, and may be present or
      absent
<220> FEATURE:
<221> NAME/KEY: VARIANT
<222> LOCATION: 6, 7, 8, 15, 16, 17, 18
<223> OTHER INFORMATION: Xaa = Any Amino Acid

<400> SEQUENCE: 1

Xaa Lys Trp Arg Ser Xaa Xaa Xaa Arg Trp Arg Leu Trp Arg Xaa Xaa
1               5                   10                  15

Xaa Xaa Ser Arg
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic Construct

<400> SEQUENCE: 2

Lys Trp Arg Ser Ala Gly Trp Arg Trp Arg Leu Trp Arg Val Arg Ser
1               5                   10                  15

Trp Ser Arg

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Lys Trp Arg Ser Ala Leu Tyr Arg Trp Arg Leu Trp Arg Ser Arg Ser
1               5                   10                  15

Trp Ser Arg
```

<210> SEQ ID NO 4
<211> LENGTH: 19
<212> TYPE: PRT
<213> ORGANISM: Artificial Sequence
<220> FEATURE:
<223> OTHER INFORMATION: Synthetic Construct

<400> SEQUENCE: 4

Lys Trp Arg Ser Ala Leu Tyr Arg Trp Arg Leu Trp Arg Ser Ala Leu
1               5                   10                  15

Tyr Ser Arg

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = beta Ala or Ser, and may be present or
      absent

<400> SEQUENCE: 5

Xaa Lys Trp Arg Ser Ala Gly Trp Arg Trp Arg Leu Trp Arg Val Arg
1               5                   10                  15

Ser Trp Ser Arg
            20

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Val or Ser
<220> FEATURE:
<221> NAME/KEY: VARIANT
<222> LOCATION: 8
<223> OTHER INFORMATION: Xaa = Arg, Val, or Ala
<220> FEATURE:
<221> NAME/KEY: VARIANT
<222> LOCATION: 9
<223> OTHER INFORMATION: Xaa = Ser or Leu
<220> FEATURE:
<221> NAME/KEY: VARIANT
<222> LOCATION: 10
<223> OTHER INFORMATION: Xaa = Trp or Tyr

<400> SEQUENCE: 6

Arg Trp Arg Leu Trp Arg Xaa Xaa Xaa Xaa Ser Arg
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4,8
<223> OTHER INFORMATION: linked by the hydrocarbon linkage

<400> SEQUENCE: 7

```
Lys Trp Arg Ser Ala Gly Trp Arg Trp Arg Leu Trp Arg Val Arg Ser
1               5                   10                  15

Trp Ser Arg

<210> SEQ ID NO 8
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3,10
<223> OTHER INFORMATION: linked by the hydrocarbon linkage

<400> SEQUENCE: 8

Lys Trp Arg Ser Ala Gly Trp Arg Trp Arg Leu Trp Arg Val Arg Ser
1               5                   10                  15

Trp Ser Arg

<210> SEQ ID NO 9
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8,15
<223> OTHER INFORMATION: linked by the hydrocarbon linkage

<400> SEQUENCE: 9

Lys Trp Arg Ser Ala Gly Trp Arg Trp Arg Leu Trp Arg Val Arg Ser
1               5                   10                  15

Trp Ser Arg

<210> SEQ ID NO 10
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4,8
<223> OTHER INFORMATION: linked by the hydrocarbon linkage

<400> SEQUENCE: 10

Lys Trp Arg Ser Ala Leu Tyr Arg Trp Arg Leu Trp Arg Ser Arg Ser
1               5                   10                  15

Trp Ser Arg

<210> SEQ ID NO 11
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3,10
<223> OTHER INFORMATION: linked by the hydrocarbon linkage

<400> SEQUENCE: 11

Lys Trp Arg Ser Ala Leu Tyr Arg Trp Arg Leu Trp Arg Ser Arg Ser
1               5                   10                  15
```

Trp Ser Arg

<210> SEQ ID NO 12
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8,15
<223> OTHER INFORMATION: linked by the hydrocarbon linkage

<400> SEQUENCE: 12

Lys Trp Arg Ser Ala Leu Tyr Arg Trp Arg Leu Trp Arg Ser Arg Ser
1               5                   10                  15

Trp Ser Arg

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10,14
<223> OTHER INFORMATION: linked by the hydrocarbon linkage

<400> SEQUENCE: 13

Lys Trp Arg Ser Ala Leu Tyr Arg Trp Arg Leu Trp Arg Ser Arg Ser
1               5                   10                  15

Trp Ser Arg

<210> SEQ ID NO 14
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14,18
<223> OTHER INFORMATION: linked by the hydrocarbon linkage

<400> SEQUENCE: 14

Lys Trp Arg Ser Ala Leu Tyr Arg Trp Arg Leu Trp Arg Ser Arg Ser
1               5                   10                  15

Trp Ser Arg

<210> SEQ ID NO 15
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3,10
<223> OTHER INFORMATION: linked by the hydrocarbon linkage

<400> SEQUENCE: 15

Lys Trp Arg Ser Ala Leu Tyr Arg Trp Arg Leu Trp Arg Ser Ala Leu
1               5                   10                  15

Tyr Ser Arg

```
<210> SEQ ID NO 16
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4,8
<223> OTHER INFORMATION: linked by the hydrocarbon linkage

<400> SEQUENCE: 16

Lys Trp Arg Ser Ala Leu Tyr Arg Trp Arg Leu Trp Arg Ser Ala Leu
1               5                   10                  15

Tyr Ser Arg

<210> SEQ ID NO 17
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10,14
<223> OTHER INFORMATION: linked by the hydrocarbon linkage

<400> SEQUENCE: 17

Lys Trp Arg Ser Ala Leu Tyr Arg Trp Arg Leu Trp Arg Ser Ala Leu
1               5                   10                  15

Tyr Ser Arg

<210> SEQ ID NO 18
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 14,18
<223> OTHER INFORMATION: linked by the hydrocarbon linkage

<400> SEQUENCE: 18

Lys Trp Arg Ser Ala Leu Tyr Arg Trp Arg Leu Trp Arg Ser Ala Leu
1               5                   10                  15

Tyr Ser Arg

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Gly Leu Trp Arg Ala Leu Trp Arg Leu Leu Arg Ser Leu Trp Arg Leu
1               5                   10                  15

Leu Trp Lys Val
            20

<210> SEQ ID NO 20
<211> LENGTH: 19
<212> TYPE: PRT
<213> ORGANISM: Artificial Sequence
<220> FEATURE:
```

```
<223> OTHER INFORMATION: Synthetic Construct

<400> SEQUENCE: 20

Leu Trp Arg Ala Leu Trp Arg Leu Trp Arg Ser Leu Trp Arg Leu Leu
1               5                   10                  15

Trp Lys Ala

<210> SEQ ID NO 21
<211> LENGTH: 19
<212> TYPE: PRT
<213> ORGANISM: Artificial Sequence
<220> FEATURE:
<223> OTHER INFORMATION: Synthetic Construct

<400> SEQUENCE: 21

Leu Trp Arg Ala Leu Trp Arg Leu Leu Arg Ser Leu Trp Arg Leu Trp
1               5                   10                  15

Arg Lys Ala

<210> SEQ ID NO 22
<211> LENGTH: 19
<212> TYPE: PRT
<213> ORGANISM: Artificial Sequence
<220> FEATURE:
<223> OTHER INFORMATION: Synthetic Construct

<400> SEQUENCE: 22

Leu Trp Arg Ala Leu Trp Arg Leu Trp Arg Ser Leu Trp Arg Leu Trp
1               5                   10                  15

Arg Lys Ala

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Leu Trp Arg Ala Leu Trp Arg Leu Leu Arg Ala Leu Trp Arg Leu Leu
1               5                   10                  15

Trp Lys Ala

<210> SEQ ID NO 24
<211> LENGTH: 19
<212> TYPE: PRT
<213> ORGANISM: Artificial Sequence
<220> FEATURE:
<223> OTHER INFORMATION: Synthetic Construct

<400> SEQUENCE: 24

Leu Trp Arg Ala Leu Trp Arg Leu Leu Arg Asn Leu Trp Arg Leu Leu
1               5                   10                  15

Trp Lys Ala

<210> SEQ ID NO 25
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

-continued

```
<223> OTHER INFORMATION: Xaa = Any Amino Acid, and may be present or
      absent
<220> FEATURE:
<221> NAME/KEY: VARIANT
<222> LOCATION: 2, 3, 6, 7, 10, 11, 12, 13, 14, 15, 16, 17, 19
<223> OTHER INFORMATION: Xaa = Any Amino Acid

<400> SEQUENCE: 25

Xaa Xaa Xaa Trp Trp Xaa Xaa Trp Ala Xaa Xaa Xaa Xaa Xaa Xaa
1               5                   10                  15

Xaa Trp Xaa Arg
            20

<210> SEQ ID NO 26
<211> LENGTH: 19
<212> TYPE: PRT
<213> ORGANISM: Artificial Sequence
<220> FEATURE:
<223> OTHER INFORMATION: Synthetic Construct

<400> SEQUENCE: 26

Leu Arg Trp Trp Leu Arg Trp Ala Ser Arg Trp Phe Ser Arg Trp Ala
1               5                   10                  15

Trp Trp Arg

<210> SEQ ID NO 27
<211> LENGTH: 19
<212> TYPE: PRT
<213> ORGANISM: Artificial Sequence
<220> FEATURE:
<223> OTHER INFORMATION: Synthetic Construct

<400> SEQUENCE: 27

Leu Arg Trp Trp Leu Arg Trp Ala Ser Arg Trp Ala Ser Arg Trp Ala
1               5                   10                  15

Trp Phe Arg

<210> SEQ ID NO 28
<211> LENGTH: 18
<212> TYPE: PRT
<213> ORGANISM: Artificial Sequence
<220> FEATURE:
<223> OTHER INFORMATION: Synthetic Construct

<400> SEQUENCE: 28

Arg Trp Trp Leu Arg Trp Ala Ser Arg Trp Ala Leu Ser Trp Arg Trp
1               5                   10                  15

Trp Arg

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct

<400> SEQUENCE: 29
caucaucccu gccucuacut t                                          21

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct
```

```
<400> SEQUENCE: 30
aguagaggca gggaugaugt t                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
ggcgaagauc aacauggcat t                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic Construct

<400> SEQUENCE: 32
ugccauguug aucuucgcct t                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct

<400> SEQUENCE: 33
ggugaagauc agcauggcat t                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic Construct

<400> SEQUENCE: 34
ugccaugucg aucuucacct t                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic Construct

<400> SEQUENCE: 35
ugccaugucg aucuucacct t                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic Construct

<400> SEQUENCE: 36
ugccaugucg aucuucacct t                                              21

<210> SEQ ID NO 37
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 37
gcaaaggcgu gccaacucat t                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic Construct

<400> SEQUENCE: 38
tgaguuggca cgccuuugct t                                              21

<210> SEQ ID NO 39
<211> LENGTH: 9
<212> TYPE: DNA
<213> ORGANISM: Artificial Sequence
<220> FEATURE:
<223> OTHER INFORMATION: Synthetic Construct

<400> SEQUENCE: 39 cgacgacga                                                             9

<210> SEQ ID NO 40
<211> LENGTH: 12
<212> TYPE: DNA
<213> ORGANISM: Artificial Sequence
<220> FEATURE:
<223> OTHER INFORMATION: Synthetic Construct

<400> SEQUENCE: 40
cgacgacgac ga                                                        12

<210> SEQ ID NO 41
<211> LENGTH: 22
<212> TYPE: RNA
<213> ORGANISM: Artificial Sequence
<220> FEATURE:
<223> OTHER INFORMATION: Synthetic Construct

<400> SEQUENCE: 41
uggcagugug guuagcuggu ug                                             22
```

PEPTIDES AND NANOPARTICLES FOR INTRACELLULAR DELIVERY OF MOLECULES

CROSS REFERENCE TO RELATED APPLICATIONS

This application is a Continuation application of U.S. Ser. No. 15/539,619, claiming the International Filing date of Dec. 23, 2015, which is the National Stage filing of PCT/EP2015/081197, entitled "PEPTIDES AND NANOPARTICLES FOR INTRACELLULAR DELIVERY OF MOLECULES" with the International Filing Date of Dec. 23, 2015, which claims the benefit of priority from French Application Serial No. 14/03004, filed Dec. 24, 2014, each of which are hereby incorporated by reference in their entirety for all purposes as if put forth in full below.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737372000201SEQLIST.TXT, date recorded: Jul. 13, 2020, size: 12 KB).

TECHNICAL FIELD

The present invention pertains to peptides and peptide-containing complexes/nanoparticles that are useful for stabilizing and delivering cargo molecules such as nucleic acids.

BACKGROUND

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications, (d) rapid endosomal release, and (e) ability to reach the target. Although viral delivery strategies had given much hope for gene and cellular therapies, their clinical application has suffered from side- and toxicity-effects (Ibraheem et al. (2014) *Int J Pharm* 459, 70-83). Researches were mainly focused on the development of non-viral strategies, and different methods have been proposed including lipid, polycationic nanoparticles and peptide-based formulations, but only few of these technologies have been efficient in vivo and have reached the clinic (Yin et al. (2014) *Nat Rev Genet* 15, 541-555). Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge (Langel U (2007) *Handbook of Cell-Penetrating Peptides* (CRC Taylor & Francis, Boca Raton); Heitz et al. (2009) *Br J Pharmacol* 157, 195-206). CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models (Langel U (2007) *Handbook of Cell-Penetrating Peptides* (CRC Taylor & Francis, Boca Raton); Heitz et al. (2009) *Br J Pharmacol* 157, 195-206; Mickan et al. (2014) *Curr Pharm Biotechnol* 15, 200-209; Shukla et al. (2014) *Mol Pharm* 11, 3395-3408).

The concept of protein transduction domain (PTD) was initially proposed based on the observation that some proteins, mainly transcription factors, could shuttle within cells and from one cell to another (for review see Langel U (2007) *Handbook of Cell-Penetrating Peptides* (CRC Taylor & Francis, Boca Raton); Heitz et al. (2009) *Br J Pharmacol* 157, 195-206). The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake, and the first proofs-of-concept of the application of PTD in vivo were reported by the group of Dowdy for the delivery of small peptides and large proteins (Gump J M, and Dowdy S F (2007) *Trends Mol Med* 13, 443-448.). Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs (peptide nucleic acids) both in cultured cells and in vivo (Langel U (2007) *Handbook of Cell-Penetrating Peptides* (CRC Taylor & Francis, Boca Raton)). In 1997, the group of Heitz and Divita proposed a new strategy involving CPP in the formation of stable but non-covalent complexes with their cargo (Morris et al. (1997) *Nucleic Acids Res* 25, 2730-2736). The strategy was first based on the short peptide carrier (MPG) consisting of two domains: a hydrophilic (polar) domain and a hydrophobic (apolar) domain. MPG was designed for the delivery of nucleic acids. The primary amphipathic peptide Pep-1 was then proposed for non-covalent delivery of proteins and peptides (Morris et al. (2001) *Nat Biotechnol* 19, 1173-1176). Then the groups of Wender and of Futaki demonstrated that polyarginine sequences (Arg8) are sufficient to drive small and large molecules into cells and in vivo (Nakase et al. (2004) *Mol Ther* 10, 1011-1022; Rothbard et al. (2004) *J Am Chem Soc* 126, 9506-9507). Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides (Heitz et al. (2009) *Br J Pharmacol* 157, 195-206). More recently, a new non-covalent strategy based on secondary amphipathic CPPs has been described. These peptides such as CADY and VEPEP-families are able to self-assemble in a helical shape with hydrophilic and hydrophobic residues on different side of the molecule. WO2012/137150 discloses VEPEP-6 peptides; US2010/0099626 discloses CADY peptides; and WO2014/053880 discloses VEPEP-9.

The disclosures of all publications, patents, patent applications and published patent applications referred to herein are hereby incorporated herein by reference in their entirety.

BRIEF SUMMARY OF THE INVENTION

The present application provides a novel class of peptides (ADGN peptides) useful for stabilizing and delivering cargo molecules such as nucleic acids. In one aspect, there is provided a non-naturally occurring peptide comprising an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the peptide is 19 or 20 amino acids in length. In some embodiments, the peptide is no more than about any of 50, 45, 40, 35, 30, 25, or 20 amino acids in length. In some embodiments, the peptide is no less than about any of 50, 100, 200, 300, 400, 500, 1000, or more amino acids in length. In some embodiments, the peptide comprises an L-amino acid. In some embodiments, the peptide comprises a D-amino acid.

In some embodiments according to any of the peptides described above, the peptide further comprises one or more moieties covalently linked to the N-terminus of the peptide, wherein the one or more moieties are selected from the group consisting of an acetyl group, a stearyl group, a fatty acid, a cholesterol, a lipid (including a phospholipid), a poly-ethylene glycol, a nuclear localization signal, a nuclear export signal, an antibody or antibody fragment thereof, a peptide, a polysaccharide, and a targeting molecule. In some embodiments, the peptide comprises an acetyl group covalently linked to its N-terminus. In some embodiments, the peptide further comprises one or more moieties covalently linked to the C-terminus of the peptide, wherein the one or more moieties are selected from the group consisting of a cysteamide group, a cysteine, a thiol, an amide, a nitrilotriacetic acid, a carboxyl group, a linear or ramified $C_1$-$C_6$ alkyl group, a primary or secondary amine, an osidic derivative, a lipid, a phospholipid, a fatty acid, a cholesterol, a poly-ethylene glycol, a nuclear localization signal, a nuclear export signal, an antibody or antibody fragment thereof, a peptide, a polysaccharide, and a targeting molecule. In some embodiments, the peptide comprises a cysteamide group covalently linked to its C-terminus. In some embodiments, the peptide is "neat," i.e., does not contain any other moieties described above.

In some embodiments according to any of the peptides described above, the peptide is stapled. For example, in some embodiments, the peptide comprises a hydrocarbon linkage between two residues that are separated by three or six residues. In some embodiments, the peptide comprises the amino acid sequence of:

aa)
(SEQ ID NO: 7)
KWRS$_S$AGWR$_S$WRLWRVRSWSR, ab)
(SEQ ID NO: 8)
KWR$_S$SAGWRWR$_S$LWRVRSWSR, ac)
(SEQ ID NO: 9)
KWRSAGWR$_S$WRLWRVR$_S$SWSR, ba)
(SEQ ID NO: 10)
KWRS$_S$ALYR$_S$WRLWRSRSWSR, bb)
(SEQ ID NO: 11)
KWR$_S$SALYRWR$_S$LWRSRSWSR, bc)
(SEQ ID NO: 12)
KWRSALYR$_S$WRLWRSR$_S$SWSR, bd)
(SEQ ID NO: 13)
KWRSALYRWR$_S$LWRS$_S$RSWSR, be)
(SEQ ID NO: 14)
KWRSALYRWRLWRS$_S$RSWS$_S$R, ca)
(SEQ ID NO: 15)
KWR$_S$SALYRWR$_S$LWRSALYSR, cb)
(SEQ ID NO: 16)
KWRS$_S$ALYR$_S$WRLWRSALYSR, cc)
(SEQ ID NO: 17)
KWRSALYRWR$_S$LWRS$_S$ALYSR,
or cd)
(SEQ ID NO: 18)
KWRSALYRWRLWRS$_S$ALYS$_S$R, wherein the residues marked with a subscript "S" are the two residues linked by the hydrocarbon linkage.

In some embodiments according to any one of the peptides described above, the portion of the peptide having the sequence $X_1KWRSX_2X_3X_4RWRLWRX_5X_6X_7X_8SR$ (SEQ ID NO: 1) forms a single core helical motif. In some embodiments, the portion of the peptide having the sequence $X_1KWRSX_2X_3X_4RWRLWRX_5X_6X_7X_8SR$ (SEQ ID NO: 1) forms a helical structure wherein the S or R residues are on the same side, and the W residues are on the other side, forming a patch of electrostatic contacts on one side and hydrophobic contacts on the other side of the helix.

In another aspect of the invention, there is provided a complex comprising (including consisting essentially of or consisting of) any one of the ADGN peptides as described above and a cargo molecule. In another aspect of the present application, there is provided a nanoparticle comprising (including consisting essentially of or consisting of) any one of the ADGN peptides as described above and a cargo molecule. In some embodiments, the cargo is charged. In some embodiments, the cargo is uncharged. In some embodiments, the cargo is physically or chemically modified. In some embodiments, the cargo is unmodified. In some embodiments, the cargo molecule is a nucleic acid. In some embodiments, the nucleic acid is selected from the group consisting of an siRNA, an miRNA, an anti-sense RNA, a DNA plasmid, and an analogue thereof. In some embodiments, the nucleic acid is an oligonucleotide. In some embodiments, the DNA plasmid encodes a chimeric antigen receptor comprising an extracellular antigen binding domain that specifically binds to a target antigen, a transmembrane domain, and an intracellular signaling domain. In some embodiments, the target antigen is selected from the group consisting of CD19, CD20, CD28, OX40, GITR, CD137, CD27, HVEM, BCMA, CD70, CD74, CD38, CD138, CD33, Lewis-Y, CD123, CD44v6 and CS1. In some embodiments, the nucleic acid is selected from the group consisting of a single-stranded RNA, a single-stranded DNA, a double-stranded RNA, a double-stranded DNA, and derivatives thereof. In some embodiments, the nucleic acid is from about 2 to about 40 nucleotides in length. In some embodiments, the nucleic acid is up to about 100 nucleotides in length. In some embodiments, the nucleic acid is greater than about 100 nucleotides in length. In some embodiments, the nucleic acid contains at least one modified linkage, such as a phosphorothioate linkage or modifications at the 2' position of the ribose ring including 2'-methoxy, 2'-fluoro, and 2'-O-methoxyethyl.

In some embodiments according to any of the complexes or nanoparticles described above, the molar ratio of the cargo molecule to the ADGN peptide in the complex or nanoparticle is from about 1:1 to about 1:80 (including for example about any of about 1:1 to about 1:5, about 1:5 to about 1:10, about 1:10 to about 1:15, about 1:15 to about 1:20, about 1:20 to about 1:25, about 1:25 to about 1:30, about 1:30 to about 1:35, about 1:35 to about 1:40, about 1:40 to about 1:45, about 1:45 to about 1:50, about 1:50 to about 1:55, about 1:55 to about 1:60, about 1:60 to about 1:65, about 1:65 to about 1:70, about 1:70 to about 1:75, and about 1:75 to about 1:80).

In some embodiments, the cargo molecule is complexed with an assembly molecule (such as a peptide, a protein, an antibody, a lipid, a phospholipid, a polymer, an aptamer, a nanoparticle, a liposome, a dendrimer, a polymerosome, a viral vector, and a micelle) to form a core of a nanoparticle. In some embodiments, the assembly molecule is any one of the ADGN peptides as described above (for example the nanoparticle may comprise (including consisting essentially of or consisting of) a core comprising an ADGN peptide and a cargo molecule). In some embodiments, the assembly molecule is not an ADGN peptide (for example, the nanoparticle may comprise a core comprising a cargo molecule and a non-ADGN peptide, which is then coated with an ADGN peptide). In some embodiments, the nanoparticle further comprises a surface layer. In some embodiments, the surface layer comprises any one of the ADGN peptides as described above. In some embodiments, the surface layer comprises a cell-penetrating peptide that is not an ADGN peptide. In some embodiments, the nanoparticle further comprises an intermediate layer. In some embodiments, the intermediate layer comprises any one of the ADGN peptides as described above. In some embodiments, the intermediate layer comprises a cell-penetrating peptide that is not an ADGN peptide.

In some embodiments according to any one of the nanoparticles described above, the nanoparticle comprises a targeting moiety at the surface. In some embodiments, the targeting moiety is linked to a peptide (such as an AGDN peptide). In some embodiments, the peptide is covalently linked to the targeting moiety. In some embodiments, the targeting moiety targets the nanoparticle to a tissue or specific cell.

In some embodiments according to any one of the nanoparticles described above, the size (diameter) of the nanoparticle is from about 10 nm to about 300 nm. In some embodiments, the size (diameter) of the nanoparticle is from about 50 nm to about 200 nm. In some embodiments, the size (diameter) of the nanoparticle is from about 80 nm to about 140 nm. In some embodiments, the size (diameter) of the nanoparticles is no more than about any one of 150 nm, 140 nm, 130 nm, 120 nm, 110 nm, or 100 nm.

In some embodiments, the absolute value of the zeta potential of the nanoparticles is no more than about 50 mV, including for example no more than about any of 40 mV, 30 mV, 20 mV, 10 mV, 9 mV, 8 mV, 7 mV, 6 mV, or 5 mV. In some embodiments, the zeta potential of the nanoparticles is about −15 to about 15 mV, such as about −5 to about 10 mV.

In some embodiments according to any one of the nanoparticles or complexes described above, the nanoparticle or complex comprises a plurality of cargo molecules. In some embodiments, the nanoparticle or complex comprises at least about any of 2, 3, 4, 5, 6, 7, 8, 9, or 10 different cargo molecules (such as nucleic acids). In some embodiments, the cargos are of the same kind (e.g., a plurality of miRNAs or siRNAs). In some embodiments, the cargos are of different kinds.

In some embodiments, there is provided a composition (such as a pharmaceutical composition) comprising any one of the nanoparticles described above. In some embodiments, the average diameter of the nanoparticles in the composition is from about 10 nm to about 300 nm. In some embodiments, the average diameter of the nanoparticles in the composition is from about 50 nm to about 200 nm. In some embodiments, the average diameter of the nanoparticles in the composition is from about 80 nm to about 140 nm. In some embodiments, the average diameter of the nanoparticles in the composition is no more than about any one of 150 nm, 140 nm, 130 nm, 120 nm, 110 nm, or 100 nm. In some embodiments, the composition has a polydispersity index of no more than about any of 0.1, 0.2, 0.3, 0.4, or 0.5. In some embodiments, the nanoparticles within the composition comprise the same ADGN peptides and cargo molecules. In some embodiments, the nanoparticles within the composition comprise different ADGN peptides and/or cargo molecules.

In some embodiments, the nanoparticle composition is a liquid suspension of the nanoparticles. In some embodiments, the nanoparticle composition is lyophilized. In some embodiments, the nanoparticle composition is stable for at least about any of 24 hours, 48 hours, 72 hours, 4 days, 10 days, 30 days, 60 days, three months, four months, five months, six months, or longer at room temperature or under refrigerated conditions, for example without precipitation, aggregation, size change, and/or loss of efficacy.

In another aspect of the present application, there is provided a pharmaceutical composition comprising a complex or nanoparticle as described above and a pharmaceutically acceptable carrier. In some embodiments, the pharmaceutical composition is formulated for intravenous, intratumoral, intraarterial, topical, intraocular, ophthalmic, intracranial, intrathecal, intravesicular, intradermal, subcutaneous, intramuscular, intranasal, intratracheal, pulmonary, intracavity, or oral administration. In some embodiments, the pharmaceutically acceptable carrier comprises a sugar or a protein. In some embodiments, the sugar is selected from the group consisting of sucrose, glucose, mannitol, and a combination thereof, and optionally is present in the pharmaceutical composition at a concentration from about 5% to about 20%. In some embodiments, the protein is albumin. In some embodiments, the pharmaceutical composition is lyophilized.

In yet another aspect of the present application, there is provided a method of preparing a nanoparticle as described above, comprising a) combining an ADGN peptide as described above with a cargo molecule to form a mixture, and b) incubating the mixture to form the nanoparticle.

In another aspect of the present application, there is provided a method of stabilizing cargo molecules (such as a nucleic acid), comprising combining the cargo molecules with an ADGN peptide as described above, thereby stabilizing the cargo molecules. In some embodiments, the cargo molecule and the ADGN peptide form a complex or nanoparticle as described above. In some embodiments, the cargo molecule is a nucleic acid and the ADGN peptide stabilizes the supercoil structure of the nucleic acid. In some embodiments, the cargo molecule is susceptible to degradation (for example by serum components or nucleases in vitro or in vivo), and the ADGN peptide protects the cargo molecule from the degradation.

In a further aspect of the present application, there is provided a method of treating a disease in an individual comprising administering to the individual an effective amount of a pharmaceutical composition comprising a cargo molecule and ADGN peptide (e.g., in the form of complexes or nanoparticles) as described above. In some embodiments, the disease is selected from the group consisting of cancer, diabetes, inflammatory diseases, fibrosis, viral infectious diseases, hereditary diseases, and aging and degenerative diseases. In some embodiments, the disease is cancer, such as solid tumor.

In some embodiments, the administration of the pharmaceutical composition results in the modulation of the expression of one or more genes. Suitable genes whose expression can be modulated by the methods described herein include, but are not limited to, those encoding growth factors, cytokines, cell surface receptors, signaling molecules, kinases, transcription factors or other modulators of transcription, regulators of protein expression or modification, and regulators of apoptosis or metastasis. In some embodiments, at least one of the one or more genes encodes a growth factor or cytokine including, but not limited to, EGF, VEGF, FGF, HGF, HDGF, IGF, PDGF, TGF-α, TGF-β, TNF-α, and wnt. In some embodiments, at least one of the one or more genes encodes a growth factor or cytokine including, but not limited to, EGF, VEGF, FGF, HGF, HDGF, IGF, PDGF, TGF-α, TGF-β, TNF-α, and wnt. In some embodiments, at least one of the one or more genes encodes a cell surface receptor including, but not limited to, ER, PR, Her2, Her3, angiopoietin receptor, EGFR, FGFR, HGFR, HDGFR, IGFR, KGFR, MSFR, PDGFR, TGFR, VEGFR1, VEGFR2, VEGFR3, Frizzled family receptors (FZD-1 to 10), smoothened, patched, and CXCR4. In some embodiments, at least one of the one or more genes encodes a signaling molecule or kinase including, but not limited to, KRAS, NRAS, RAF, MEK, MEKK, MAPK, MKK, ERK, JNK, JAK, PKA, PKC, PI3K, Akt, mTOR, Raptor, Rictor, MLST8, PRAS40, DEPTOR, MSIN1, S6 kinase, PDK1, BRAF, FAK, Src, Fyn, Shc, GSK, IKK, PLK-1, cyclin-dependent kinases (Cdk1 to 13), CDK-activating kinases, ALK/Met, Syk, BTK, Bcr-Abl, RET, β-catenin, Mel-1, and PKN3. In some embodiments, at least one of the one or more genes encodes a transcription factor or other modulator of transcription including, but not limited to, ATF-2, Chop, c-Jun, c-Myc, DPC4, Elk-1, Ets1, Max, MEF2C, NFAT4, Sap1a, STATs, Tal, p53, CREB, Myc, NF-κB, HDACs, HIF-1α, and RRM2. In some embodiments, at least one of the one or more genes encodes a regulator of protein expression or modification including, but not limited to, ubiquitin ligase, LMP2, LMP7, MECL-1, and miRNAs. In some embodiments, at least one of the one or more genes encodes a regulator of apoptosis or metastasis including, but not limited to, XIAP, Bcl-2, osteopontin, SPARC, MMP-2, MMP-9, and uPAR.

In some embodiments, wherein the disease is a solid tumor, the gene whose expression is modulated may encode a protein involved in tumor development and/or progression. In some embodiments, the protein involved in tumor development and/or progression includes, but is not limited to, IL-2, IL-12, interferon-gamma, GM-CSF, B7-1, caspase-9, p53, MUC-1, MDR-1, HLA-B7/Beta 2-Microglobulin, Her2, Hsp27, thymidine kinase, and MDA-7.

In some embodiments, wherein the disease is a hematological malignancy, the gene whose expression is modulated may encode a protein involved in hematological malignancy development and/or progression. In some embodiments, the protein involved in hematological malignancy development and/or progression includes, but is not limited to, GLI1, CTNNB1, eIF5A, mutant DDX3X, Hexokinase II, histone methyltransferase EZH2, ARK5, ALK, MUC1, HMGA2, HIF-1 alpha, IRF1, RPN13, HDAC11, Rad51, Spry2, mir-146a, mir-146b, survivin, MDM2, MCL1, CMYC, XBP1 (spliced and unspliced), SLAMF7, CS1, Erbb4, Cxcr4 (waldenstroms macroglobulinemia), Myc, Bcl2, Prdx1 and Prdx2 (burkitts lymphoma), Bcl6, Idh1, Idh2, Smad, Ccnd2, Cyclin d1-2, B7-h1 (pdl-1), and Pyk2.

In some embodiments, wherein the disease is a viral infection disease, the gene whose expression is modulated may encode a protein involved in the viral infectious disease development and/or progression. In some embodiments, the protein involved in the viral infectious disease development and/or progression includes, but is not limited to, RSV nucleocapsid, Pre-gen/Pre-C, Pre-S1, Pre-S2/S, X, HBV conserved sequences, HIV Tat, HIV TAR RNA, human CCR5, miR-122, EBOV polymerase L, VP24, VP40, GP/sGP, VP30, VP35, NPC1, and TIM-1.

In some embodiments, wherein the disease is a hereditary disease, the gene whose expression is modulated may encode a protein involved in the hereditary disease development and/or progression. In some embodiments, the protein involved in the hereditary disease development and/or progression includes, but is not limited to, Transthyretin, MDS1-EVI1, PRDM16, SETBP1, ß-Globin, and LPL.

In some embodiments, wherein the disease is an aging or degenerative disease, the gene whose expression is modulated may encode a protein involved in the aging or degenerative disease development and/or progression. In some embodiments, the protein involved in the aging or degenerative disease development and/or progression includes, but is not limited to, keratin K6A, keratin K6B, keratin 16, keratin 17, p53, ß-2 adrenergic receptors (ADRB2), TRPV1, VEGF, VEGFR, HIF-1, HIF-1 alpha, and caspase-2.

In some embodiments, wherein the disease is a fibrotic or inflammatory disease, the gene whose expression is modulated may encode a protein involved in the fibrotic or inflammatory disease development and/or progression. In some embodiments, the protein involved in the fibrotic or inflammatory disease development and/or progression are selected from the group consisting of SPARC, CTGF, TGFβ1, TGFβ receptors 1, TGFβ receptors 2, TGFβ receptors 3, VEGF, Angiotensin II, TIMP, HSP47, thrombospondin, CCN1, LOXL2, MMP2, MMP9, CCL2, Adenosine receptor A2A, Adenosine receptor A2B, Adenylyl cyclase, Smad 3, Smad 4, Smad 7, SOX9, arrestin, PDCD4, PAI-1, NF-κB, and PARP-1.

In some embodiments according to any one of the treatment methods described above, the individual is a mammal. In some embodiments, the individual is human.

In another aspect of the invention, there is provided a method of delivering a cargo molecule into a cell comprising contacting the cell with a composition comprising an ADGN peptide and a cargo molecule (for example in the form of a complex or nanoparticle as described above). In some embodiments, the contacting of the cell is carried out in vivo. In some embodiments, the contacting of the cell is carried out ex vivo. In some embodiments, the contacting of the cell is carried out in vitro. In some embodiments, the cell is a granulocyte, a mast cell, a monocyte, a dendritic cell, a B cell, a T cell, or a natural killer cell. In some embodiments, the cargo molecule is a plasmid encoding a chimeric antigen receptor comprising an extracellular antigen-binding domain that specifically binds to a target antigen, a transmembrane domain, and an intracellular signaling domain. In some embodiments, the target antigen is a cancer-associated antigen. In some embodiments, the complex or nanoparticle further comprises an siRNA. In some embodiments, the method further comprises contacting the cell with a second composition comprising an ADGN peptide and an siRNA (for example in the form of a complex or nanoparticle as described above). In some embodiments, the siRNA specifically targets an RNA molecule encoding PD-1, PD-L1, PD-L2, TIM-3, BTLA, VISTA, LAG-3, or CTLA-4.

In some embodiments, according to any of the methods of delivering a cargo molecule into a cell described above, the cargo molecule is siRNA.

In another aspect of the invention, there is provided a method of treating a disease in an individual comprising a) delivering a molecule into a cell according to any one of the methods described above, thereby producing a modified cell comprising the molecule, wherein the modified cell is useful for the treatment of the disease; and b) administering the modified cell to the individual. In some embodiments, the modified cell is administered via an intravenous, intraarterial, intraperitoneal, intravesicular, subcutaneous, intrathecal, intrapulmonary, intramuscular, intratracheal, intraocular, transdermal, oral, or inhalation route. In some embodiments, the disease is cancer. In some embodiments, the individual is human.

In yet another aspect of the invention, there is provided a kit comprising a composition comprising any one of the ADGN peptides as described above and instructions for preparing a complex and/or a nanoparticle as described above. In some embodiments, the kit further comprises a composition comprising an assembly molecule selected from the group consisting of a peptide, a protein, an antibody, a lipid, a phospholipid, a polymer, an aptamer, a nanoparticle, a liposome, a dendrimer, a polymerosome, a viral vector, and a micelle.

DETAILED DESCRIPTION OF THE INVENTION

Figure 1A:
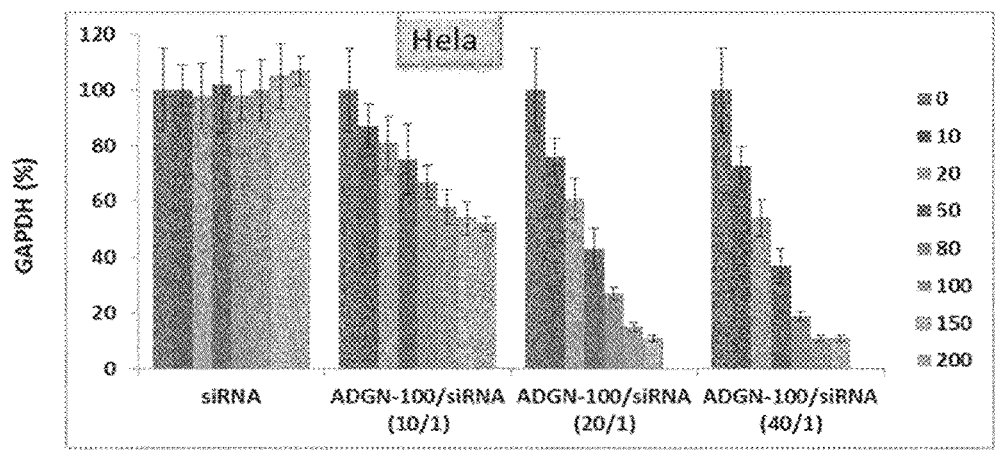
FIG. 1A shows in vitro delivery of GAPDH siRNA by peptide/siRNA particles in HeLa cells. The columns from left to right for each experimental group correspond to siRNA concentrations of 0 nM, 10 nM, 20 nM, 50 nM, 80 nM, 100 nM, 150 nM, and 200 nM, respectively.

The present application provides novel peptides (referred to herein as "ADGN peptides") suitable for stabilizing and delivering cargo molecules such as nucleic acids. The ADGN peptides comprise secondary amphipathic peptides, with poor sequence homology with any previously known cell penetrating peptides. Unlike previously known cell-penetrating peptides such as CADY and VEPEP-6, each containing multiple short helical motifs, the ADGN peptides contain a single core helical motif. The helical motif exposes S or R residues on one side, and W residues on the other, forming surfaces that are significantly different from those previously reported. Notably, complexes (such as nanoparticles) formed with the ADGN peptides and cargo molecules contain lower net residual positive charges (e.g., close to neutral). Further, despite the general understanding that high net residual positive charge is required for cell penetration, the ADGN peptides showed improved efficacy in cargo delivery when compared to previously known cell penetrating peptides. ADGN technology constitutes a potent nonviral delivery system for T cell engineering by promoting both gene delivery and cellular uptake of small oligonucleotides such as siRNA or antisense molecules. ADGN technology is less complex, less toxic and easier to use than viral vectors.

Thus, the present application in one aspect provides novel ADGN peptides which are described further below in more detail.

In another aspect, there are provided methods of stabilizing cargo molecules and methods of delivering cargo molecules by using the ADGN peptides.

In another aspect, there are provided complexes or nanoparticles comprising an ADGN peptide and a cargo molecule.

Also provided are pharmaceutical compositions comprising an ADGN peptide and a cargo molecule (for example in the forms of complexes and nanoparticles) and uses thereof for treating diseases.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

The compositions and methods of the present invention may comprise, consist of, or consist essentially of the essential elements and limitations of the invention described herein, as well as any additional or optional ingredients, components, or limitations described herein or otherwise useful.

Unless otherwise noted, technical terms are used according to conventional usage.

Peptides of the Present Invention

The present invention provides ADGN peptides capable of forming stable complexes and nanoparticles with various cargo molecules, such as small oligonucleotides or plasmid DNA.

In some embodiments, there is provided a peptide (for example a non-naturally occurring peptide) comprising the following amino acid sequence:

$X_1$KWRS$X_2X_3X_4$RWRLWR$X_5X_6X_7X_8$SR (SEQ ID NO: 1), wherein $X_1$ is any amino acid or none, and $X_2$-$X_8$ are any amino acid.

In some embodiments, the portion of the peptide having the sequence $X_1$KWRS$X_2X_3X_4$RWRLWR$X_5X_6X_7X_8$SR (SEQ ID NO: 1) forms a single core helical motif. In some embodiments, the portion of the peptide having the sequence $X_1$KWRS$X_2X_3X_4$RWRLWR$X_5X_6X_7X_8$SR (SEQ ID NO: 1) forms a helical structure where the S or R residues are on the same side, and the W residues are on the other side, forming a patch of electrostatic contacts and hydrophobic contacts on the other side of the helix. In some embodiments, the peptide has reduced toxicity relative to VEPEP-6 or CADY cell-penetrating peptides. In some embodiments, the peptide is 19 or 20 amino acids in length. In some embodiments, the peptide is no more than about any of 50, 45, 40, 35, 30, 25, or 20 amino acids in length. In some embodiments, the peptide is no less than about any of 50, 100, 200, 300, 400, 500, 1000, or more amino acids in length. In some embodiments, the peptide comprises and L-amino acid. In some embodiments, the peptide comprises a D-amino acid.

In some embodiments, the peptide comprise the following amino acid sequence:

$X_1$KWRS$X_2X_3X_4$RWRLWR$X_5X_6X_7X_8$SR (SEQ ID NO: 1), wherein $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y.

In some embodiments, the peptide comprises the amino acid sequence of:

a) KWRSAGWRWRLWRVRSWSR (SEQ ID NO: 2), b) KWRSALYRWRLWRSRSWSR (SEQ ID NO: 3), or c) KWRSALYRWRLWRSALYSR (SEQ ID NO: 4). In some embodiments, the peptide comprises the amino acid sequence of SEQ ID NO: 2. In some embodiments, the peptide comprises the amino acid sequence of SEQ ID NO: 3. In some embodiments, the peptide comprises the amino acid sequence of SEQ ID NO: 4.

In some embodiments, the peptides comprises the amino acid sequence of:

X₁KWRSAGWRWRLWRVRSWSR (SEQ ID NO: 5), wherein

X₁ is βA, S or none.

In some embodiments, the peptide has one or more features selected from the group consisting of:
a) one or more SR motifs,
b) one or more W or Y residues, and
c) R residues.

In some embodiments, the peptide remains mostly unfolded when free in solution. In some embodiments, the peptide is capable of adopting at least a partial helical structure in the presence of a cargo molecule. In some embodiments, the helical structure is a helix, such as, but not limited to, an α-helix. In some embodiments, the peptide adopts a helical structure throughout more than about 50% (such as more than about any of 55%, 60%, 70%, 75%, 80%, 85%, 90%, and 95%) of its length. In some embodiments, the helical structure is located mainly in a core motif of the peptide, wherein the core motif is the amino acid sequence RWRLWRX₅X₆X₇X₈SR (SEQ ID NO: 6), and wherein X₅ is V or S, X₆ is R, V, or A, X₇ is S or L, and X₈ is W or Y. In some embodiments, the peptide comprises a single helical motif. In some embodiments, the single helical motif is in the core motif. In some embodiments, the helical structure is configured such that at least 2 (such as at least any of 3, 4, 5, 6, 7, or 8) of the S and R residues are on one side of the helical structure and at least 1 (such as at least any of 2, 3, 4, or 5) of the W residues are on the opposite side of the helical structure. In some embodiments, a majority of the S and R residues are on one side of the helical structure and a majority of the W residues are on the opposite side of the helical structure. In some embodiments, all of the S and R residues are on one side of the helical structure and all of the W residues are on the opposite side of the helical structure. In some embodiments, the helical structure is configured such that a patch of electrostatic contacts is formed on one side of the helical structure and a patch of hydrophobic contacts is formed on the other side of the helical structure. In some embodiments, the peptide adopts a single helix in the presence of a cargo molecule.

In some embodiments, the peptide, when complexed to a cargo molecule, has a lower net residual positive charge than a previously described CPP (such as CADY or VEPEP-6) complexed to the same cargo molecule. In some embodiments, the peptide, when complexed to a cargo molecule, has a net residual positive charge less than about 80% (such as less than about any of 70%, 60%, 50%, 40%, 30%, or 20%) of the net residual positive charge of a previously described CPP complexed to the same cargo molecule. In some embodiments, the previously described CPP is CADY or VEPEP-6.

TABLE 1 sequence of ADGN peptides and previously described peptides

| Peptides | Sequence |
|---|---|
| ADGN Peptides | a: KWRSAGWRWRLWRVRSWSR (SEQ ID NO: 2) |
| | b: KWRSALYRWRLWRSRSWSR (SEQ ID NO: 3) |
| | c: KWRSALYRWRLWRSALYSR (SEQ ID NO: 4) |

TABLE 1-continued sequence of ADGN peptides and previously described peptides

| Peptides | Sequence |
|---|---|
| CADY | a: GLWRALWRLLRSLWRLLWKV (SEQ ID NO: 19) |
| VEPEP-6 | a: LWRALWRLWRSLWRLLWKA (SEQ ID NO: 20) |
| | b: LWRALWRLLRSLWRLWRKA (SEQ ID NO: 21) |
| | c: LWRALWRLWRSLWRLWRKA (SEQ ID NO: 22) |
| | d: LWRALWRLLRALWRLLWKA (SEQ ID NO: 23) |
| | e: LWRALWRLLRNLWRLLWKA (SEQ ID NO: 24) |
| VEPEP-9 | a: LRWWLRWASRWFSRWAWWR (SEQ ID NO: 26) |
| | b: LRWWLRWASRWASRWAWFR (SEQ ID NO: 27) |
| | c: RWWLRWASRWALSWRWWR (SEQ ID NO: 28) |

In some embodiments, the ADGN peptide further comprises one or more moieties linked to the N-terminus of the peptide. In some embodiments, the one or more moieties is covalently linked to the N-terminus of the peptide. In some embodiments, the one or more moieties are selected from the group consisting of an acetyl group, a stearyl group, a fatty acid, a cholesterol, a poly-ethylene glycol, a nuclear localization signal, a nuclear export signal, an antibody or antibody fragment thereof, a peptide, a polysaccharide, and a targeting molecule. In some embodiments, the one or more moieties is an acetyl group and/or a stearyl group. In some embodiments, the peptide comprises an acetyl group and/or a stearyl group linked to its N-terminus. In some embodiments, the peptide comprises an acetyl group linked to its N-terminus. In some embodiments, the peptide comprises a stearyl group linked to its N-terminus. In some embodiments, the peptide comprises an acetyl group and/or a stearyl group covalently linked to its N-terminus. In some embodiments, the peptide comprises an acetyl group covalently linked to its N-terminus. In some embodiments, the peptide comprises a stearyl group covalently linked to its N-terminus.

In some embodiments, the ADGN peptide further comprises one or more moieties linked to the C-terminus of the peptide. In some embodiments, the one or more moieties is covalently linked to the C-terminus of the peptide. In some embodiments, the one or more moieties are selected from the group consisting of a cysteamide group, a cysteine, a thiol, an amide, a nitrilotriacetic acid, a carboxyl group, a linear or ramified $C_1$-$C_6$ alkyl group, a primary or secondary amine, an osidic derivative, a lipid, a phospholipid, a fatty acid, a cholesterol, a poly-ethylene glycol, a nuclear localization signal, a nuclear export signal, an antibody or antibody fragment thereof, a peptide, a polysaccharide, and a targeting molecule. In some embodiments, the one or more moieties is a cysteamide group. In some embodiments, the peptide comprises a cysteamide group linked to its C-terminus. In some embodiments, the peptide comprises a cysteamide group covalently linked to its C-terminus.

In some embodiments, the ADGN peptide is stapled. "Stapled" as used herein refers to a chemical linkage between two residues in a peptide. In some embodiments, the ADGN peptide is stapled, comprising a chemical linkage between two amino acids of the peptide. In some embodiments, the two amino acids linked by the chemical linkage are separated by 3 or 6 amino acids. In some embodiments, two amino acids linked by the chemical linkage are separated by 3 amino acids. In some embodiments, the two amino acids linked by the chemical linkage are separated by 6 amino acids. In some embodiments, each of the two amino acids linked by the chemical linkage is R or S. In some embodiments, each of the two amino acids linked by the chemical linkage is R. In some embodiments, each of the two amino acids linked by the chemical linkage is S. In some embodiments, one of the two amino acids linked by the chemical linkage is R and the other is S. In some embodiments, the chemical linkage is a hydrocarbon linkage.

In some embodiments, the ADGN peptide is stapled and comprises the amino acid sequence of:

aa)
KWRS$_S$AGWR$_S$WRLWRVRSWSR, (SEQ ID NO: 7)

ab)
KWR$_S$SAGWRWR$_S$LWRVRSWSR, (SEQ ID NO: 8)

ac)
KWRSAGWR$_S$WRLWRVR$_S$SWSR, (SEQ ID NO: 9)

ba)
KWRS$_S$ALYR$_S$WRLWRSRSWSR, (SEQ ID NO: 10)

bb)
KWR$_S$SALYRWR$_S$LWRSRSWSR, (SEQ ID NO: 11)

bc)
KWRSALYR$_S$WRLWRSR$_S$SWSR, (SEQ ID NO: 12)

bd)
KWRSALYRWR$_S$LWRS$_S$RSWSR, (SEQ ID NO: 13)

be)
KWRSALYRWRLWRS$_S$RSWS$_S$R, (SEQ ID NO: 14)

ca)
KWR$_S$SALYRWR$_S$LWRSALYSR, (SEQ ID NO: 15)

cb)
KWRS$_S$ALYR$_S$WRLWRSALYSR, (SEQ ID NO: 16)

cc)
KWRSALYRWR$_S$LWRS$_S$ALYSR, (SEQ ID NO: 17)
or cd)
KWRSALYRWRLWRS$_S$ALYS$_S$R, (SEQ ID NO: 18)

and wherein the residues marked with a subscript "S" are the two residues linked by the hydrocarbon linkage.

Complexes and Nanoparticles

In some embodiments, there is provided a complex comprising an ADGN peptide and a cargo molecule. In some embodiments, the mean size (diameter) of the complex is between any of about 30 nm and about 10 microns, including for example between about 50 nm and about 1 micron, between about 50 nm and about 400 nm, between about 100 nm and about 300 nm, and between about 150 nm and about 200 nm. In some embodiments, the molar ratio of the peptide to the cargo molecule in the complex is between about 100:1 and about 1:50, including for example between about 50:1 and about 1:20, between about 20:1 and about 1:10, and between about 5:1 and about 1:1. In some embodiments, the complex is substantially non-toxic. In some embodiments, the complex comprises a plurality of cargo molecules. In some embodiments, the complex comprises a plurality of cargo molecules present in a predetermined ratio. In some embodiments, the predetermined ratio is selected to allow the most effective use of the complex in any of the methods described below in more detail.

In some embodiments, the complex comprises a targeting moiety. In some embodiments, the targeting moiety is linked to an ADGN peptide. In some embodiments, the targeting moiety is covalently linked to the ADGN peptide. In some embodiments, the targeting moiety targets the complex to a tissue or a specific cell type. In some embodiments, the tissue is a tissue in need of treatment. In some embodiments, the complex comprises a targeting moiety that targets the complex to a tissue or cell that can be treated by the cargo molecule of the complex.

In some embodiments, there is provided a nanoparticle comprising an ADGN peptide and a cargo molecule. In some embodiments, the mean size (diameter) of the nanoparticle is from about 10 nm to about 300 nm, including for example from about 50 nm to about 200 nm, from about 60 nm to about 180 nm, from about 80 nm to about 140 nm, and from about 90 nm to about 120 nm. In some embodiments, the molar ratio of the peptide to the cargo molecule in the nanoparticle is between about 100:1 and about 1:50, including for example between about 100:1 and about 1:20, between about 90:1 and about 1:10, between about 80:1 and about 1:1, and between about 40:1 and about 5:1. In some embodiments, the zeta potential of the nanoparticle is from about −30 mV to about 30 mV, including for example from about −25 mV to about 25 mV, from about −20 mV to about 20 mV, from about −15 mV to about 15 mV, from about −10 mV to about 10 mV, and from about −5 mV to about 10 mV. In some embodiments, the nanoparticle is substantially non-toxic. In some embodiments, the nanoparticle comprises a plurality of cargo molecules. In some embodiments, the nanoparticle comprises a plurality of cargo molecules present in a predetermined ratio. In some embodiments, the predetermined ratio is selected to allow the most effective use of the nanoparticle in any of the methods described below in more detail.

In some embodiments, the nanoparticle comprises the cargo molecule complexed with an assembly molecule. The complex of the cargo molecule and the assembly molecule may comprise covalent or non-covalent interactions between the cargo molecule and the assembly molecule. In some embodiments, the cargo molecule complexed with the assembly molecule forms a core of the nanoparticle. In some embodiments, the assembly molecule is selected from the group consisting of a peptide, a protein, an antibody, a lipid, a phospholipid, a polymer, an aptamer, a nanoparticle, a liposome, a dendrimer, a polymerosome, a viral vector, and a micelle. In some embodiments, the peptide is a cell-penetrating peptide. In some embodiments, the cell-penetrating peptide is an ADGN peptide as described above. In some embodiments, the cell-penetrating peptide is not an ADGN peptide as described above, and includes, but is not limited to, a PTD-based peptide, an amphipathic peptide, a poly-arginine-based peptide, an MPG peptide, a CADY peptide, a VEPEP peptide, a Pep-1 peptide, and a Pep-2 peptide.

In some embodiments, the nanoparticle further comprises a surface layer. In some embodiments, the surface layer comprises an ADGN peptide as described above. In some embodiments, the surface layer comprises a cell-penetrating peptide that is not an ADGN peptide as described above. In some embodiments, the surface layer does not comprise a peptide. In some embodiments, the nanoparticle further comprises an intermediate layer between the core of the nanoparticle and the surface layer. In some embodiments, the intermediate layer comprises an ADGN peptide as described above. In some embodiments, the intermediate layer comprises a cell-penetrating peptide that is not an ADGN peptide as described above. In some embodiments, the nanoparticle comprises a targeting moiety at its surface. In some embodiments, the targeting moiety is linked to a peptide. In some embodiments, the targeting moiety is covalently linked to a peptide. In some embodiments, the targeting moiety targets the nanoparticle to a tissue or a specific cell type. In some embodiments, the tissue is a tissue in need of treatment. In some embodiments, the nanoparticle comprises a targeting moiety at its surface that targets the nanoparticle to a tissue or cell that can be treated by the cargo molecule of the nanoparticle.

In some embodiments, there is provided a complex comprising a cargo molecule (such as at least 1, 2, 3, 4, 5, or more cargo molecules) and a peptide, wherein the peptide comprises (including for example consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, there is provided a complex comprising a nucleic acid molecule (such as at least 1, 2, 3, 4, 5, or more nucleic acid molecules) and a peptide, wherein the peptide comprises (including consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the cargo molecule to the peptide in the complex is about 1:10 to about 1:40 (such as about 1:20 or about 1:40).

In some embodiments, there is provided a composition comprising nanoparticles comprising a cargo molecule (such as at least 1, 2, 3, 4, 5, or more cargo molecules) and a peptide, wherein the peptide comprises (including for example consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, there is provided a composition comprising nanoparticles comprising a nucleic acid molecule (such as at least 1, 2, 3, 4, 5, or more nucleic acid molecules) and a peptide, wherein the peptide comprises (including consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the cargo molecule to the peptide in the nanoparticle is about 1:10 to about 1:40 (such as about 1:20 or about 1:40). In some embodiments, the average diameter of the nanoparticles in the composition is no more than about 130 nm. In some embodiments, the absolute zeta potential of the nanoparticles in the composition is no more than about 10 mV. In some embodiments, the polydispersity of the nanoparticles in the composition is no more than about 1.5.

In some embodiments, there is provided a composition comprising nanoparticles comprising: a) a core comprising a cargo molecule (such as at least 1, 2, 3, 4, 5, or more cargo molecules) and an assembly molecule, coated with b) a peptide, wherein the peptide comprises (including for example consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, there is provided a composition comprising nanoparticles comprising a nucleic acid molecule (such as at least 1, 2, 3, 4, 5, or more nucleic acid molecules) and a peptide, wherein the peptide comprises (including consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the cargo molecule to the peptide in the nanoparticle is about 1:10 to about 1:40 (such as about 1:20 or about 1:40). In some embodiments, the average diameter of the nanoparticles in the composition is no more than about 130 nm. In some embodiments, the absolute zeta potential of the nanoparticles in the composition is no more than about 10 mV. In some embodiments, the polydispersity of the nanoparticles in the composition is no more than about 1.5. In some embodiments, the assembly molecule is a cell penetrating peptide.

In some embodiments, there is provided a composition comprising nanoparticles comprising: a) a core comprising a cargo molecule (such as at least 1, 2, 3, 4, 5, or more cargo molecules) and an assembly molecule, coated with b) a peptide, wherein the peptide comprises (including for example consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, there is provided a composition comprising nanoparticles comprising a nucleic acid molecule (such as at least 1, 2, 3, 4, 5, or more nucleic acid molecules) and a peptide, wherein the peptide comprises (including consisting essentially of or consisting of) an amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWR-SAGWRLWRLWRVRSWSR (SEQ ID NO: 2), KWR-SALYRWRLWRSRSWSR (SEQ ID NO: 3), or KWRSALYRWRLWRSALYSR (SEQ ID NO: 4). In some embodiments, the molar ratio of the cargo molecule to the peptide in the nanoparticle is about 1:10 to about 1:40 (such as about 1:20 or about 1:40). In some embodiments, the average diameter of the nanoparticles in the composition is no more than about 150 nm. In some embodiments, the absolute zeta potential of the nanoparticles in the composition is no more than about 10 mV. In some embodiments, the polydispersity of the nanoparticles in the composition is no more than about 1.5. In some embodiments, the assembly molecule is a cell penetrating peptide (such as CADY or VEPEP-6). In the some embodiments, the assembly molecule is a peptide comprising (including for example consisting essentially of or consisting of) an amino acid sequence $X_1$KWRS$X_2X_3X_4$RWRLWR$X_5X_6X_7X_8$SR (SEQ ID NO: 1), wherein $X_1$ is any amino acid or none, and wherein $X_2$-$X_8$ are any amino acid. The assembly molecule at the core can be the same or different than the peptide in the coating.

In some embodiments, there is provided a composition comprising nanoparticles comprising: a) a core comprising a cargo molecule (such as at least 1, 2, 3, 4, 5, or more cargo molecules) and a peptide, coated with b) a surface layer, wherein the peptide comprises (including for example consisting essentially of or consisting of) an amino acid sequence $X_1$KWRS$X_2X_3X_4$RWRLWR$X_5X_6X_7X_8$SR (SEQ ID NO: 1), wherein $X_1$ is any amino acid or none, and wherein $X_2$-$X_8$ are any amino acid. In some embodiments, there is provided a composition comprising nanoparticles comprising a nucleic acid molecule (such as at least 1, 2, 3, 4, 5, or more nucleic acid molecules) and a peptide, wherein the peptide comprises (including consisting essentially of or consisting of) an amino acid sequence $X_1$KWRS$X_2X_3X_4$RWRLWR$X_5X_6X_7X_8$SR (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, there is provided a non-naturally occurring peptide comprising the amino acid sequence of KWR-SAGWRLWRLWRVRSWSR (SEQ ID NO: 2), KWR-SALYRWRLWRSRSWSR (SEQ ID NO: 3), or KWRSALYRWRLWRSALYSR (SEQ ID NO: 4). In some embodiments, the molar ratio of the cargo molecule to the peptide in the nanoparticle is about 1:10 to about 1:40 (such as about 1:20 or about 1:40). In some embodiments, the average diameter of the nanoparticles in the composition is no more than about 130 nm. In some embodiments, the absolute zeta potential of the nanoparticles in the composition is no more than about 10 mV. In some embodiments, the polydispersity of the nanoparticles in the composition is no more than about 1.5. In some embodiments, the surface layer comprises a cell penetrating peptide (such as CADY or VEPEP-6).

In some embodiments, a complex or nanoparticle as described above comprises a targeting moiety, wherein the targeting moiety is a ligand capable of cell-specific and/or nuclear targeting. A cell membrane surface receptor and/or cell surface marker is a molecule or structure which can bind said ligand with high affinity and preferably with high specificity. Said cell membrane surface receptor and/or cell surface marker is preferably specific for a particular cell, i.e. it is found predominantly in one type of cell rather than in another type of cell (e.g. galactosyl residues to target the asialoglycoprotein receptor on the surface of hepatocytes). The cell membrane surface receptor facilitates cell targeting and internalization into the target cell of the ligand (e.g. the targeting moiety) and attached molecules (e.g. the complex or nanoparticle of the invention). A large number of ligand moieties/ligand binding partners that may be used in the context of the present invention are widely described in the literature. Such a ligand moiety is capable of conferring to the complex or nanoparticle of the invention the ability to bind to a given binding-partner molecule or a class of binding-partner molecules localized at the surface of at least one target cell. Suitable binding-partner molecules include without limitation polypeptides selected from the group consisting of cell-specific markers, tissue-specific markers, cellular receptors, viral antigens, antigenic epitopes and tumor-associated markers. Binding-partner molecules may moreover consist of or comprise one or more sugar, lipid, glycolipid or antibody molecules. According to the invention, a ligand moiety may be for example a lipid, a glycolipid, a hormone, a sugar, a polymer (e.g. PEG, polylysine, PET), an oligonucleotide, a vitamin, an antigen, all or part of a lectin, all or part of a polypeptide, such as for example JTS1 (WO 94/40958), an antibody or a fragment thereof, or a combination thereof. In some embodiments, the ligand moiety used in the present invention is a peptide or polypeptide having a minimal length of 7 amino acids. It is either a native polypeptide or a polypeptide derived from a native polypeptide. "Derived" means containing (a) one or more modifications with respect to the native sequence (e.g. addition, deletion and/or substitution of one or more residues), (b) amino acid analogs, including non-naturally occurring amino acids, (c) substituted linkages, or (d) other modifications known in the art. The polypeptides serving as ligand moiety encompass variant and chimeric polypeptides obtained by fusing sequences of various origins, such as for example a humanized antibody which combines the variable region of a mouse antibody and the constant region of a human immunoglobulin. In addition, such polypeptides may have a linear or cyclized structure (e.g. by flanking at both extremities a polypeptide ligand by cysteine residues). Additionally, the polypeptide in use as a ligand moiety may include modifications of its original structure by way of substitution or addition of chemical moieties (e.g. glycosylation, alkylation, acetylation, amidation, phosphorylation, addition of sulfhydryl groups and the like). The invention further contemplates modifications that render the ligand moiety detectable. For this purpose, modifications with a detectable moiety can be envisaged (i.e. a scintigraphic, radioactive, or fluorescent moiety, or a dye label and the like). Such detectable labels may be attached to the ligand moiety by any conventional techniques and may be used for diagnostic purposes (e.g. imaging of tumoral cells). In some embodiments, the binding-partner molecule is an antigen (e.g. a target cell-specific antigen, a disease-specific antigen, an antigen specifically expressed on the surface of engineered target cells) and the ligand moiety is an antibody, a fragment or a minimal recognition unit thereof (e.g. a fragment still presenting an antigenic specificity) such as those described in detail in immunology manuals (see for example Immunology, third edition 1993, Roitt, Brostoff and Male, ed Gambli, Mosby). The ligand moiety may be a monoclonal antibody. Many monoclonal antibodies that bind many of these antigens are already known, and using techniques known in the art in relation to monoclonal antibody technology, antibodies to most antigens may be prepared. The ligand moiety may be a part of an antibody (for example a Fab fragment) or a synthetic antibody fragment (for example, ScFv). In some embodiments, the ligand moiety is selected among antibody fragments, rather than whole antibodies. Effective functions of whole antibodies, such as complement binding, are removed. ScFv and dAb antibody fragments may be expressed as a fusion with one or more other polypeptides. Minimal recognition units may be derived from the sequence of one or more of the complementary-determining regions (CDR) of the Fv fragment. Whole antibodies, and F(ab')2 fragments are "bivalent". By "bivalent" it is meant that said antibodies and F(ab')2 fragments have two antigen binding sites. In contrast, Fab, Fv, ScFv, dAb fragments and minimal recognition units are monovalent, having only one antigen binding sites. In some embodiments, the ligand moiety allows targeting to a tumor cell and is capable of recognizing and binding to a molecule related to the tumor status, such as a tumor-specific antigen, a cellular protein differentially or over-expressed in tumor cells or a gene product of a cancer-associated vims. Examples of tumor-specific antigens include but are not limited to MUC-1 related to breast cancer (Hareuven i et al., 990, Eur. J. Biochem 189, 475-486), the products encoded by the mutated BRCA1 and BRCA2 genes related to breast and ovarian cancers (Miki et al, 1994, Science 226, 66-7 1; Fuireal et al, 1994, Science 226, 120-122; Wooster et al., 1995, Nature 378, 789-792), APC related to colon cancer (Poiakis, 1995, Curr. Opin. Genet. Dev. 5, 66-71), prostate specific antigen (PSA) related to prostate cancer, (Stamey et al., 1987, New England J. Med. 317, 909), carcinoma embryonic antigen (CEA) related to colon cancers (Schrewe et al., 1990, Mol. Cell. Biol. 10, 2738-2748), tyrosinase related to melanomas (Vile et al, 1993, Cancer Res. 53, 3860-3864), receptor for melanocyte-stimulating hormone (MSH) which is highly expressed in melanoma cells, ErbB-2 related to breast and pancreas cancers (Harris et al., 1994, Gene Therapy 1, 170-175), and alpha-foetoprotein related to liver cancers (Kanai et al., 1997, Cancer Res. 57, 46 1-465). In some embodiments, the ligand moiety is a fragment of an antibody capable of recognizing and binding to the MUC-1 antigen and thus targeting MUC-1 positive tumor cells. In some embodiments, the ligand moiety is the scFv fragment of the SM3 monoclonal antibody which recognizes the tandem repeat region of the MUC-1 antigen (Burshell et al., 1987, Cancer Res. 47, 5476-5482; Girling et al., 1989, Int. J. Cancer 43, 1072-1076; Dokumo et al., 1998, J. Mol. Biol. 284, 713-728). Examples of cellular proteins differentially or overexpressed in tumor cells include but are not limited to the receptor for interleukin 2 (IL-2) overexpressed in some lymphoid tumors, GRP (Gastrin Release Peptide) overexpressed in lung carcinoma cells, pancreas, prostate and stomach tumors (Michael et al., 1995, Gene Therapy 2, 660-668), TNF (Tumor Necrosis Factor) receptor, epidermal growth factor receptors, Fas receptor, CD40 receptor, CD30 receptor, CD27 receptor, OX-40, α-v integrins (Brooks et al, 994, Science 264, 569) and receptors for certain angiogenic growth factors (Hanahan, 1997, Science 277, 48). Based on these indications, it is within the scope of those skilled in the art to define an appropriate ligand moiety capable of recognizing and binding to such proteins. To illustrate, IL-2 is a suitable ligand moiety to bind to TL-2 receptor. In the case of receptors that are specific to fibrosis and inflammation, these include the TGFbeta receptors or the Adenosine receptors that are identified above and are suitable targets for invention compositions. Cell surface markers for multiple myeloma include, but are not limited to, CD56, CD40, FGFR3, CS1, CD138, IGF1R, VEGFR, and CD38, and are suitable targets for invention compositions. Suitable ligand moieties that bind to these cell surface markers include, but are not limited to, anti-CD56, anti-CD40, PRO-001, Chir-258, HuLuc63, anti-CD138-DM1, anti-IGF1R and bevacizumab.

Cargo Molecules

In some embodiments, the cargo molecule of the complex or nanoparticle as described above is a nucleic acid. In some embodiments, the cargo molecule is selected from the group consisting of oligonucleotides, polynucleotides, single- or double-stranded oligo and polynucleotides, antisense oligonucleotides, various forms of RNAi, including for example siRNA, shRNA, etc., microRNA (miRNA), antagomirs, ribozymes, aptamers, plasmid DNA, etc. and suitable combinations of one or more thereof. In some embodiments, the cargo molecule is a protein, such as for example an enzyme or antibody, or a small molecule. In some embodiments, nanoparticle comprises a plurality of cargo molecules that comprise a combination of nucleic acids with proteins or small molecules. In some embodiments, the combination comprises nucleic acids with proteins or small molecules that are covalently attached to each other. In some embodiments, the combination comprises nucleic acids with proteins or small molecules that are not covalently attached to each other.

"Polynucleotide," or "nucleic acid," as used interchangeably herein, refers to polymers of nucleotides of any length, and includes DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, RNA, viral RNA (vRNA), and combinations thereof. Nucleic acids include nucleic acids containing known nucleotide analogs or modified backbone residues or linkages, including for example locked nucleic acid (LNA), unlocked nucleic acid (UNA), and zip nucleic acid (ZNA), which can be synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer e al., Nucleic Acid Res., 19:5081 (1991); Ohtsuka et a., j. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylases, and alkylhalides. "Oligonucleotide," as used herein, generally refers to short, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

In some embodiments, the nucleic acids are single stranded oligonucleotides. In some embodiments, the nucleic acids are double stranded oligonucleotides. The nucleic acids described herein may be any of a range of length of up to, but not necessarily 200 nucleotides in the case of antisense oligonucleotides, RNAi, siRNA, shRNA, iRNA, antagomirs or up to 1000 kilo bases in the case of plasmid DNA.

In some embodiments, the nucleic acids are interference RNA, such as siRNA or shRNA. The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence, interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Interfering RNA includes "small-interfering RNA" or "siRNA," e.g., interfering RNA of about 15-60, 15-50, or 5-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 5-30, 5-25, or 19-25 base pairs in length, preferably about 8-22, 9-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. Preferably, siRNA are chemically synthesized. siRNA can also be generated by cleavage of longer dsRNA (e.g., dsRNA greater than about 25 nucleotides in length) with the E coli RNase III or Dicer. These enzymes process the dsRNA into biologically active siRNA (see, e.g., Yang et al., Proc Natl. Acad. Set. USA, 99:9942-9947 (2002); Calegari et al., Proc. Natl. Acad. Sci. USA, 99: 14236 (2002); Byrom et al., Ambion TeehNotes, 10(1):4-6 (2003); Kawasaki et al., Nucleic Acids Res., 3 1:981-987 (2003); Knight et al., Science, 293:2269-2271 (2001); and Robertson et al., J. Biol. Chem., 243:82 (1968)). Preferably, dsRNA are at least 50 nucleotides to about 100, 200, 300, 400, or 500 nucleotides in length A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops). A small hairpin RNA or short hairpin RNA (shRNA) is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. Suitable length of the interference RNA are about 5 to about 200 nucleotides, or 10-50 nucleotides or base pairs or 15-30 nucleotides or base pairs. In some embodiments, the interference RNA is substantially complementary (such as at least about 60%, 70%, 80%, 90%, 95%, 98%, 99%, or more identical to) the corresponding target gene. In some embodiments, the interference RNA is modified, for example by incorporating non-naturally occurring nucleotides.

In some embodiments, the nucleic acids are double-stranded antisense RNA. Suitable length of the interference RNA are about 5 to about 200 nucleotides, or 10-50 nucleotides or base pairs or 15-30 nucleotides or base pairs n some embodiments, the interference RNA is substantially complementary (such as at least about 60%, 70%, 80%, 90%, 95%, 98%, 99%, or more identical) to the corresponding target gene. In some embodiments, the antisense RNA is modified, for example by incorporating non-naturally occurring nucleotides.

In some embodiments, the nucleic acid is an interfering RNA, such as an siRNA, that specifically targets an RNA molecule, such as an mRNA, encoding a protein involved in a disease, such as cancer. In some embodiments, the disease is cancer, such as a solid tumor or hematological malignancy, and the interfering RNA targets mRNA encoding a protein involved in the cancer, such as a protein involved in regulating the progression of the cancer.

In some embodiments, the nucleic acid is an interfering RNA, such as an siRNA, that specifically targets an RNA molecule, such as an mRNA, encoding a protein involved in negatively regulating an immune response. In some embodiments, the interfering RNA targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4.

In some embodiments, the nucleic acids are miRNA. A microRNA (abbreviated miRNA) is a short ribonucleic acid (RNA) molecule found in eukaryotic cells. A microRNA molecule has very few nucleotides (an average of 22) compared with other RAs. miRNAs are post-transcriptional regulators that bind to complementary sequences on target messenger RNA transcripts (mRNAs), usually resulting in translational repression or target degradation and gene silencing. The human genome may encode over 1000 miRNAs, which may target about 60% of mammalian genes and are abundant in many human cell types. Suitable length of the miRNAs are about 5 to about 200 nucleotides, or 0-50 nucleotides or base pairs or 15-30 nucleotides or base pairs. In some embodiments, the miRNA s substantially complementary (such as at least about 60%, 70%, 80%, 90%, 95%, 98%, 99%, or more identical to) the corresponding target gene. n some embodiments, the antisense RNA is modified, for example by incorporating non-naturally occurring nucleotides.

In some embodiments, the nucleic acids are plasmid DNA or DNA fragments (for example DNA fragments of lengths of up to about 1000 bp). In addition, the plasmid DNA or DNA fragments may be hypermethylated or hypomethylated. In some embodiments, the plasmid DNA or DNA fragments encode one or more genes, and may contain regulatory elements necessary for the expression of said one or more genes. In some embodiments, the plasmid DNA or DNA fragments may comprise one or more genes that encode a selectable marker, allowing for maintenance of the plasmid DNA or DNA fragment in an appropriate host cell.

In some embodiments, the plasmid DNA comprises a DNA sequence encoding a chimeric antigen receptor (CAR) comprising an extracellular antigen-binding domain that specifically binds to a target antigen, a transmembrane domain, and an intracellular signaling domain. CARs are described, for example, in U.S. Pat. No. 8,822,647, U.S. Patent Application Publication No. 2015/0051266, WO 2014/127261, and WO2014099671, the disclosures of which are specifically incorporated herein by reference in their entirety. In some embodiments, the target antigen is an antigen specifically associated with (such as expressed by) a cancer cell. For example, in some embodiments, the plasmid DNA comprises a DNA sequence encoding a CAR comprising an extracellular antigen-binding domain that specifically binds to a cancer-associated antigen, a transmembrane domain, and an intracellular signaling domain. In some embodiments, the cancer-associated antigen is associated with a solid tumor. In some embodiments, the cancer-associated antigen is associated with a hematological malignancy, such as a B cell malignancy or leukemia. In some embodiments, the target antigen includes, for example, CD19, CD20, CD28, OX40, GITR, CD137, CD27, HVEM, BCMA, CD70, CD74, CD38, CD138, CD33, Lewis-Y, CD123, CD44v6 and CS1.

Thus, in some embodiments, the plasmid DNA comprises a DNA sequence encoding a CAR comprising an extracellular antigen-binding domain that specifically binds to a cancer-associated antigen associated with a hematological malignancy, a transmembrane domain, and an intracellular signaling domain. In some embodiments, the hematological malignancy is a B cell malignancy, and the cancer-associated antigen includes, for example, CD19, CD20, CD28, OX40, GITR, CD137, CD27, and HVEM. In some embodiments, the hematological malignancy is leukemia, such as acute myeloid leukemia, and the cancer-associated antigen includes, for example, BCMA, CD70, CD74, CD38, CD138, CD33, Lewis-Y, CD123, CD44v6 and CS1.

Compositions

In some embodiments, there is provided a composition comprising a complex or nanoparticle as described above. In some embodiments, the composition is a pharmaceutical composition comprising a complex or nanoparticle as described above and a pharmaceutically acceptable diluent, excipient and/or carrier. In some embodiments, the concentration of the complex or nanoparticle in the composition is from about 1 nM to about 100 mM, including for example from about 10 nM to about 50 mM, from about 25 nM to about 25 mM, from about 50 nM to about 10 mM, from about 100 nM to about 1 mM, from about 500 nM to about 750 µM, from about 750 nM to about 500 µM, from about 1 µM to about 250 µM, from about 10 µM to about 200 µM, and from about 50 µM to about 150 µM.

The term "pharmaceutically acceptable diluent, excipient, and/or carrier" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals. The term diluent, excipient, and/or "carrier" refers to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting, bulking, emulsifying agents, or pH buffering agents. These compositions can take the form of solutions, suspensions, emulsion, sustained release formulations and the like. Examples of suitable pharmaceutical diluent, excipient, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

In some embodiments, a pharmaceutical composition as described above is formulated for intravenous, intratumoral, intraarterial, topical, intraocular, ophthalmic, intracranial, intrathecal, intravesicular, intradermal, subcutaneous, intramuscular, intranasal, intratracheal, pulmonary, intracavity, or oral administration.

In some embodiments, dosages of the pharmaceutical compositions of the present invention found to be suitable for treatment of human or mammalian subjects are in the range of 0.001 mg/kg-100 mg/kg of the cargo molecule. In some embodiments, dosage ranges are 0.1-20 mg/kg. In some embodiments, dosage ranges are in the range of 0.5-10 mg/kg. In some embodiments, the schedule of administration of the pharmaceutical composition to an individual ranges from a single administration that constitutes the entire treatment to daily administration. In some embodiments, the administration is once every 3-30 days. In some embodiments, the administration is once every 4-7 days.

In some embodiments, there is provided a pharmaceutical composition comprising a complex or nanoparticle as described above and a pharmaceutically acceptable carrier, wherein the pharmaceutically acceptable carrier is a sugar or a protein. In some embodiments, the sugar is selected from the group consisting of sucrose, glucose, mannitol, and a combination thereof, and is present in the pharmaceutical composition at a concentration from about 5% to about 20%. In some embodiments, the sugar is sucrose. In some embodiments, the sugar is glucose. In some embodiments, the sugar is mannitol. In some embodiments, the protein is albumin. In some embodiments, the albumin is human serum albumin. In some embodiments, the pharmaceutical composition is lyophilized.

Methods of Preparation

In some embodiments, there is provided a method of preparing a complex or nanoparticle as described above comprising a) combining a composition comprising an ADGN peptide as described above with a composition comprising a cargo molecule as described above to form a mixture, and b) incubating the mixture to form the complex or nanoparticle. In some embodiments, the composition comprising the ADGN peptide is a stock solution comprising the ADGN peptide at a concentration from about 0.1 mg/ml to about 10 mg/ml, including for example from about 0.2 mg/ml to about 5 mg/ml, from about 0.5 mg/ml to about 2.5 mg/ml, from about 0.75 mg/ml to about 1.5 mg/ml, and about 1 mg/ml. In some embodiments, the stock solution comprising the ADGN peptide is sonicated for from about 2 min to about 20 min, including for example from about 5 min to about 15 min, and about 10 min. In some embodiments, the cargo molecule is a nucleic acid, and the composition comprising the cargo molecule is a stock solution comprising a nucleic acid. In some embodiments, the nucleic acid is an oligonucleotide as described above, and the stock solution comprising a nucleic acid comprises the oligonucleotide at a concentration from about 1 µM to about 20 µM, including for example from about 2 µM to about 15 µM, from about 3 µM to about 10 µM, from about 4 µM to about 8 µM, and about 5 µM. In some embodiments, the stock solution comprising an oligonucleotide is formulated in water. In some embodiments, the water is distilled water. In some embodiments, the stock solution comprising an oligonucleotide is formulated in a buffer. In some embodiments, the nucleic acid is a plasmid, and the stock solution comprising the nucleic acid comprises the plasmid at a concentration from about 20 µM to about 500 µM, including for example from about 30 µM to about 400 µM, from about 40 µM to about 300 µM, from about 50 µM to about 200 µM, from about 75 µM to about 150 µM, and about 100 µM. In some embodiments, the stock solution comprising a plasmid is formulated in water. In some embodiments, the water is distilled water. In some embodiments, the stock solution comprising a plasmid is formulated in a buffer. In some embodiments, the buffer is any buffer known in the art used for storing a plasmid, including for example a buffer comprising Tris and EDTA, wherein the Tris is at a concentration from about 10 mM to about 100 mM, including for example from about 20 mM to about 80 mM, from about 30 mM to about 70 mM, from about 40 mM to about 60 mM, and about 50 mM, and wherein the EDTA is at a concentration from about 0.1 mM to about 1 mM, including for example from about 0.2 mM to about 0.8 mM, from about 0.3 mM to about 0.7 mM, from about 0.4 mM to about 0.6 mM, and about 0.5 mM. In some embodiments, the method comprises combining the stock solution comprising an ADGN peptide and the stock solution comprising a nucleic acid in an aqueous medium to form a mixture. In some embodiments, the aqueous medium is water, including for example distilled water. In some embodiments, the aqueous medium is a buffer, including for example PBS, Tris, or any buffer known in the art for stabilizing nucleoprotein complexes. In some embodiments, the molar ratio of the ADGN peptide to the nucleic acid in the mixture is from about 1:5 to about 80:1, including for example from about 5:1 to about 40:1, and about any of 1:2, 1:1, 2:1, 5:1, 10:1, 20:1, 30:1, 40:1 and 50:1. In some embodiments, the mixture is incubated to form the complex or nanoparticle for from about 10 min to 60 min, including for example for about any of 20 min, 30 min, 40 min, and 50 min, at a temperature from about 2° C. to about 50° C., including for example from about 2° C. to about 5° C., from about 5° C. to about 10° C., from about 10° C. to about 15° C., from about 15° C. to about 20° C., from about 20° C. to about 25° C., from about 25° C. to about 30° C., from about 30° C. to about 35° C., from about 35° C. to about 40° C., from about 40° C. to about 45° C., and from about 45° C. to about 50° C., thereby resulting in a stock solution comprising the complex or nanoparticle. In some embodiments, the stock solution comprising the complex or nanoparticle remains stable for at least about three weeks, including for example for at least about any of 6 weeks, 2 months, 3 months, 4 months, 5 months, and 6 months at 4° C. In some embodiments, the stock solution comprising the complex or nanoparticle is lyophilized in the presence of a carrier. In some embodiments, the carrier is a sugar, including for example, sucrose, glucose, mannitol and combinations thereof, and is present in the stock solution comprising the complex or nanoparticle at from about 5% to about 20%, including for example from about 7.5% to about 17.5%, from about 10% to about 15%, and about 12.5%, weight per volume. In some embodiments, the carrier is a protein, including for example albumin, such as human serum albumin.

In some embodiments, there is provided a method of preparing a nanoparticle comprising a core and at least one additional layer as described above, comprising a) combining a composition comprising an assembly molecule as described above with a composition comprising a cargo molecule as described above to form a first mixture, b) incubating the first mixture to form the core of the nanoparticle, c) combining the mixture of b) with a composition comprising a cell-penetrating peptide to form a second mixture, and d) incubating the second mixture to form a nanoparticle comprising a core and at least one additional layer. In some embodiments, the method further comprises e) combining a composition comprising a nanoparticle comprising a core and at least one additional layer and a composition comprising a cell-penetrating peptide to form a third mixture, and f) incubating the third mixture to form a nanoparticle comprising a core and at least two additional layers. It is to be appreciated that the method can be adapted to form a nanoparticle comprising increasing numbers of layers. In some embodiments, the assembly molecule is an ADGN peptide as described above. In some embodiments, the assembly molecule is not an ADGN peptide as described above. In some embodiments, the cell-penetrating peptide is an ADGN peptide as described above. In some embodiments, the cell-penetrating peptide is not an ADGN peptide as described above. In some embodiments, the composition comprising the assembly molecule or cell-penetrating peptide is a stock solution comprising the assembly molecule or cell-penetrating peptide at a concentration from about 0.1 mg/ml to about 10 mg/ml, including for example from about 0.2 mg/ml to about 5 mg/ml, from about 0.5 mg/ml to about 2.5 mg/ml, from about 0.75 mg/ml to about 1.5 mg/ml, and about 1 mg/ml. In some embodiments, the stock solution comprising the assembly molecule or cell-penetrating peptide is sonicated for from about 2 min to about 20 min, including for example from about 5 min to about 15 min, and about 10 min. In some embodiments, the cargo molecule is a nucleic acid, and the composition comprising the cargo molecule is a stock solution comprising a nucleic acid. In some embodiments, the nucleic acid is an oligonucleotide as described above, and the stock solution comprising a nucleic acid comprises the oligonucleotide at a concentration from about 1 µM to about 20 µM, including for example from about 2 µM to about 15 µM, from about 3 µM to about 10 µM, from about 4 µM to about 8 µM, and about 5 µM. In some embodiments, the stock solution comprising an oligonucleotide is formulated in water. In some embodiments, the water is distilled water. In some embodiments, the stock solution comprising an oligonucleotide is formulated in a buffer. In some embodiments, the nucleic acid is a plasmid, and the stock solution comprising the nucleic acid comprises the plasmid at a concentration from about 20 µM to about 500 µM, including for example from about 30 µM to about 400 µM, from about 40 µM to about 300 µM, from about 50 µM to about 200 µM, from about 75 µM to about 150 µM, and about 100 µM. In some embodiments, the stock solution comprising a plasmid is formulated in water. In some embodiments, the water is distilled water. In some embodiments, the stock solution comprising a plasmid is formulated in a buffer. In some embodiments, the buffer is any buffer known in the art used for storing a plasmid, including for example a buffer comprising Tris and EDTA, wherein the Tris is at a concentration from about 10 mM to about 100 mM, including for example from about 20 mM to about 80 mM, from about 30 mM to about 70 mM, from about 40 mM to about 60 mM, and about 50 mM, and wherein the EDTA is at a concentration from about 0.1 mM to about 1 mM, including for example from about 0.2 mM to about 0.8 mM, from about 0.3 mM to about 0.7 mM, from about 0.4 mM to about 0.6 mM, and about 0.5 mM. In some embodiments, the combining is performed in an aqueous medium to form a mixture. In some embodiments, the aqueous medium is water, including for example distilled water. In some embodiments, the aqueous medium is a buffer, including for example PBS, Tris, or any buffer known in the art for stabilizing nucleoprotein complexes. In some embodiments, the molar ratio of the cell-penetrating peptide to the nucleic acid in the mixture is from about 1:5 to about 80:1, including for example from about 5:1 to about 40:1, and about any of 1:2, 1:1, 2:1, 5:1, 10:1, 20:1, 30:1, 40:1 and 50:1. In some embodiments, the mixture is incubated to form the nanoparticle for from about 10 min to 60 min, including for example for about any of 20 min, 30 min, 40 min, and 50 min, at a temperature from about 30° C. to about 45° C., including for example at about any of 31° C., 32° C., 33° C., 34° C., 35° C., 36° C., 37° C., 38° C., 39° C., 40° C., 41° C., 42° C., 43° C., and 44° C., thereby resulting in a stock solution comprising the nanoparticle. In some embodiments, the stock solution comprising the nanoparticle remains stable for at least about three weeks at 4° C. In some embodiments, the stock solution comprising the nanoparticle is lyophilized in the presence of a carrier. In some embodiments, the carrier is a sugar, including for example, sucrose, glucose, mannitol and combinations thereof, and is present in the stock solution comprising the complex or nanoparticle at from about 5% to about 20%, including for example from about 7.5% to about 17.5%, from about 10% to about 15%, and about 12.5%, weight per volume. In some embodiments, the carrier is a protein, including for example albumin, such as human serum albumin.

In some embodiments, for a stable composition comprising a complex or nanoparticle of the invention, the average diameter of the complex does not change by more than about 10%, and the polydispersity index does not change by more than about 10%.

Methods of Use

In some embodiments, there is provided a method of treating a disease in an individual comprising administering to the individual an effective amount of a pharmaceutical composition comprising a complex or nanoparticle as described above and a pharmaceutically acceptable carrier. In some embodiments, the complex or nanoparticle comprises one or more cargo molecules useful for the treatment of the disease. In some embodiments, the disease to be treated includes, but is not limited to, cancer, diabetes, inflammatory diseases, fibrosis, viral infectious diseases, hereditary diseases, and aging and degenerative diseases. In some embodiments, the pharmaceutical composition modulates the expression of one or more genes. In some embodiments, the one or more genes encode proteins including, but not limited to, growth factors and cytokines, cell surface receptors, signaling molecules and kinases, transcription factors and other modulators of transcription, regulators of protein expression and modification, and regulators of apoptosis and metastasis. In some embodiments, the pharmaceutical composition further comprises one or more additional complexes or nanoparticles as described above. In some embodiments, the method further comprises administering to the individual an effective amount of one or more additional pharmaceutical compositions comprising one or more additional complexes or nanoparticles as described above.

"Modulation" of activity or expression used herein means regulating or altering the status or copy numbers of a gene or mRNA or changing the amount of gene product such as a protein that is produced. In some embodiments, the cargo molecule inhibits the expression of a target gene. In some embodiments, the modulation (such as inhibition) occurs at a post-transcriptional level in some embodiments, the cargo molecule inhibits the expression of the gene or gene product by at least about any of 0%, 20%, 30%, 40%, 60%, 70%, 80%, 90%, or 100%. In some embodiments, such as in the case of plasmid delivery, the cargo molecule may increase the expression of a gene or gene product by at least about any of 10%, 20%, 30%, 40%, 60%, 70%, 80%, 90%, or 100%.

In some embodiments of the methods described above, the one or more genes include, but are not limited to, EGF, VEGF, FGF, HGF, HDGF, IGF, PDGF, TGF-α, TGF-0, TNF-α, wnt, ER, PR, Her2, Her3, angiopoietin receptor, EGFR, FGFR, HGFR, HDGFR, IGFR, KGFR, MSFR, PDGFR, TGFR, VEGFR1, VEGFR2, VEGFR3, Frizzled family receptors (FZD-1 to 10), smoothened, patched, CXCR4, KRAS, NRAS, RAF, MEK, MEKK, MAPK, MKK, ERK, JNK, JAK, PKA, PKC, PI3K, Akt, mTOR, Raptor, Rictor, MLST8, PRAS40, DEPTOR, MSIN1, S6 kinase, PDK1, BRAF, FAK, Src, Fyn, Shc, GSK, IKK, PLK-1, cyclin-dependent kinases (Cdk1 to 13), CDK-activating kinases, ALK/Met, Syk, BTK, Bcr-Abl, RET, β-catenin, Mel-1, PKN, ATF-2, Chop, c-Jun, c-Myc, DPC4, Elk-1, Ets1, Max, MEF2C, NFAT4, Sap1a, STATs, Tal, p53, CREB, Myc, NF-κB, HDACs, HIF-1α, RRM2, ubiquitin ligase, LMP2, LMP7, MECL-1, XIAP, Bcl-2, osteopontin, SPARC, MMP-2, MMP-9, uPAR, IL-2, IL-12, interferon-gamma, GM-CSF, B7-1, caspase-9, p53, MUC-1, MDR-1, HLA-B7/Beta 2-Microglobulin, Her2, Hsp27, thymidine kinase, and MDA-7, GLI1, CTNNB1, eIF5A, mutant DDX3X, Hexokinase II, histone methyltransferase EZH2, ARK5, ALK, MUC1, HMGA2, IRF1, RPN13, HDAC11, Rad51, Spry2, mir-146a, mir-146b, survivin, MDM2, MCL1, CMYC, XBP1 (spliced and unspliced), SLAMF7, CS1, Erbb4, Cxcr4 (waldenstroms macroglobulinemia), Myc, Bcl2, Prdx1 and Prdx2 (burkitts lymphoma), Bcl6, Idh1, Idh2, Smad, Ccnd2, Cyclin d1-2, B7-h1 (pdl-1), Pyk2, RSV nucleocapsid, Pre-gen/Pre-C, Pre-S1, Pre-S2/S, X, HBV conserved sequences, HIV Tat, HIV TAR RNA, human CCR5, miR-122, EBOV polymerase L, VP24, VP40, GP/sGP, VP30, VP35, NPC1, TIM-1, Transthyretin, MDS1-EVI1, PRDM16, SETBP1, ß-Globin, LPL, keratin K6A, keratin K6B, keratin 16, keratin 17, p53, ß-2 adrenergic receptors (ADRB2), TRPV1, VEGF, VEGFR, HIF-1, caspase-2, SPARC, CTGF, TGFβ1, TGFβ receptors 1, TGFβ receptors 2, TGFβ receptors 3, VEGF, Angiotensin II, TIMP, HSP47, thrombospondin, CCN1, LOXL2, MMP2, MMP9, CCL2, Adenosine receptor A2A, Adenosine receptor A2B, Adenylyl cyclase, Smad 3, Smad 4, Smad 7, SOX9, arrestin, PDCD4, PAI-1, NF-κB, and PARP-1.

In some embodiments of the methods described above, the disease to be treated is cancer. In some embodiments, the cancer is a solid tumor, and the pharmaceutical composition modulates the expression of one or more genes that encode proteins including, but not limited to, growth factors and cytokines, cell surface receptors, signaling molecules and kinases, transcription factors and other modulators of transcription, regulators of protein expression and modification, and regulators of apoptosis and metastasis. In some embodiments, the growth factors or cytokines include, but are not limited to, EGF, VEGF, FGF, HGF, HDGF, IGF, PDGF, TGF-α, TGF-β, TNF-α, and wnt. In some embodiments, the cell surface receptors include, but are not limited to, ER, PR, Her2, Her3, angiopoietin receptor, EGFR, FGFR, HGFR, HDGFR, IGFR, KGFR, MSFR, PDGFR, TGFR, VEGFR1, VEGFR2, VEGFR3, Frizzled family receptors (FZD-1 to 10), smoothened, patched, and CXCR4. In some embodiments, the signaling molecules or kinases include, but are not limited to, KRAS, NRAS, RAF, MEK, MEKK, MAPK, MKK, ERK, JNK, JAK, PKA, PKC, PI3K, Akt, mTOR, Raptor, Rictor, MLST8, PRAS40, DEPTOR, MSIN1, S6 kinase, PDK1, BRAF, FAK, Src, Fyn, Shc, GSK, IKK, PLK-1, cyclin-dependent kinases (Cdk1 to 13), CDK-activating kinases, ALK/Met, Syk, BTK, Bcr-Abl, RET, 0-catenin, Mel-1, and PKN3. In some embodiments, the transcription factors or other modulators of transcription include, but are not limited to, ATF-2, Chop, c-Jun, c-Myc, DPC4, Elk-1, Ets1, Max, MEF2C, NFAT4, Sap1a, STATs, Tal, p53, CREB, Myc, NF-κB, HDACs, HIF-1α, and RRM2. In some embodiments, the regulators of protein expression or modification include, but are not limited to, ubiquitin ligase, LMP2, LMP7, and MECL-1. In some embodiments, the regulators of apoptosis or metastasis include, but are not limited to, XIAP, Bcl-2, osteopontin, SPARC, MMP-2, MMP-9, uPAR.

In some embodiments of the methods described above, the disease to be treated is cancer, wherein the cancer is a solid tumor, and the pharmaceutical composition comprises nucleic acid encoding one or more proteins involved in tumor development and/or progression. In some embodiments, the one or more proteins involved in tumor development and/or progression is selected from the group consisting of IL-2, IL-12, interferon-gamma, GM-CSF, B7-1, caspase-9, p53, MUC-1, MDR-1, HLA-B7/Beta 2-Microglobulin, Her2, Hsp27, thymidine kinase, and MDA-7.

In some embodiments of the methods described above, the disease to be treated is cancer, wherein the cancer is a hematological malignancy, and the pharmaceutical composition modulates the expression of one of more genes encoding proteins involved in hematological malignancy development and/or progression. In some embodiments, the proteins involved in hematological malignancy development and/or progression include, but are not limited to, GLI1, CTNNB1, eIF5A, mutant DDX3X, Hexokinase II, histone methyltransferase EZH2, ARK5, ALK, MUC1, HMGA2, IRF, RPN13, HDAC11, Rad51, Spry2, mir-146a, mir-146b, survivin, MDM2, MCL1, CMYC, XBP1 (spliced and unspliced), SLAMF7, CS1, Erbb4, Cxcr4 (waldenstroms macroglobulinemia), Myc, Bcl2, Prdx1 and Prdx2 (burkitts lymphoma), Bcl6, Idh1, Idh2, Smad, Ccnd2, Cyclin d1-2, B7-h1 (pdl-1), and Pyk2.

In some embodiments of the methods described above, the disease to be treated is a viral infectious disease, and the pharmaceutical composition modulates the expression of one or more genes encoding proteins involved in the viral infectious disease development and/or progression. In some embodiments, the proteins involved in the viral infectious disease development and/or progression include, but are not limited to, RSV nucleocapsid, Pre-gen/Pre-C, Pre-S1, Pre-S2/S, X, HBV conserved sequences, HIV Tat, HIV TAR RNA, human CCR5, miR-122, EBOV polymerase L, VP24, VP40, GP/sGP, VP30, VP35, NPC1, and TIM-1.

In some embodiments of the methods described above, the disease to be treated is a hereditary disease, and the pharmaceutical composition modulates the expression of one or more genes encoding proteins involved in the hereditary disease development and/or progression. In some embodiments, the proteins involved in the hereditary disease development and/or progression include, but are not limited to, Transthyretin, MDS1-EVI1, PRDM16, SETBP1, ß-Globin, and LPL.

In some embodiments of the methods described above, the disease to be treated is an aging or degenerative disease, and the pharmaceutical composition modulates the expression of one or more genes encoding proteins involved in the aging or degenerative disease development and/or progression. In some embodiments, the proteins involved in the aging or degenerative disease development and/or progression include, but are not limited to, keratin K6A, keratin K6B, keratin 16, keratin 17, p53, ß-2 adrenergic receptors (ADRB2), TRPV1, VEGF, VEGFR, HIF-1, and caspase-2.

In some embodiments of the methods described above, the disease to be treated is a fibrotic or inflammatory disease, and the pharmaceutical composition modulates the expression of two or more genes encoding proteins involved in the fibrotic or inflammatory disease development and/or progression. In some embodiments, the proteins involved in the fibrotic or inflammatory disease development and/or progression are selected from the group consisting of SPARC, CTGF, TGFβ1, TGFβ receptors 1, TGFβ receptors 2, TGFβ receptors 3, VEGF, Angiotensin II, TIMP, HSP47, thrombospondin, CCN1, LOXL2, MMP2, MMP9, CCL2, Adenosine receptor A2A, Adenosine receptor A2B, Adenylyl cyclase, Smad 3, Smad 4, Smad 7, SOX9, arrestin, PDCD4, PAI-1, NF-κB, and PARP-1.

In some embodiments of the methods described above, the pharmaceutical composition modulates the expression of one or more miRNAs involved in a disease. In some embodiments, the disease includes, but is not limited to, hepatitis B, hepatitis C, polycystic liver and kidney disease, cancer, cardiovascular disease, cardiac failure, cardiac hypertrophy, neurodevelopmental disease, fragile X syndrome, Rett syndrome, Down syndrome, Alzheimer's disease, Huntington's disease, schizophrenia, inflammatory disease, rheumatoid arthritis, systemic lupus erythematosus, psoriasis, and skeletal muscle disease. In some embodiments, the one or more miRNAs include, but are not limited to, miR-122, miR-21, miR-155, miR-23, and miR-191, miR-205, miR-145, miR-10b, and miR-125b, miR-200a, miR-200c, and miR-141, miR-199a, miR-140, miR-145, and miR125b1, miR-205, miR155, miR 200a, 200b, 200c, miR-193a, 193b, miR-let 7g, miR-21, miR-20a, miR-17-19 family, miR 31, miR 135, miR-181b, and miR 200c, miR-34, miR-let7, miR 143, miR 145, miR-133b, miR-126, Has-miR-191, 199a, miR 155, miR-17-5p, miR-173p, miR-18a, miR-19a, miR-19b-1, miR-20a and miR-92a-1, miR-21, miR 150, miR-155, miR-15a, miR16, miR-29, miR143, miR-45, miR-30d, miR-let 7a, miR-181a, miR-1, miR-16, miR-27b, miR-30d, miR-126, miR-133, miR-143, the let-7 family, miR-208, miR-23a, miR-23b, miR-24, miR-195, miR-199a, miR-214, miR-194, miR-192, miR-200c, miR-203, miR-106b-25, miR-15b, miR-16, has-mir-21 and has-mir-205, miR-17-92, has-mir-126□, miR-let 7, hsa-let-7a-2, let-7f-1, miR-2 23, miR-26b, miR-221, miR-103-1, miR-185, miR-23 b, miR-203, miR 17-5p, miR-23, miR-205, miR-29c, miR-26a, miR-30c, miR-30e-5p, miR-146 b, miR-221, miR-222, miR-181b, miR-155, miR-224, miR-30d, miR-125b, miR-26a, miR-30a-5p, miR-23a, miR-23b, miR-24, miR-195, miR-199a, miR-214, miR-99a, let-7c, miR-125b-2, miR-155 and miR-802, miR-9, miR-128a, miR-125b, miR-155, miR-146, miR-189, miR-61, miR-78, miR-21, miR-142-3p, miR 342, miR-299-3p, miR-198, miR-298, miR-196a, miR-17-5p, miR-409-3p, miR-141, miR-383, miR-112, miR-184, miR-203, mIR-132, miR-381, miR-382, miR-107, miR-103, and miR-100.

In some embodiments of the methods described above, the pharmaceutical composition is administered to the individual by any of intravenous, intratumoral, intraarterial, topical, intraocular, ophthalmic, intracranial, intrathecal, intravesicular, intradermal, subcutaneous, intramuscular, intranasal, intratracheal, pulmonary, intracavity, or oral administration.

In some embodiments of the methods described above, the individual is a mammal. In some embodiments, the individual is human.

In some embodiments, there is provided a method of delivering a molecule into a cell comprising contacting the cell with a complex or nanoparticle as described above, wherein the complex or nanoparticle comprises the molecule. In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the cell is a peripheral blood-derived T cell, a central memory T cell, a cord blood-derived T cell, or a hematopoietic stem cell or other precursor cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the molecule is a cargo molecule as described above. In some embodiments, the cargo molecule is selected from the group consisting of nucleic acids, polypeptides, and small molecules. In some embodiments, the cargo molecule is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

Thus, in some embodiments, there is provided a method of delivering a nucleic acid into a cell comprising contacting the cell with a complex or nanoparticle as described above, wherein the complex or nanoparticle comprises the nucleic acid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the nucleic acid to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the nucleic acid is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the nucleic acid is RNA, such as siRNA. In some embodiments, the nucleic acid is DNA, such as plasmid DNA. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the complex or nanoparticle further comprises one or more additional cargo molecules. In some embodiments, the one or more additional cargo molecules are useful for the treatment of the disease.

In some embodiments, there is provided a method of delivering an siRNA into a cell comprising contacting the cell with a complex or nanoparticle as described above, wherein the complex or nanoparticle comprises the siRNA and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the siRNA to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the siRNA is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the delivery of the siRNA into the cell results in decreased expression of a target in the cell. In some embodiments, the expression of the target is decreased by at least about 30% (such as by at least about any of 30, 35, 40, 45, 50, 55, 60, 65, 70, 75, 80, 85, 90, 95%, or more, including any ranges between these values). In some embodiments, the expression of the target remains decreased for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease.

In some embodiments, there is provided a method of delivering a plasmid into a cell comprising contacting the cell with a complex or nanoparticle as described above, wherein the complex or nanoparticle comprises the plasmid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease.

In some embodiments, there is provided a method of delivering a plasmid and an interfering RNA, such as an siRNA, into a cell comprising contacting the cell with a complex or nanoparticle as described above, wherein the complex or nanoparticle comprises the plasmid, interfering RNA, and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the complex or nanoparticle is about 1:10 to about 1:40 (such as about 1:20 or about 1:40) and the molar ratio of the interfering RNA to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the complex or nanoparticle further comprises one or more additional cargo molecules. In some embodiments, the one or more additional cargo molecules are useful for the treatment of the disease.

In some embodiments, there is provided a method of delivering a plasmid and an interfering RNA, such as an siRNA, into a cell comprising contacting the cell with a) a first complex or nanoparticle as described above, wherein the first complex or nanoparticle comprises the plasmid and an ADGN peptide comprising the amino acid sequence $X_1KWRSX_2X_3X_4RWRLWRX_5X_6X_7X_8SR$ (SEQ ID NO: 1); and b) a second complex or nanoparticle as described above, wherein the second complex or nanoparticle comprises the interfering RNA and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the first complex or nanoparticle is about 1:10 to about 1:40 (such as about 1:20 or about 1:40) and the molar ratio of the interfering RNA to the ADGN peptide in the second complex or nanoparticle is about 1:10 to about 1:40 (such as about 1:20 or about 1:40). In some embodiments, the contacting of the cell with the first and second complex or nanoparticle is carried out in vivo. In some embodiments, the contacting of the cell with the first and second complex or nanoparticle is carried out ex vivo. In some embodiments, the contacting of the cell with the first and second complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the first and/or second complex or nanoparticle further comprises one or more additional cargo molecules. In some embodiments, the one or more additional cargo molecules are useful for the treatment of the disease.

In some embodiments, there is provided a method of delivering a polypeptide into a cell comprising contacting the cell with a complex or nanoparticle as described above, wherein the complex or nanoparticle comprises the polypeptide and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the polypeptide to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the polypeptide is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a small molecule into a cell comprising contacting the cell with a complex or nanoparticle as described above, wherein the complex or nanoparticle comprises the small molecule and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the small molecule to the ADGN peptide in the complex or nanoparticle is about 1:10 to about 1:40 (such as about 1:20 or about 1:40). In some embodiments, the contacting of the cell with the complex or nanoparticle is carried out in vivo. In some embodiments, the contacting of the cell with the complex or nanoparticle is carried out ex vivo. In some embodiments, the contacting of the cell with the complex or nanoparticle is carried out in vitro. In some embodiments, the cell is an immune cell, such as a granulocyte, a mast cell, a monocyte, a dendritic cell, a B cell, a T cell, or a natural killer cell. In some embodiments, the T cell is an immortalized T cell, such as a T cell from a T cell line. In some embodiments, the T cell is a primary T cell, such as a T cell of an individual. In some embodiments, the cell is a fibroblast. In some embodiments, the small molecule is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a molecule into a T cell comprising contacting the cell with a complex or nanoparticle as described above, wherein the complex or nanoparticle comprises the molecule and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the molecule to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the molecule is a cargo molecule as described above. In some embodiments, the cargo molecule is selected from the group consisting of nucleic acids, polypeptides, and small molecules. In some embodiments, the cargo molecule is useful for the treatment of a disease, such as any of the diseases to be treated described herein. In some embodiments, the complex or nanoparticle further comprises one or more additional cargo molecules. In some embodiments, the one or more additional cargo molecules are useful for the treatment of the disease.

In some embodiments, there is provided a method of delivering a nucleic acid into a T cell comprising contacting the cell with a complex or nanoparticle as described above, wherein the complex or nanoparticle comprises the nucleic acid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the nucleic acid to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the nucleic acid is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the nucleic acid is RNA, such as siRNA. In some embodiments, the nucleic acid is DNA, such as plasmid DNA. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the complex or nanoparticle further comprises one or more additional cargo molecules. In some embodiments, the one or more additional cargo molecules are useful for the treatment of the disease.

In some embodiments, there is provided a method of delivering siRNA into a T cell comprising contacting the cell with a complex or nanoparticle as described above, wherein the complex or nanoparticle comprises the siRNA and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the siRNA to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the siRNA is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the delivery of the siRNA into the cell results in decreased expression of a target in the cell. In some embodiments, the expression of the target is decreased by at least about 30% (such as by at least about any of 30, 35, 40, 45, 50, 55, 60, 65, 70, 75, 80, 85, 90, 95%, or more, including any ranges between these values). In some embodiments, the expression of the target remains decreased for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease.

In some embodiments, there is provided a method of delivering a plasmid into a T cell comprising contacting the cell with a complex or nanoparticle as described above, wherein the complex or nanoparticle comprises the plasmid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease. In some embodiments, the one or more additional cargo molecules comprise one or more interfering RNAs, such as siRNAs, that specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4.

In some embodiments, there is provided a method of delivering a plasmid and an interfering RNA, such as an siRNA, into a T cell comprising contacting the cell with a complex or nanoparticle as described above, wherein the complex or nanoparticle comprises the plasmid, interfering RNA, and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the complex or nanoparticle is about 1:10 to about 1:40 (such as about 1:20 or about 1:40) and the molar ratio of the interfering RNA to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the complex or nanoparticle further comprises one or more additional cargo molecules. In some embodiments, the one or more additional cargo molecules are useful for the treatment of the disease.

In some embodiments, there is provided a method of delivering a plasmid and an interfering RNA, such as an siRNA, into a T cell comprising contacting the cell with a) a first complex or nanoparticle as described above, wherein the first complex or nanoparticle comprises the plasmid and an ADGN peptide comprising the amino acid sequence $X_1KWRSX_2X_3X_4RWRLWRX_5X_6X_7X_8SR$ (SEQ ID NO: 1); and b) a second complex or nanoparticle as described above, wherein the second complex or nanoparticle comprises the interfering RNA and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the first complex or nanoparticle is about 1:10 to about 1:40 (such as about 1:20 or about 1:40) and the molar ratio of the interfering RNA to the ADGN peptide in the second complex or nanoparticle is about 1:10 to about 1:40 (such as about 1:20 or about 1:40). In some embodiments, the contacting of the T cell with the first and second complex or nanoparticle is carried out in vivo. In some embodiments, the contacting of the T cell with the first and second complex or nanoparticle is carried out ex vivo. In some embodiments, the contacting of the T cell with the first and second complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the first and/or second complex or nanoparticle further comprises one or more additional cargo molecules. In some embodiments, the one or more additional cargo molecules are useful for the treatment of the disease.

In some embodiments, there is provided a method of delivering a polypeptide into a T cell comprising contacting the cell with a complex or nanoparticle as described above, wherein the complex or nanoparticle comprises the polypeptide and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVR-SWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the polypeptide to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the polypeptide is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a small molecule into a T cell comprising contacting the cell with a complex or nanoparticle as described above, wherein the complex or nanoparticle comprises the small molecule and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVR-SWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the small molecule to the ADGN peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the small molecule is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a molecule into a T cell comprising contacting the cell with a complex or nanoparticle as described above, wherein the complex or nanoparticle comprises the molecule and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_1$ is W or none, $X_{12}$ is A, R, or none, and $X_{13}$ is W or F, and wherein if $X_3$ is none, then $X_2$, $X_1$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the molecule to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the molecule is a cargo molecule as described above. In some embodiments, the cargo molecule is selected from the group consisting of nucleic acids, polypeptides, and small molecules. In some embodiments, the cargo molecule is useful for the treatment of a disease, such as any of the diseases to be treated described herein. In some embodiments, the complex or nanoparticle further comprises one or more additional cargo molecules. In some embodiments, the one or more additional cargo molecules are useful for the treatment of the disease.

In some embodiments, there is provided a method of delivering a nucleic acid into a T cell comprising contacting the cell with a complex or nanoparticle as described above, wherein the complex or nanoparticle comprises the nucleic acid and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_{11}$ is W or none, $X_{12}$ is A, R, or none, and $X_{13}$ is W or F, and wherein if $X_3$ is none, then $X_2$, $X_1$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the nucleic acid to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the nucleic acid is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the nucleic acid is RNA, such as siRNA. In some embodiments, the nucleic acid is DNA, such as plasmid DNA. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the complex or nanoparticle further comprises one or more additional cargo molecules. In some embodiments, the one or more additional cargo molecules are useful for the treatment of the disease.

In some embodiments, there is provided a method of delivering siRNA into a T cell comprising contacting the cell with a complex or nanoparticle as described above, wherein the complex or nanoparticle comprises the siRNA and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_1$ is W or none, $X_{12}$ is A, R, or none, and $X_{13}$ is W or F, and wherein if $X_3$ is none, then $X_2$, $X_{11}$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the siRNA to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the siRNA is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the delivery of the siRNA into the cell results in decreased expression of a target in the cell. In some embodiments, the expression of the target is decreased by at least about 30% (such as by at least about any of 30, 35, 40, 45, 50, 55, 60, 65, 70, 75, 80, 85, 90, 95%, or more, including any ranges between these values). In some embodiments, the expression of the target remains decreased for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease.

In some embodiments, there is provided a method of delivering a plasmid into a T cell comprising contacting the cell with a complex or nanoparticle as described above, wherein the complex or nanoparticle comprises the plasmid and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_{11}$ is W or none, $X_{12}$ is A, R, or none, and $X_{13}$ is W or F, and wherein if $X_3$ is none, then $X_2$, $X_{11}$, and $X_{12}$ are none as well. In some embodiments, the VEPEP-9 peptide comprises the amino acid sequence of LRWWLRWASRWFSR- WAWWR (SEQ ID NO: 26), LRWWLRWASRWASR-WAWFR (SEQ ID NO: 27), or RWWLRWASRWALSWRWWR (SEQ ID NO: 28). In some embodiments, the molar ratio of the plasmid to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease.

In some embodiments, there is provided a method of delivering a plasmid and an interfering RNA, such as an siRNA, into a T cell comprising contacting the cell with a complex or nanoparticle as described above, wherein the complex or nanoparticle comprises the plasmid, the interfering RNA, and a VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_1$ is W or none, $X_{12}$ is A, R, or none, and $X_{13}$ is W or F, and wherein if $X_3$ is none, then $X_2$, $X_{11}$, and $X_{12}$ are none as well. In some embodiments, the VEPEP-9 peptide comprises the amino acid sequence of LRWWLRWASRWFSR-WAWWR (SEQ ID NO: 26), LRWWLRWASRWASR-WAWFR (SEQ ID NO: 27), or RWWLRWASRWALSWRWWR (SEQ ID NO: 28). In some embodiments, the molar ratio of the plasmid to the VEPEP-9 peptide in the complex or nanoparticle is about 1:10 to about 1:40 (such as about 1:20 or about 1:40) and the molar ratio of the interfering RNA to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the complex or nanoparticle further comprises one or more additional cargo molecules. In some embodiments, the one or more additional cargo molecules are useful for the treatment of the disease.

In some embodiments, there is provided a method of delivering a plasmid and an interfering RNA, such as an siRNA, into a T cell comprising contacting the cell with a) a first complex or nanoparticle as described above, wherein the first complex or nanoparticle comprises the plasmid and a VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25); and b) a second complex or nanoparticle as described above, wherein the second complex or nanoparticle comprises the interfering RNA and a VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_1$ is W or none, $X_{12}$ is A, R, or none, and $X_{13}$ is W or F, and wherein if $X_3$ is none, then $X_2$, $X_1$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the plasmid to the VEPEP-9 peptide in the first complex or nanoparticle is about 1:10 to about 1:40 (such as about 1:20 or about 1:40) and the molar ratio of the interfering RNA to the VEPEP-9 peptide in the second complex or nanoparticle is about 1:10 to about 1:40 (such as about 1:20 or about 1:40). In some embodiments, the contacting of the T cell with the first and second complex or nanoparticle is carried out in vivo. In some embodiments, the contacting of the T cell with the first and second complex or nanoparticle is carried out ex vivo. In some embodiments, the contacting of the T cell with the first and second complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the interfering RNA specifically targets an RNA molecule, such as an mRNA, encoding a protein involved in negatively regulating an immune response. In some embodiments, the interfering RNA specifically targets mRNA encoding a negative co-stimulatory molecule. In some embodiments, the negative co-stimulatory molecule includes, for example, PD-1, PD-L1, PD-L2, TIM-3, BTLA, VISTA, LAG-3, and CTLA-4. In some embodiments, the interfering RNA is siRNA. In some embodiments, the first and/or second complex or nanoparticle further comprises one or more additional cargo molecules. In some embodiments, the one or more additional cargo molecules are useful for the treatment of the disease.

In some embodiments, there is provided a method of delivering a polypeptide into a T cell comprising contacting the cell with a complex or nanoparticle as described above, wherein the complex or nanoparticle comprises the polypeptide and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_{11}$ is W or none, $X_{12}$ is A, R, or none, and $X_{13}$ is W or F, and wherein if $X_3$ is none, then $X_2$, $X_1$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the polypeptide to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the polypeptide is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a small molecule into a T cell comprising contacting the cell with a complex or nanoparticle as described above, wherein the complex or nanoparticle comprises the small molecule and an VEPEP-9 peptide comprising the amino acid sequence $X_1X_2X_3WWX_4X_5WAX_6X_3X_7X_8X_9X_{10}X_{11}X_{12}WX_{13}R$ (SEQ ID NO: 25), wherein $X_1$ is any amino acid or none, and wherein $X_2$-$X_{13}$ are any amino acid. In some embodiments, $X_1$ is βA, S, or none, $X_2$ is L or none, $X_3$ is R or none, $X_4$ is L, R, or G, $X_5$ is R, W, or S, $X_6$ is S, P, or T, $X_7$ is W or P, $X_8$ is F, A, or R, $X_9$ is S, L, P, or R, $X_{10}$ is R or S, $X_{11}$ is W or none, $X_{12}$ is A, R, or none, and $X_{13}$ is W or F, and wherein if $X_3$ is none, then $X_2$, $X_1$, and $X_{12}$ are none as well. In some embodiments, the VEPEP-9 peptide comprises the amino acid sequence of LRWWLRWASRWFSRWAWWR (SEQ ID NO: 26), LRWWLRWASRWASRWAWFR (SEQ ID NO: 27), or RWWLRWASRWALSWRWWR (SEQ ID NO: 28). In some embodiments, the molar ratio of the small molecule to the VEPEP-9 peptide in the complex or nanoparticle is about 1:10 to about 1:40 (such as about 1:20 or about 1:40). In some embodiments, the contacting of the T cell with the complex or nanoparticle is carried out in vivo. In some embodiments, the contacting of the T cell with the complex or nanoparticle is carried out ex vivo. In some embodiments, the contacting of the T cell with the complex or nanoparticle is carried out in vitro. In some embodiments, the T cell is an immortalized T cell, such as a T cell from a T cell line. In some embodiments, the T cell is a primary T cell, such as a T cell of an individual. In some embodiments, the small molecule is useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the complex or nanoparticle further comprises one or more additional cargo molecules. In some embodiments, the one or more additional cargo molecules are useful for the treatment of the disease.

In some embodiments, there is provided a method of delivering a molecule into a cell in an individual comprising administering to the individual a composition comprising a complex or nanoparticle as described above, wherein the complex or nanoparticle comprises the molecule and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the molecule to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the molecule is a cargo molecule as described above. In some embodiments, the cargo molecule is selected from the group consisting of nucleic acids, polypeptides, and small molecules. In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the cargo molecule is useful for the treatment of the disease. In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In some embodiments, there is provided a method of delivering a nucleic acid into a cell in an individual comprising administering to the individual a composition comprising a complex or nanoparticle as described above, wherein the complex or nanoparticle comprises the nucleic acid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the nucleic acid to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the nucleic acid is RNA, such as siRNA. In some embodiments, the nucleic acid is DNA, such as plasmid DNA. In some embodiments, the plasmid encodes a therapeutic product or a product useful for the treatment of a disease, such as any of the diseases to be treated described herein (e.g., cancer, diabetes, inflammatory diseases, fibrosis, viral infectious diseases, hereditary diseases, and aging and degenerative diseases). In some embodiments, the plasmid encodes a chimeric antigen receptor (CAR). In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the nucleic acid is useful for the treatment of the disease. In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In some embodiments, there is provided a method of delivering an siRNA into a cell in an individual comprising administering to the individual a composition comprising a complex or nanoparticle as described above, wherein the complex or nanoparticle comprises the siRNA and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the siRNA to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the siRNA is useful for the treatment of the disease. In some embodiments, the delivery of the siRNA into the cell results in decreased expression of a target in the cell. In some embodiments, the expression of the target is decreased by at least about 30% (such as by at least about any of 30, 35, 40, 45, 50, 55, 60, 65, 70, 75, 80, 85, 90, 95%, or more, including any ranges between these values). In some embodiments, the expression of the target remains decreased for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In some embodiments, there is provided a method of delivering a plasmid into a cell in an individual comprising administering to the individual a composition comprising a complex or nanoparticle as described above, wherein the complex or nanoparticle comprises the plasmid and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVRSWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the plasmid to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the plasmid encodes a product useful for the treatment of the disease. In some embodiments, the plasmid encodes a chimeric antigen receptor (CAR). In some embodiments, the CAR targets an antigen associated with the disease. For example, in some embodiments, the disease is cancer, and the CAR targets a cancer-associated antigen. In some embodiments, the delivery of the plasmid into the cell results in expression of a product encoded by the plasmid. In some embodiments, the product encoded by the plasmid is expressed for at least about 5 days (such as for at least about any of 5, 10, 15, 20, 25, 30, 35, 40, 45, 50 days, or more, including any ranges between these values). In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In some embodiments, there is provided a method of delivering a polypeptide into a cell in an individual comprising administering to the individual a composition comprising a complex or nanoparticle as described above, wherein the complex or nanoparticle comprises the polypeptide and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVR-SWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the polypeptide to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the polypeptide is useful for the treatment of the disease. In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In some embodiments, there is provided a method of delivering a small molecule into a cell in an individual comprising administering to the individual a composition comprising a complex or nanoparticle as described above, wherein the complex or nanoparticle comprises the small molecule and an ADGN peptide comprising the amino acid sequence $X_1KWRSX_2X_3X_4RWRLWRX_5X_6X_7X_8SR$ (SEQ ID NO: 1), wherein $X_1$ is any amino acid or none, and wherein $X_2$-$X_8$ are any amino acid. In some embodiments, $X_1$ is βA, S, or none, $X_2$ is A or V, $X_3$ is G or L, $X_4$ is W or Y, $X_5$ is V or S, $X_6$ is R, V, or A, $X_7$ is S or L, and $X_8$ is W or Y. In some embodiments, the ADGN peptide comprises the amino acid sequence of KWRSAGWRWRLWRVR-SWSR (SEQ ID NO: 2), KWRSALYRWRLWRSRSWSR (SEQ ID NO: 3), or KWRSALYRWRLWRSALYSR (SEQ ID NO: 4). In some embodiments, the molar ratio of the small molecule to the ADGN peptide in the complex or nanoparticle is about 1:10 to about 1:40 (such as about 1:20 or about 1:40). In some embodiments, the composition is administered to the individual via an intravenous, intraarterial, intraperitoneal, intravesicular, subcutaneous, intrathecal, intrapulmonary, intramuscular, intratracheal, intraocular, transdermal, oral, or inhalation route. In some embodiments, the composition is administered to the individual via an intravenous route. In some embodiments, the composition is administered to the individual via a subcutaneous route. In some embodiments, the cell is an immune cell, such as a granulocyte, a mast cell, a monocyte, a dendritic cell, a B cell, a T cell, or a natural killer cell. In some embodiments, the individual has, or is at risk of developing, a disease, and the small molecule is useful for the treatment of the disease. In some embodiments, the complex or nanoparticle further comprises one or more additional cargo molecules. In some embodiments, the one or more additional cargo molecules are useful for the treatment of the disease. In some embodiments, the composition is a pharmaceutical composition, and further comprises a pharmaceutically acceptable carrier. In some embodiments, the individual is a mammal. In some embodiments, the individual is human.

In another aspect of the present application, there is provided a method of stabilizing cargo molecules (such as a nucleic acid), comprising combining the cargo molecules with an ADGN peptide as described above, thereby stabilizing the cargo molecules. In some embodiments, the cargo molecule and the ADGN peptide form a complex or nanoparticle as described above. In some embodiments, the cargo molecule is a nucleic acid and the ADGN peptide stabilizes the supercoil structure of the nucleic acid. In some embodiments, the cargo molecule is susceptible to degradation (for example by serum components or nucleases in vitro or in vivo), and the ADGN peptide protects the cargo molecule from the degradation.

It is to be understood that any of the methods described herein can be combined. Thus, for example, a nucleic acid and a polypeptide can be delivered into a cell by combining any of the methods described above for delivering a nucleic acid into a cell with any of the methods described above for delivering a polypeptide into a cell. Possible combinations contemplated include combinations of two or more of any of the methods described herein.

Kits

Also provided herein are kits, reagents, and articles of manufacture useful for the methods described herein. Such kits may contain vials containing the ADGN peptides, assembly molecules and/or other cell-penetrating peptides, separately from vials containing the cargo molecules. At the time of patient treatment, it is first determined what particular pathology is to be treated based on for example, gene expression analysis or proteomic or histological analysis of patient samples. Having obtained those results, the ADGN peptides and any optional assembly molecules and/or cell-penetrating peptides are combined accordingly with the appropriate cargo molecules to result in complexes or nanoparticles that can be administered to the patient for an effective treatment. Thus, in some embodiments, there is provided a kit comprising: 1) an ADGN peptide, and optionally 2) one or more cargo molecules (such as nucleic acids, for example oligonucleotides). In some embodiments, the kit further comprises assembly molecules and/or other cell-penetrating peptides. In some embodiments, the kit further comprises agents for determining gene expression profiles. In some embodiment, the kit further comprises a pharmaceutically acceptable carrier.

The kits described herein may further comprise instructions for using the components of the kit to practice the subject methods (for example instructions for making the pharmaceutical compositions described herein and/or for use of the pharmaceutical compositions). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kits or components thereof (i.e., associated with the packaging or sub packaging) etc. In some embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate The various components of the kit may be in separate containers, where the containers may be contained within a single housing, e.g., a box.

EXAMPLES

Example 1: Materials and Methods

ADGN Peptides

All peptides were synthesized by solid-phase peptide synthesis using Fmoc chemistry. Peptides contained a beta-alanine, serine, or acetyl-group at the N-terminus to allow for further functionalization without using the C-terminal cysteamide group. Peptides contained either a cysteamide or COOH group at the C-terminus.

Invention Structure

ADGN peptides are secondary amphipatic peptides; they are highly versatile and show strong structural polymorphism. ADGN peptides are unfolded in solution as a free form and adopt a partial alpha helical conformation in the presence of cargo.

Oligonucleotides & siRNA siRNAs were synthesized according to the following sequences:

```
GAPDH sense
                                      (SEQ ID NO: 29)
5'-CAUCAUCCCUGCCUCUACUTT-3'

GAPDH antisense
                                      (SEQ ID NO: 30)
5'-AGUAGAGGCAGGGAUGAUGTT-3'

Cyc-B1 sense
                                      (SEQ ID NO: 31)
5'-GGCGAAGAUCAACAUGGCATT-3'

Cyc-B1 antisense
                                      (SEQ ID NO: 32)
5'-UGCCAUGUUGAUCUUCGCCTT-3'

Cyc-B3 sense
                                      (SEQ ID NO: 33)
5'-GGUGAAGAUCAGCAUGGCATT-3'

Cyc-B3 antisense
                                      (SEQ ID NO: 34)
5'-UGCCAUGUCGAUCUUCACCTT-3'

Cdc20 sense
                                      (SEQ ID NO: 35)
5'-UGCCAUGUCGAUCUUCACCTT-3'

Cdc20 antisense
                                      (SEQ ID NO: 36)
5'-UGCCAUGUCGAUCUUCACCTT-3' siF7 sense
                                      SEQ ID NO: 37)
5'-GCAAAGGCGUGCCAACUCATT-3' siF7 antisense:
                                      (SEQ ID NO: 38)
5'-TGAGUUGGCACGCCUUUGCTT-3'
```

Plasmid DNAs

Plasmids encoding luciferase and having sizes of 6.2 Kb and 3.8 Kb were obtained from New England BioLabs and recloned. A plasmid encoding YFP (6.3 Kb) was obtained from Sigma (USA) and recloned. A plasmid encoding a CD19-specific chimeric antigen receptor under the control of the CMV promoter, comprising a CD19-specific scFv linked to CD28 and CD3z signaling moieties, was prepared as previously described.

Preparation of ADGN Peptide/Cargo Particles and Complexes

The peptide/siRNA or peptide/plasmid nanoparticles were prepared by mixing amphipathic peptide and plasmid or siRNA. Stock solutions of amphipathic peptide were prepared at 1 mg/mL in distilled water and sonicated for 10 min. Stock solutions of siRNA were prepared at 5 µM concentration in water. Stock solutions of plasmid were prepared at 100 µM concentration in 50 mM Tris, 0.5 mM EDTA buffer. Peptide/plasmid complexes or nanoparticles were formed in pure water by incubating peptide (400 µM stock solution) with plasmid (100 µM stock solution) for 30 min at 37° C. with final molar ratio of peptide to plasmid at 5:1, 10:1 or 20:1. Peptide/siRNA complexes or nanoparticles were formed in water or suitable aqueous medium by incubating peptide (400 M stock solution) with siRNA (5 µM stock solution) for 30 min at 37° C. with final molar ratio of peptide to siRNA at 10:1, 20:1 or 40:1. Lower concentrations of ADGN-100/siRNA (from 20 nM to 0.125 nM) were obtained by serial dilution of the stock complexes in PBS in order to preserve the same peptide/siRNA ratio. siRNA or plasmid alone and the peptide/plasmid complex were stored in PBS for 5 days at 20° C. and 40° C. to test the stability of the plasmid.

In terms of storage and stability, stock solutions of particles prepared in water remained stable for at least three weeks at 4° C. Particles can be lyophilized for long-term storage; in that case, 5 to 20% glucose or mannitol is added to the particle solution before lyophilization to stabilize the particles during the process.

Characterization of Peptide-Based Nanoparticles

Mean particle size distribution was determined at 25° C. for 3 min per measurement and zeta potential was measured with Zetasizer 4 apparatus (Malvern Ltd). The size and polydispersity of the ADGN-100/siRNA complexes in physiological conditions (0.9% NaCl) were followed after 12/24/48 hour incubation at 4° C., 20° C. and 40° C. Three different peptide/siRNA molar ratios were analyzed (10:1, 20:1 and 40:1).

Cell Culture and Peptide-Mediated Cargo Delivery

Adherent HeLa cells (from American Type Culture Collection [ATCC]) were cultured in Dulbecco's Modified Eagle's Medium (DMEM) supplemented with 2 mM glutamine, 1% antibiotics (streptomycin 10,000 µg/mL, penicillin, 10,000 IU/mL) and 10% (w/v) foetal calf serum (FCS), at 37° C. in a humidified atmosphere containing 5% $CO_2$. A total of 150,000 cells seeded in a 35 mm dish the day prior to transfection were grown to 60% confluence and overlaid with 200 µl of preformed complexes, incubated for 3-5 min, then 400 µl of DMEM was added. After 30 min incubation at 37° C., 1 mL of fresh DMEM containing 16% FCS was added in order to reach a final FCS concentration of 10%, without removing the overlay of ADGN-100/cargo complexes. Cells were returned to the incubator for 24 or 48 hours. For siRNA targeting GAPDH, mRNA level was determined 24 hours following transduction using Quantigen (Panomics Inc.). Data reported are an average of 3 or 4 distinct experiments. For luciferase encoding plasmids, the level of luciferase expression was quantified by luminometry after 48 hours.

Cytotoxicity

Toxicity of peptide/siRNA complexes was investigated on Hela and Jurkat cell lines. A total of 30,000 cells seeded in 24-well plates the day prior to transfection were incubated with increasing concentrations of peptide or peptide/siRNA complexed at a 20:1 or 40:1 molar ratio ranging from 1 to 50 µM (500 µM ADGN-100) for 30 min prior to addition of medium to reach a final 10% concentration of FCS. Cytotoxic response was measured 12 or 24 hours later by monitoring the housekeeping gene cyclophilin mRNA levels (Quantigen, Panomic Inc.) and by colorimetric MTT assay (Sigma, Germany). For MTT assay, cell culture medium was removed and replaced with PBS containing 2.5 mg/ml of MTT for 4 hours. Results correspond to the average of 3 separate experiments.

Mouse Tumor Models

Athymic female nude mice (6-8 weeks of age) were subcutaneously inoculated in the flank with $1 \times 10^6$ HT-29 cells in 100 µl PBS.

For siRNA treatment: Two to three weeks after tumor implant, when tumor size reached about 100 $mm^3$, animals were treated by intratumoral or intravenous injection, every 3 days, with a solution of 0.1 ml of either free Cyc-B1 siRNA or Cdc20 siRNA (50 or 100 µg), control siRNA, Cyc-B3, Cyc-B1 siRNA (1, 5, 10 µg), Cdc20 siRNA (5 µg) or a cocktail of Cyc-B1 and Cdc20 siRNA (5 µg each) complexed with the ADGN peptide at a 20:1 molar ratio.

Example 2: ADGN Peptide Applications for RNA Molecule Delivery

Example 2.1: ADGN Peptides Form Stable Nanostructures with Cargoes

The size and polydispersity of the peptide/siRNA complexes in physiological conditions (0.9% NaCl) were followed after 12, 24, and 48 hour incubation at 4° C., 20° C., and 40° C. Three different peptide:siRNA molar ratios were analyzed: 10:1, 20:1, and 40:1.

At 20:1 or 40:1 molar ratios, ADGN peptides formed stable particles with siRNA having a mean diameter of 120 nm and polydispersity index (PI) of 0.3. Particles maintained their size distribution (mean diameter<130 nm and polydispersity index<0.31) and remained stable over time at different temperatures (see Tables 2-4). At 10:1 molar ratio, the particle size increased over time.

Measurements of ADGN-100/siRNA particle charge by zeta potential were similar for 20:1 and 40:1 molar ratios, with mean values of 6.0±0.8 mV and 5.1±1.0 mV, respectively. The mean zeta potential of 10:1 molar ratio particles was 15.4±0.6 mV.

TABLE 2

Incubation of peptide/siRNA particles at 20° C.

| | Incubation at 20° C. | | | | | |
| --- | --- | --- | --- | --- | --- | --- |
| | 12 h | | 24 h | | 48 h | |
| | Size (nm) | PI | Size (nm) | PI | Size (nm) | PI |
| peptide alone | | | | | | |
| peptide/siRNA (10:1) | 135 ± 5 | 0.43 ± 0.1 | 276 ± 7 | 0.41 ± 0.1 | 369 ± 20 | 0.54 ± 0.1 |
| peptide/siRNA (20:1) | 126 ± 6 | 0.27 ± 0.1 | 122 ± 3 | 0.25 ± 0.1 | 131 ± 3 | 0.27 ± 0.1 |
| peptide/siRNA (40:1) | 116 ± 3 | 0.25 ± 0.1 | 123 ± 5 | 0.31 ± 0.1 | 117 ± 8 | 0.31 ± 0.1 |

TABLE 3

Incubation of peptide/siRNA particles at 4° C.

| | Incubation at 4° C. | | | | | |
|---|---|---|---|---|---|---|
| | 12 h | | 24 h | | 48 h | |
| | Size (nm) | PI | Size (nm) | PI | Size (nm) | PI |
| peptide alone peptide/siRNA (10:1) | 130 ± 5 | 0.5 ± 0.1 | 340 ± 6 | 0.5 ± 0.1 | 500 ± 12 | 0.6 ± 0.3 |
| peptide/siRNA (20:1) | 132 ± 4 | 0.3 ± 0.1 | 150 ± 5 | 0.3 ± 0.1 | 190 ± 10 | 0.8 ± 0.3 |
| peptide/siRNA (40:1) | 140 ± 5 | 0.3 ± 0.1 | 123 ± 5 | 0.4 ± 0.1 | 180 ± 12 | 0.6 ± 0.2 |

TABLE 4

Incubation of peptide/siRNA particles at 40° C.

| | Incubation at 40° C. | | | | | |
|---|---|---|---|---|---|---|
| | 12 h | | 24 h | | 48 h | |
| | Size (nm) | PI | Size (nm) | PI | Size (nm) | PI |
| peptide alone peptide/siRNA (10:1) | 130 ± 5 | 0.4 ± 0.1 | 190 ± 4 | 0.4 ± 0.1 | 250 ± 10 | 0.4 ± 0.1 |
| peptide/siRNA (20:1) | 120 ± 6 | 0.3 ± 0.1 | 140 ± 3 | 0.5 ± 0.1 | 145 ± 3 | 0.3 ± 0.1 |
| peptide/siRNA (40:1) | 120 ± 3 | 0.3 ± 0.1 | 112 ± 5 | 0.3 ± 0.1 | 130 ± 8 | 0.3 ± 0.1 |

Example 2.2: Peptide Mediated siRNA Delivery

The ADGN peptide/siRNA complex was evaluated for siRNA delivery in both Hela and Jurkat cells using an siRNA targeting GAPDH (SEQ ID NO: 30). The siRNA transfection of both cell lines was performed in 6 well plates. The complete medium was removed and cells were washed with PBS. A 4× concentrated solution of nanoparticles was diluted in 1×PBS and immediately added to the cells. After 10 min incubation at 37° C., the cells were overlaid with free DMEM medium and incubated for an additional 30-60 min at 37° C. Complete DMEM medium was then added and cells were incubated for 48 hours at 37° C. followed by western blot analysis.

Peptide/siRNA particles were analyzed at 10:1, 20:1 and 40:1 molar ratios. siRNA dose responses were performed using serial dilutions of stock solution in PBS, with final siRNA concentrations ranging from 200 nM to 10 nM. Experiments were performed in duplicate.

Figure 1B:
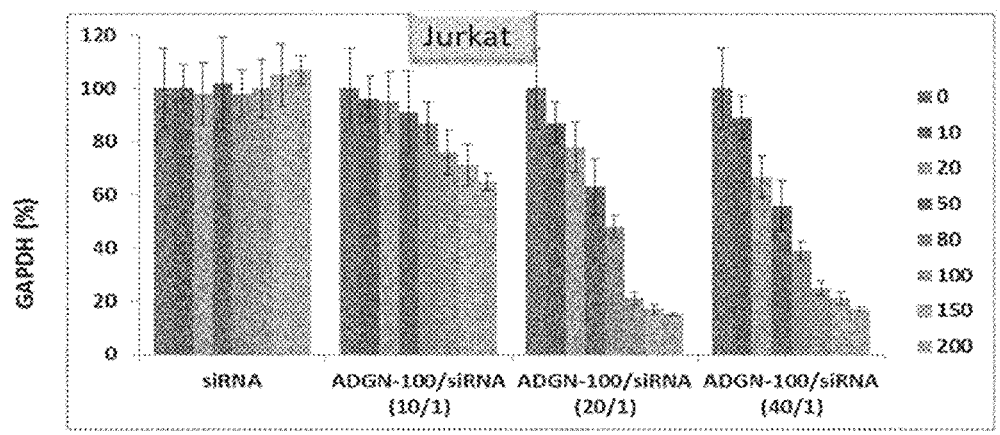
FIG. 1B shows in vitro delivery of GAPDH siRNA by peptide/siRNA particles in Jurkat cells. The columns from left to right for each experimental group correspond to siRNA concentrations of 0 nM, 10 nM, 20 nM, 50 nM, 80 nM, 100 nM, 150 nM, and 200 nM, respectively.

Dose-response experiments performed on different cultured cells revealed that peptide mediated delivery of GAPDH siRNA induced a robust downregulation of GAPDH mRNA levels (FIGS. 1A and 1B). A marked silencing of GAPDH was obtained in both cell lines with 20:1 and 40:1 molar ratio complexes. More than 60% efficiency was observed at 50 nM siRNA concentrations.

Example 2.3: ADGN Peptides Form Stable Nanostructures with Short ssRNA

Two ssRNAs were evaluated: G1 (9-Mer: 3'-AGC AGC AGC-5', SEQ ID NO: 39) and G2 (12-mer: 3'-AGC AGC AGC AGC-5', SEQ ID NO: 40). The size and polydispersity of the peptide/G1 and peptide/G2 complexes in physiological conditions (0.9% NaCl) were followed after 12 and 24 hours incubation at 4° C. and 20° C. Two different peptide: siRNA molar ratios were analyzed: 10:1 and 20:1.

As shown in Table 5, at 10:1 or 20:1 molar ratios, the ADGN peptide formed stable particles with G1 and G2 having a mean diameter of 135 nm and polydispersity index of 0.25. Particles maintained their size distribution (mean diameter<130 nm and polydispersity index<0.3) and remained stable over time.

Measurements of peptide/G1 and peptide/G2 particle charges by zeta potential were similar for 10:1 and 20:1 molar ratios, with mean values of 10.4±3.1 and 8.4±2.0 mV, respectively.

TABLE 5

ADGN peptide/ssRNA particles under different conditions

|  | 12 h | | | | 24 h | | | |
| --- | --- | --- | --- | --- | --- | --- | --- | --- |
|  | 4° C. | | 20° C. | | 4° C. | | 20° C. | |
|  | Size (nm) | PI | Size (nm) | PI | Size (nm) | PI | Size (nm) | PI |
| peptide/G1 (10:1) | 132 | 0.29 | 126 | 0.31 | 137 | 0.23 | 130 | 0.26 |
| peptide/G1 (20:1) | 126 | 0.27 | 122 | 0.25 | 141 | 0.35 | 144 | 0.41 |
| peptide/G2 (10:1) | 127 | 0.3 | 132 | 0.3 | 144 | 0.3 | 137 | 0.3 |
| peptide/G2 (20:1) | 145 | 0.3 | 141 | 0.32 | 150 | 0.42 | 151 | 0.35 |

Figure 2:
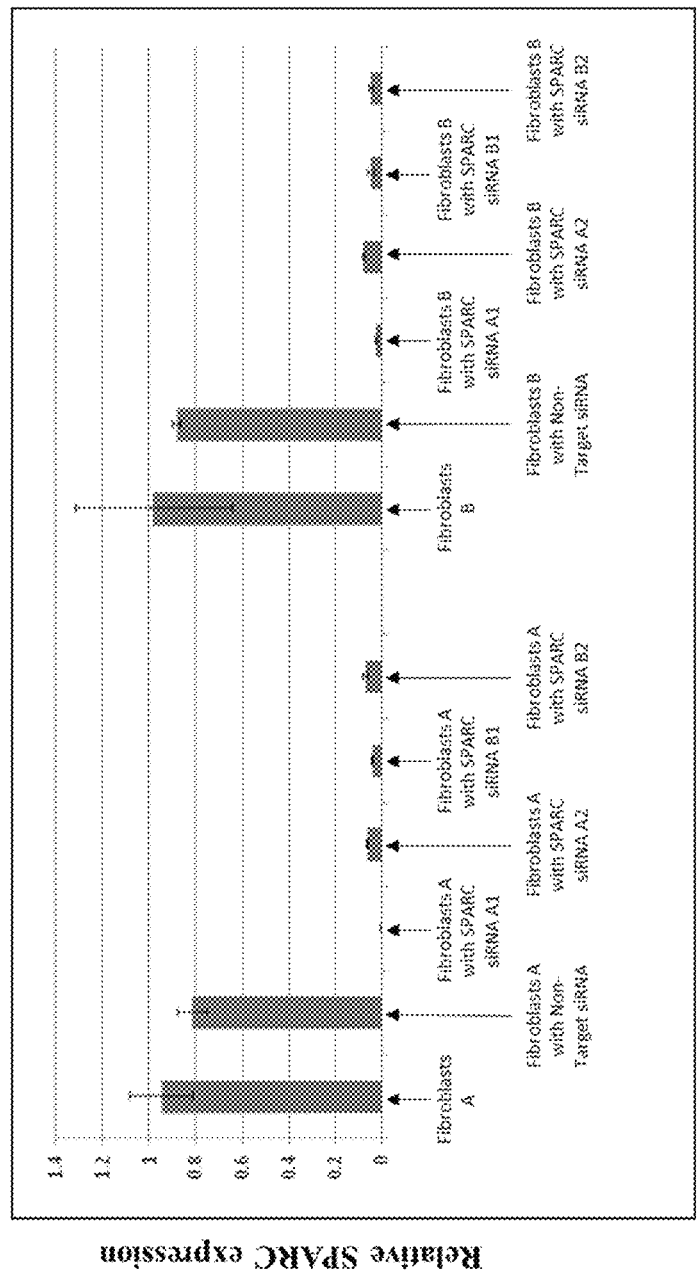
FIG. 2 shows application of peptide/SPARC siRNA complexes in Primary Human Fibroblast strains in vitro to simulate an in vitro fibrosis model.

Example 2.4: Application of Peptide/SPARC siRNA Complexes in Primary Human Fibroblast Strains In Vitro to Simulate an In Vitro Fibrosis Model Two different SPARC siRNAs (A and B) were complexed with ADGN peptide as described above. Two sets of primary human fibroblast strains (A and B) were cultured and treated with the two different peptide/SPARC siRNA complexes at a concentration of 40 nM for 48 hours. Non-target siRNA was used as negative-control treatment. Sparc expression was examined by real-time RT-PCR. Experiments were performed in duplicate (A1, A2 and B1, B2, see FIG. 2). More than 80% knockdown of SPARC was seen for each SPARC siRNA in both fibroblast cell lines.

Example 3: Toxicity Evaluation of ADGN Peptides and Peptide/siRNA Complexes on Hela and Jurkat Cells The toxicity of the ADGN peptide and ADGN peptide/siRNA complex at both 20:1 and 40:1 molar ratios was evaluated using MTT assay and by monitoring the level of cyclophilin mRNA measured by Quantigen™ technology (Affymetrix). Experiments were performed in duplicate.

Figure 3A:
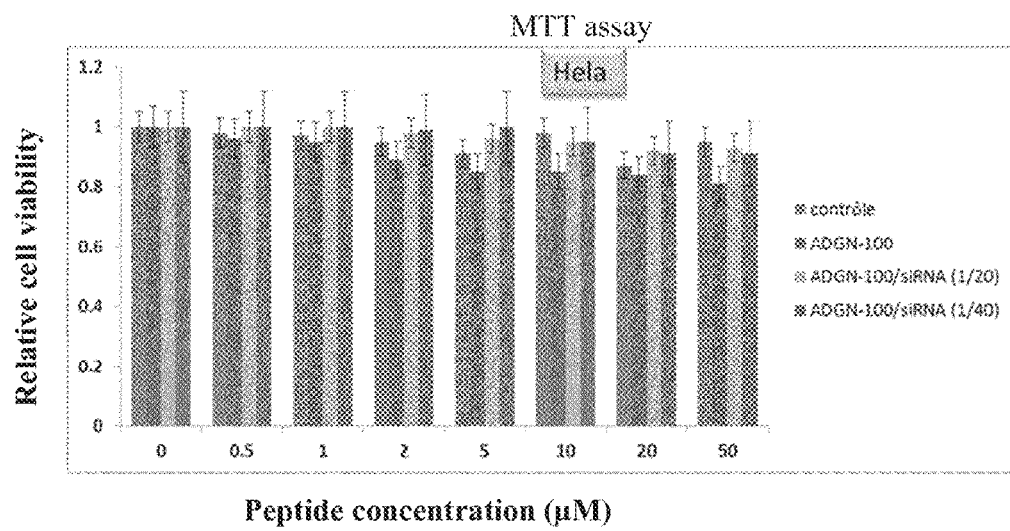
FIG. 3A shows toxicity evaluation of ADGN peptide and peptide/siRNA complexes on Hela cells by MTT assay. The columns from left to right for each concentration correspond to control, ADGN-100, ADGN-100/siRNA (1:20), and ADGN-100/siRNA (1:40), respectively.
Figure 3B:
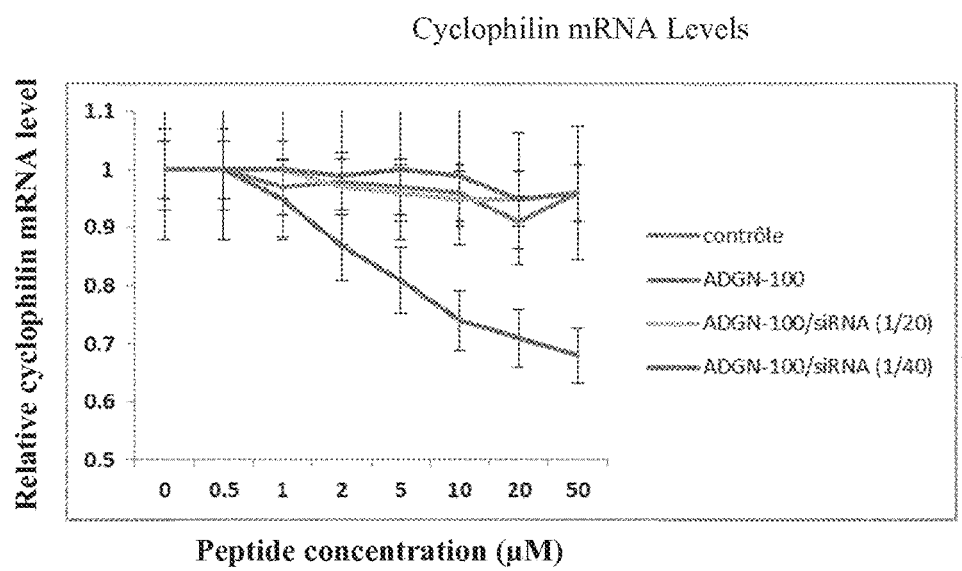
FIG. 3B shows toxicity evaluation of ADGN peptide and peptide/siRNA complexes on Hela and Jurkat cells by cyclophin mRNA levels. The lines from top to bottom at 5 μM peptide concentration correspond to ADGN-100/siRNA (1:40), control, ADGN-100 (1:20), and ADGN-100, respectively.

Data correlated well between the two methods, and no toxicity was observed for ADGN peptide/siRNA complexes up to 50 µM (FIGS. 3A and 3B). A drop in viability or cyclophilin mRNA levels of about 20-30% was observed with free peptide at 50 µM.

Example 4: In Vivo Application of ADGN Peptide/siRNA Particles

Example 4.1

ADGN peptide/siRNA complexes were used for in vivo delivery of siRNA targeting Cyclin B1, GAPDH and Cdc20. Injection every three days of ADGN peptide/cyclin B1 siRNA complexes prevented colon tumor growth in xenograft mouse models.

Athymic female nude mice (6-8 weeks of age) were subcutaneously inoculated in the flank with $1\times10^6$ PC3 (prostate cancer) or HT-29 (colon cancer) cells in 100 µl PBS. Two to three weeks after tumor implant, when tumor size reached about 100 mm³, animals were treated by intratumoral or intravenous injection, every 3 days, with a solution of 0.1 ml of 50 or 100 µg free Cyc-B1 siRNA (SEQ ID NO: 32), control siRNA, or 5 or 10 µg Cyc-B3 (SEQ ID NO: 34) or Cyc-B1 siRNA complexed with the ADGN peptide. The stock solutions of particles were prepared in water and stable for at least three weeks at 4° C. Particles can be lyophilized for long-term storage; in that case, 5 to 20% of glucose or mannitol are added to the particle solution before lyophylization to stabilize the particles during the process. Before administration, the particles were diluted into physiological conditions (0.9% NaCl and 5 to 20% mannitol). Tumor diameter was measured in two dimensions at regular intervals using a digital caliper and tumor volume was calculated as length×width×height×0.52. Curves show the mean value of tumor size in a cohort of six animals and neither animal death nor any sign of toxicity were observed. Experiments were performed according to national regulations and approved by the local animal experimentation ethical committee. The statistical significance of the results was calculated by Student's t test and $p<0.05$ considered to be statistically significant.

Figure 4:
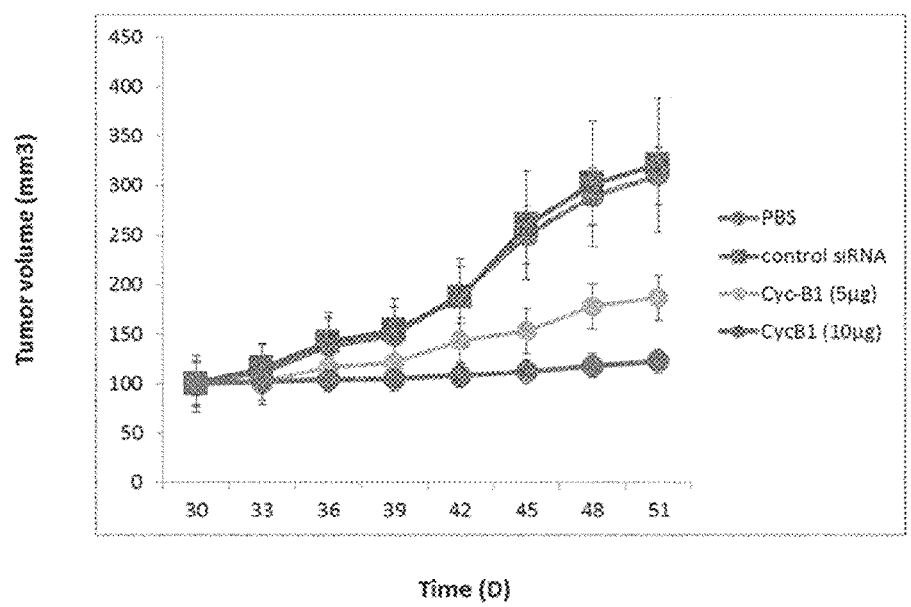
FIG. 4 shows inhibition of HT-29 tumor growth by intravenous administration of ADGN peptide/cyclin B1 siRNA complexes. The lines from top to bottom at 51 days correspond to control siRNA, PBS, Cyc-B1 (5 μg), and CycB1 (10 μg), respectively.

Following systemic intravenous administration of peptide/cyclin B1 siRNA particles, a significant reduction in HT-29 tumor size was observed at day 48, with 65% and 90% inhibition with 5 µg and 10 µg of siRNA, respectively (FIG. 4). These results, together with the lack of anti-tumor activity of the peptide/mismatch siRNA (10 µg) or of the peptide carrier alone, underscores the robustness and specificity of the biological response associated with systemic delivery of cyclin B1 siRNA.

Figure 5:
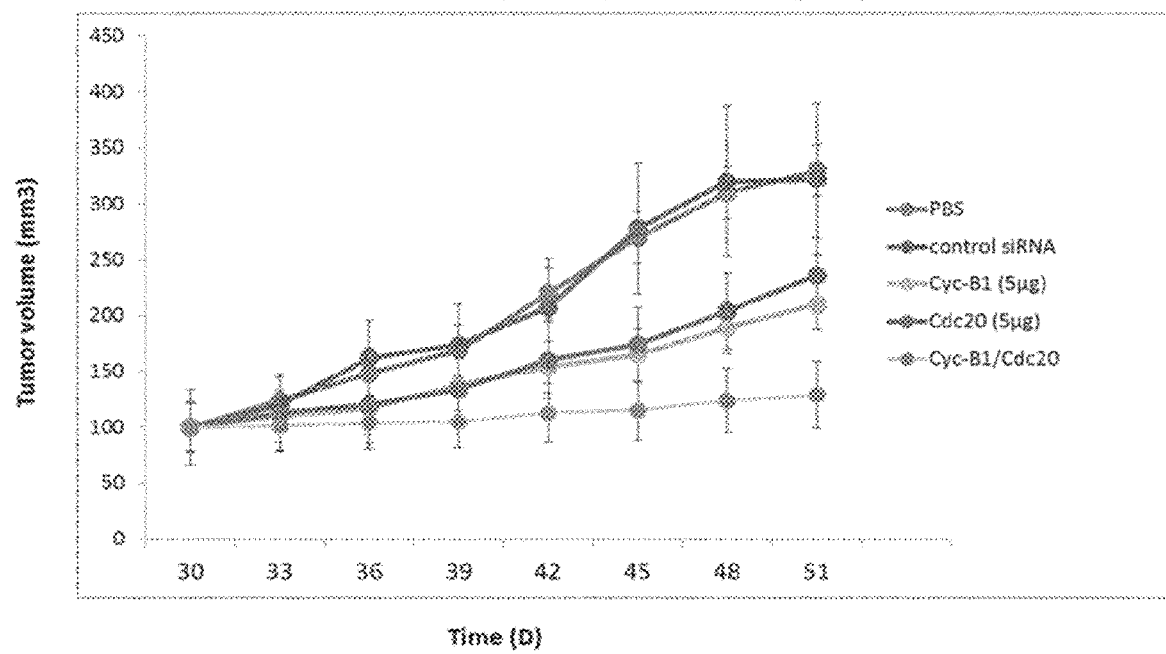
FIG. 5 shows inhibition of HT-29 tumor growth by intravenous administration of ADGN peptide/cyclin B1, ADGN peptide/cdc20, or combination ADGN peptide/cyclin B1/cdc20 siRNA complexes. The lines from top to bottom at 48 days correspond to control siRNA, PBS, Cdc20 (5 μg), Cyc-B1 (5 μg), and Cyc-B1/Cdc20, respectively

Combining cyclin B1 and Cdc20 siRNA in peptide particles prevents colon tumor growth in xenograft mouse models, upon injection every three days of peptide/siRNA complexes. Five µg (0.25 mg/kg) of Cyc-B1 siRNA, Cdc20 siRNA (SEQ ID NO: 36) and a mix of 5 µg Cyc-B1/Cdc20 siRNA (0.125 mg/kg each) in peptide/siRNA particles were injected intravenously every three days into mice bearing xenograft tumors. A significant reduction in HT-29 tumor size was observed at day 50, with 51% and 38% inhibition with 5 µg of cyc-B1 siRNA and Cdc20 siRNA, respectively (FIG. 5). A marked reduction of 94% was obtained for the peptide/cyc-B1/cdc20 siRNA complexes (FIG. 5), suggesting synergistic or additive effects of targeting these two genes. These results together demonstrated the ability of ADGN peptide/siRNA particles to deliver in vivo a cocktail of siRNAs associated with a robust biological response.

Example 4.2: In Vivo Imaging of ADGN-100/siRNA Biodistribution

In vivo fluorescence imaging was performed as previously described (Rome et al., *Methods Mol. Biol.* 948:49-65, 2013). Experiments were performed using Alexa700 labeled siRNA in complex with ADGN-100 at 20:1 molar ratio. Pharmacokinetics was evaluated on normal BALB/c and HT-29 tumor-bearing mice. Mice were intravenously (IV) or subcutaneously (SC) administered a single dose of 0.5 mg/kg of Alexa700 fluorescently labelled siRNA (200 µl)

either naked or complexed with ADGN-100 (n=4 animals per group). Anaesthetized mice, using 2% isoflurane, were illuminated by 663 nm light emitting diodes equipped with interference filters. Video of the first 15 minutes post-administration was acquired and fluorescence images were taken every hour for 5 hours and then after 24 hours using a back-thinned CCD cooled camera as previously described (Rome et al., supra; Crombez et al., *Nucleic Acids Res.* 37(14):4559-4569, 2009). At 12 or 24 hours mice were euthanized and different organs were removed for quantification of Alexa fluorescence. Whole mouse analysis was performed after 1, 2, 5, 10 and 24 hours. Blood and tissue samples (liver, spleen, kidney, lung, brain, heart, skin, pancreas, and lymph node) were collected at 12 and 24 hours post-start of dose from two animals. siRNA level was quantified as fluorescence units/mg of tissue for healthy and tumor bearing mice.

Figure 6A:
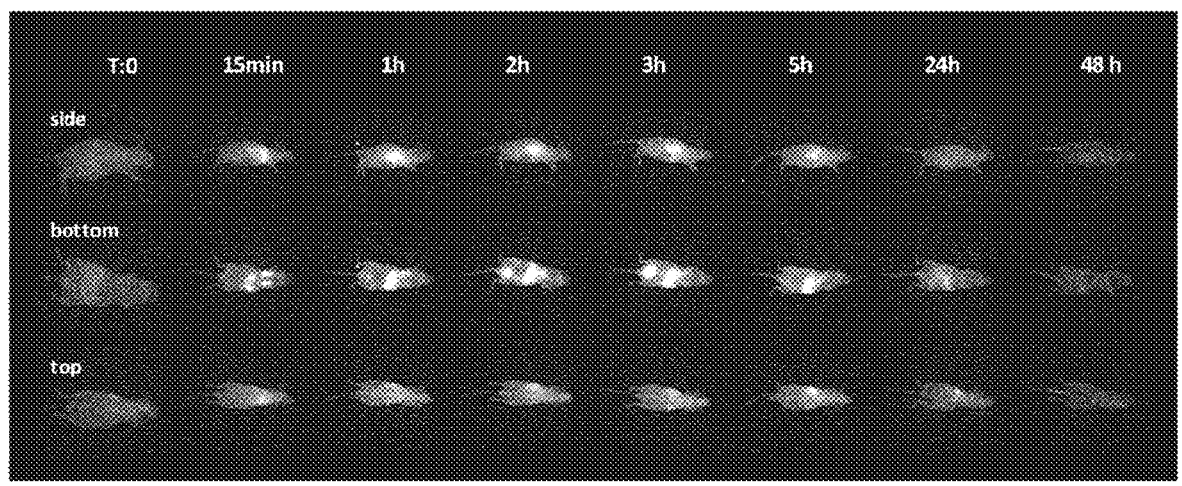
FIG. 6A shows in vivo imaging of Alexa700-labeled siRNA biodistribution at various intervals following a single intravenous injection of ADGN-100/siRNA complex.
Figure 6B:
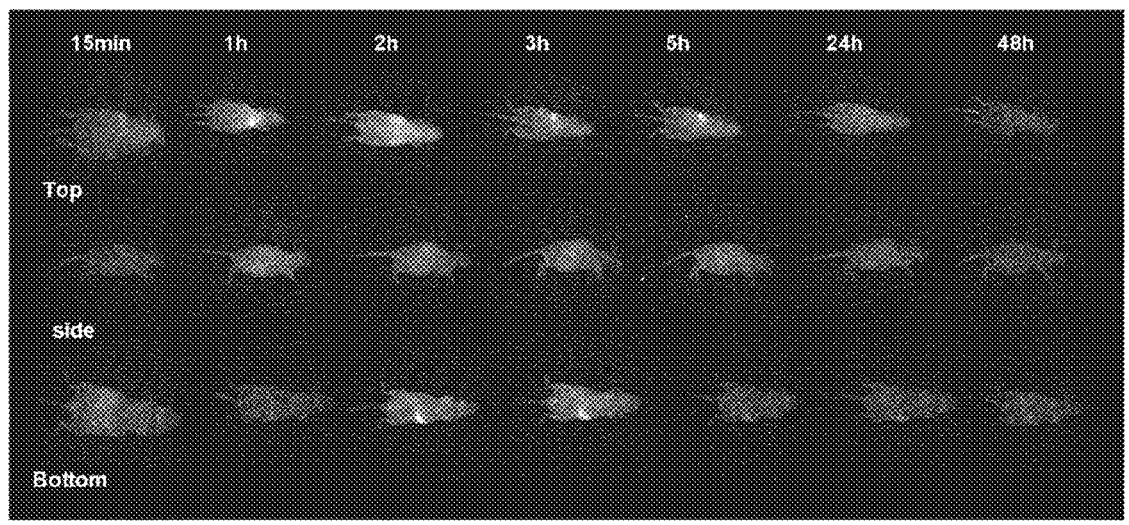
FIG. 6B shows in vivo imaging of Alexa700-labeled siRNA biodistribution at various intervals following a single subcutaneous injection of ADGN-100/siRNA complex.
Figure 7A:
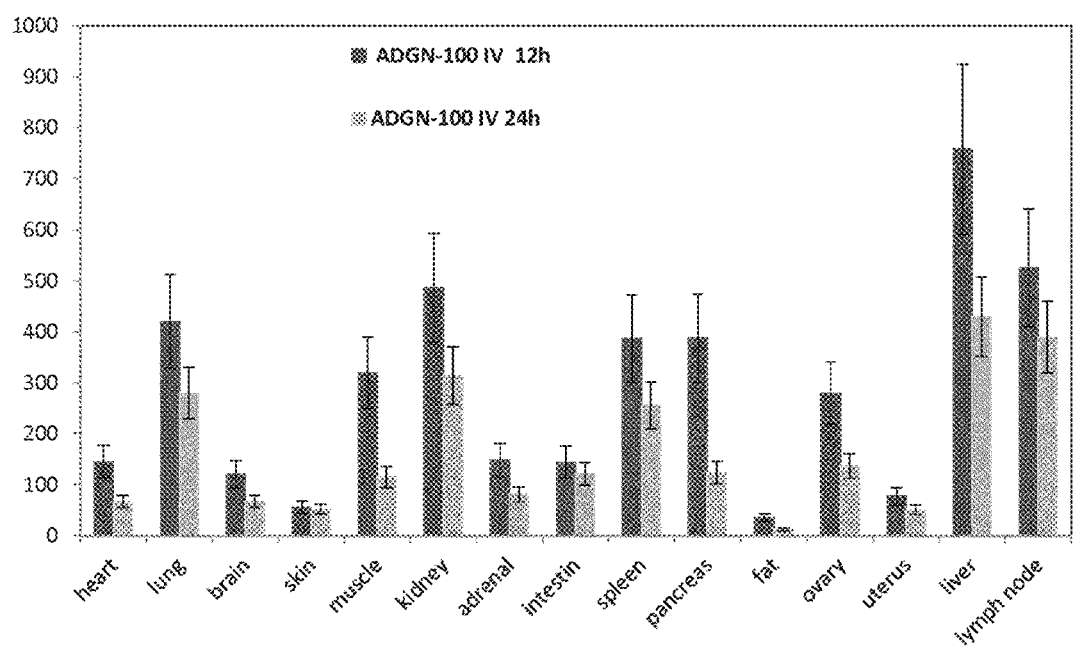
FIG. 7A shows tissue distribution of Alexa700-labeled siRNA at various intervals following a single intravenous injection of ADGN-100/siRNA complex in BALB/c mice.
Figure 7B:
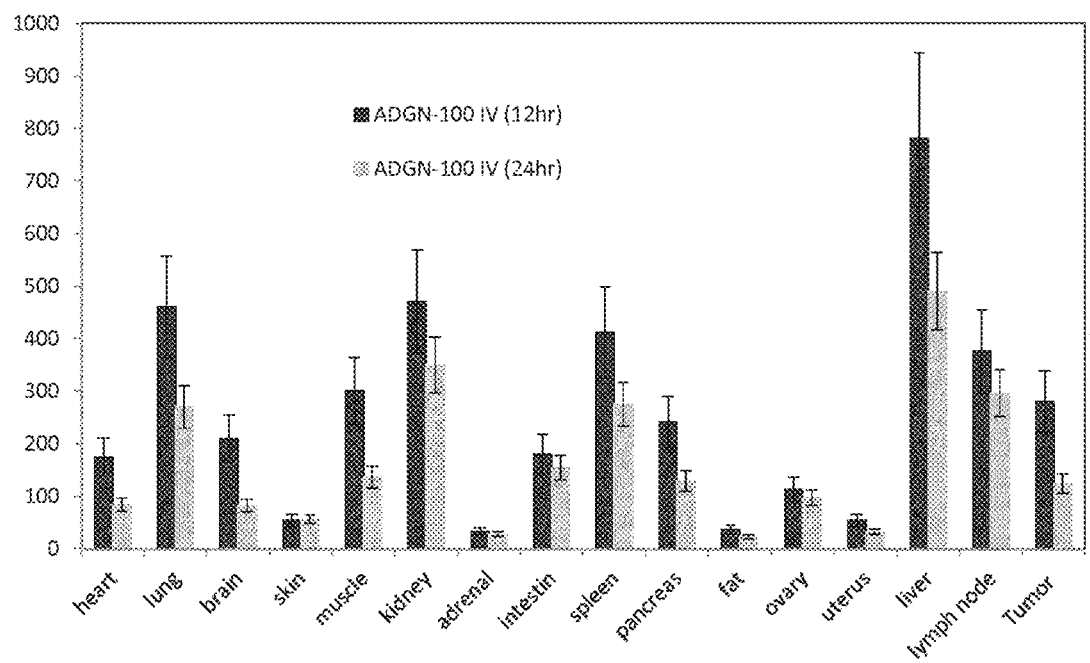
FIG. 7B shows tissue distribution of Alexa700-labeled siRNA at various intervals following a single intravenous injection of ADGN-100/siRNA complex in HT-29 tumor bearing mice.
Figure 7C:
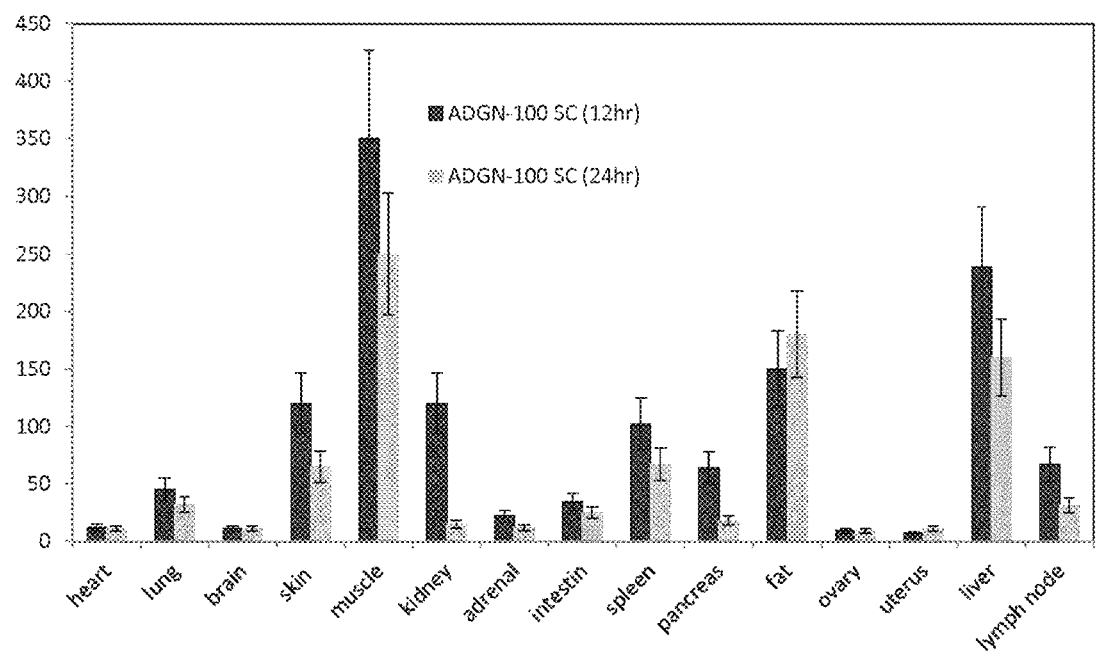
FIG. 7C shows tissue distribution of Alexa700-labeled siRNA at various intervals following a single subcutaneous injection of ADGN-100/siRNA complex in HT-29 tumor bearing mice.

ADGN-100-based particles were evaluated using both systemic intravenous and subcutaneous administration. Kinetic analysis demonstrated that the level of siRNA in different tissues peaked after 2-3 hours following a single intravenous or subcutaneous injection of ADGN-100/siRNA particles (FIG. 6). Intravenous administration of the ADGN-100/siRNA complex allowed for delivery of the siRNA to most of the analysed tissues, at significant levels in lung, kidney, spleen, lymph node, liver, pancreas and muscle, and lower levels in heart and brain (FIG. 7A). Intravenous administration also allowed for significant delivery of the siRNA to tumor tissue (FIG. 7B). Subcutaneous administration of the ADGN-100/siRNA complex allowed for significant delivery of the siRNA to muscle, skin, spleen and liver (FIG. 7C).

Example 4.3: In Vivo Delivery of siRNA Silencing Factor VII

ADGN-100 peptide was evaluated for in vivo delivery of siRNA targeting endogenous, hepatocyte-expressed blood clotting factor VII (FVII), a target expressed in the liver. ADGN-100/siRNA particles targeted the liver and led to a potent gene silencing that was fully reversible, without inducing any toxicity or adverse side effect in mice.

Stock solutions of particles were prepared in water using unmodified siRNA (siF7sense: 5'-GCAAAGGCGUGC-CAACUCATT-3', SEQ ID NO: 37; siF7antisense: 5'-TGAGUUGGCACGCCUUUGCTT-3', SEQ ID NO: 38) (Akinc et al, 2009 *Molecular Therapy* (2009) 17 5, 872-879) and ADGN-100 peptide at a 20:1 peptide/siRNA molar ratio. The peptide/siRNA particles were prepared as previously described.

Prior to in vivo use, the stability and efficacy of ADGN-100/FVIIsiRNA particles were first evaluated in vitro on HepG2 cells (Hep G2-ATCC® HB-8065). The size and polydispersity of the ADGN-100/siRNA complexes in physiological conditions (0.9% NaCl) were followed after 2, 24, and 48 hours incubation at 4° C. and after 1 to 4 weeks storage at 4° C. ADGN-100/FVIIsiRNA at 20:1 molar ratio was stable over a 4 week period of time with a mean diameter of 130 nm and polydispersity index (PI) of 0.31 (Table 6). The particle efficiency for FVII knockdown (KD) was monitored after 2 and 24 hours incubation at 4° C. and after 1 to 4 weeks storage at 4° C. FVII activity was normalized to untreated cells and knockdown results correspond to a mean of 3 separate experiments. FVII siRNA at a concentration of 100 nM in complex with ADGN-100 led to FVII knockdown of about 65% in HepG2 cells.

TABLE 6

Evaluation of ADGN-100/FVIIsiRNA particles stability and efficacy of over time

|  | 2 hours | 1 day | 7 days | 15 days | 22 days | 30 days |
| --- | --- | --- | --- | --- | --- | --- |
| Mean size (nm) | 120 ± 5 | 131 ± 7 | 138 ± 12 | 131 ± 25 | 137 ± 10 | 144 ± 22 |
| PI index | 0.33 ± 0.1 | 0.31 ± 0.5 | 0.31 ± 0.4 | 0.37 ± 0.7 | 0.41 ± 0.8 | 0.38 ± 0.7 |
| FVII KD (%) | 71 ± 12 | 68 ± 10 | 63 ± 14 | 51 ± 2 | 63 ± 11 | 65 ± 4 |

For in vivo experiments, the particles were diluted into physiological conditions (0.9% NaCl and 5 to 20% mannitol). BALB/c mice (6-8 weeks of age) were treated with a single injection of a 0.1 ml solution of either free siFVII siRNA or siFVII siRNA complexed with the ADGN peptide at 3 mg/kg (siRNA dose), via intravenous (tail vein) or subcutaneous administrations. The study included 4 groups of mice: a control group that received isotonic glucose (C, N=2); a group that received naked Factor VII siRNA (Naked, N=2); a group that received subcutaneous injection of the complex (SQ, N=3); and a group that received intravenous injection of the complex (IV, N=3).

Serum samples were collected at various time points post-administration by retroorbital bleed and serum levels of Factor VII protein were quantified relative to levels of saline control-treated animals using activity-based chromogenic test kit (BIOPHEN VII). Experiments were performed according to national regulations and approved by the local animal experimentation ethical committee.

Figure 8A:
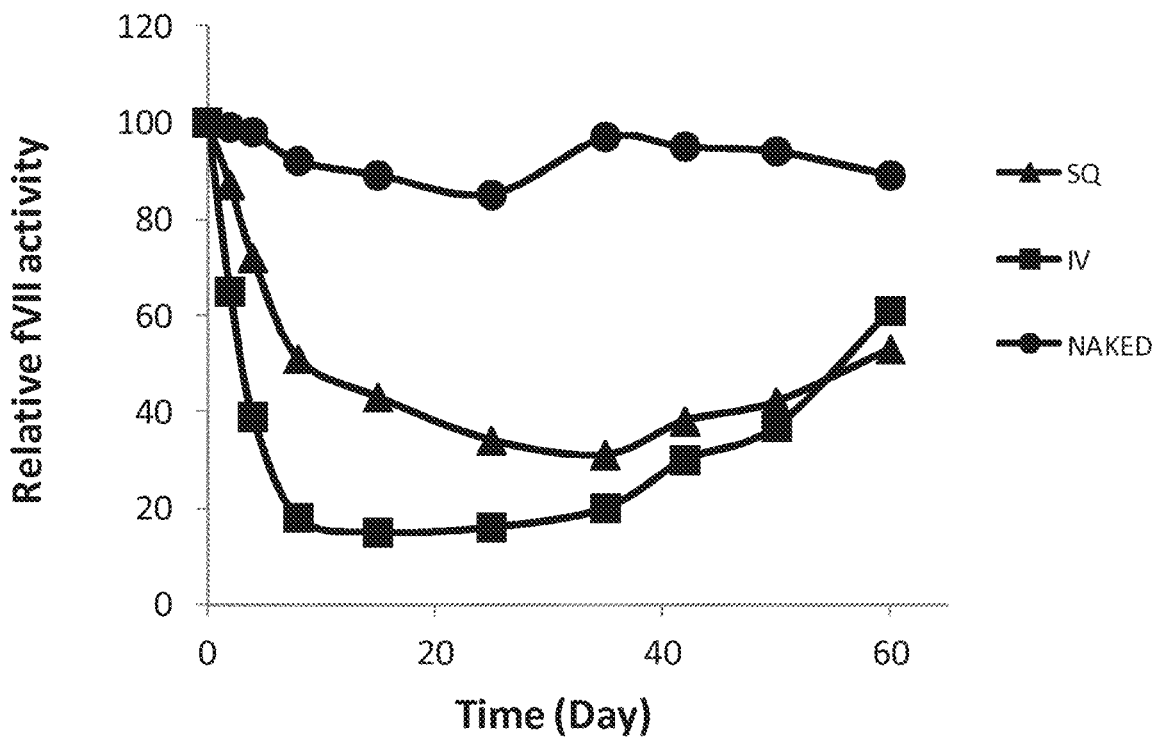
FIG. 8A shows relative Factor VII activity after intravenous or subcutaneous injection of ADGN-100/siRNA complex; injection of naked siRNA included for comparison.
Figure 8B:
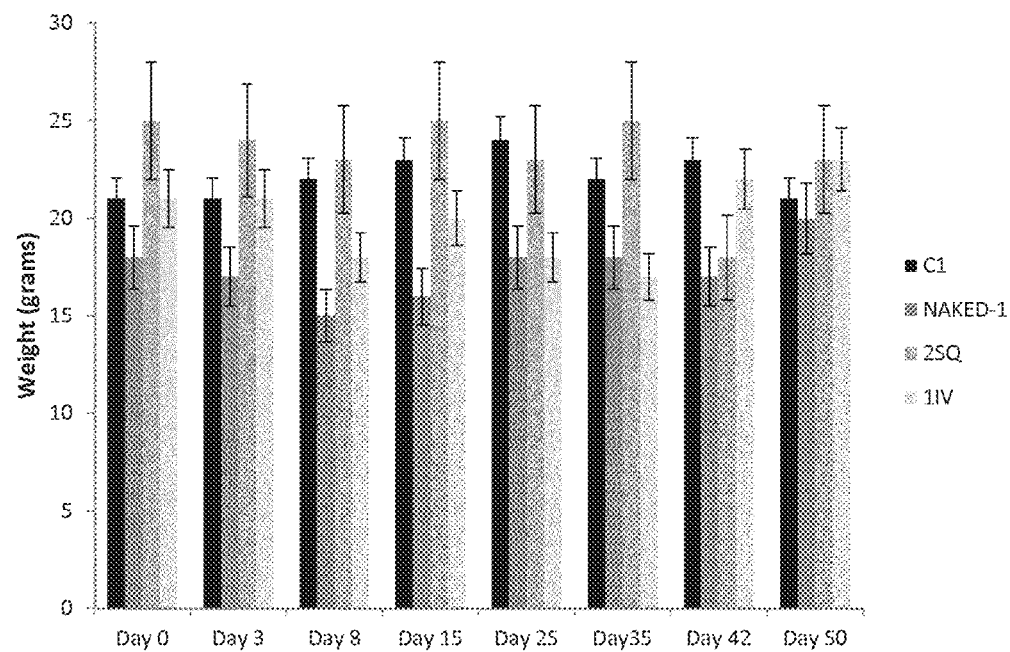
FIG. 8B shows stability of weight for mice in all treatment groups.

FIG. 8A shows the relative mean activity levels of Factor VII for the three experimental groups, normalized to the control group. Maximal knockdown of 85% and 71% were measured 8 days post-injection for intravenous injections and 24 days post-injection for subcutaneous injections, respectively. No FVII knockdown was observed for injection of naked siRNA, indicating that FVII knockdown was specific (FIG. 8A). The difference in knockdown kinetics between the routes of administration suggests that the subcutaneously injected formulation is delayed in the lymphatic system before targeting the liver. A prolonged duration of knockdown was observed with measurable reduction in FVII activity up to 60 days after a single injection of siRNA. The gene silencing is reversible, with a rebound starting at day 35 and day 45 for intravenous and subcutaneous injections, respectively (FIG. 8A). Gene silencing was observed without induction of any toxic or side effect response in mice (FIG. 8B).

Upon recovery of normal serum Factor VII levels, corresponding to approximately 60 days post-injection, animals were redosed. These results underscore the potency of ADGN-100 technology for systemic subcutaneous or intravenous delivery of siRNA to hepatocytes. ADGN-100 constitutes a useful method for in vivo target validation and is useful for therapeutic treatment.

Intravenous (IV) delivery provides a technique for rapid knockdown of a target, while subcutaneous (SQ) delivery can provide prolonged action over longer period of time. Both IV and SQ delivery may be used together for optimal or prolonged knockdown of desired targets. Repeated delivery of IV, SQ or both delivery modes in cycles of suitable length (days, weeks, months) are to be selected based on the desired profile of knockdown.

Example 5: ADGN Peptide Applications for DNA and Gene Delivery

Example 5.1: ADGN Peptide Stabilizes DNA Super Coil Structure in Solution

No change in the size and polydispersity of ADGN-100/plasmid DNA was observed after incubation at 20° C. (Table 7). Percentage of supercoiled plasmid DNA (6.2 Kb and 3.8 Kb) was measured after 1 and 4 days incubation on agarose gel electrophoresis using standard technique (Table 8 and Table 9). ADGN peptide fully stabilized the plasmid supercoil structure in all conditions tested. Similar results were observed for both plasmids. In contrast, complexes of lipid formulations with the plasmids were unstable after 4 days storage at 4, 20 or 40° C.

TABLE 7

The size and polydispersity of the ADGN-100/plasmid DNA (6.2 Kb) complexes in physiological conditions (0.9% NaCl) were followed after 12/24 hour incubation at 20° C. Three different peptide/DNA molar ratios were analyzed: 10:1, 20:1 and 40:1.

|  | 12 h | | 24 h | |
| --- | --- | --- | --- | --- |
|  | Size (nm) | PI | Size (nm) | PI |
| ADGN-100/DNA (10:1) | NO | — | NO | — |
| ADGN-100/DNA (20:1) | 140 ± 5 | 0.46 ± 0.1 | 142 ± 5 | 0.44 ± 0.1 |
| ADGN-100/DNA (40:1) | 145 ± 5 | 0.35 ± 0.1 | 146 ± 5 | 0.42 ± 0.1 |

TABLE 8

Percentage of supercoiled DNA plasmid (6.2 Kb) measured after 1 and 4 days storage measured on agarose gel electrophoresis using standard techniques.

| | 6.2 Kb plasmid super coil level (%) | | | | | |
| --- | --- | --- | --- | --- | --- | --- |
| | 1 Day | | | 4 Days | | |
| | 4° C. | 20° C. | 40° C. | 4° C. | 20° C. | 40° C. |
| DNA alone | 58 | 62 | 53 | 45 | 56 | 41 |
| peptide/DNA | 100 | 100 | 100 | 100 | 100 | 100 |
| Lipofectamine | 100 | 100 | 89 | 78 | 81 | 67 |

TABLE 9

Percentage of supercoiled DNA plasmid (3.8 Kb) measured after 1 and 4 days storage measured on agarose gel electrophoresis using standard techniques.

| | 3.8 Kb plasmid super coil level (%) | | | | | |
| --- | --- | --- | --- | --- | --- | --- |
| | 1 Day | | | 4 Days | | |
| | 4° C. | 20° C. | 40° C. | 4° C. | 20° C. | 40° C. |
| DNA alone | 68 | 58 | 61 | 54 | 66 | 59 |
| peptide/DNA | 100 | 100 | 100 | 100 | 100 | 100 |
| Lipofectamine | 100 | 95 | 91 | 82 | 71 | 72 |

Example 5.2: Stability of the DNA/Peptide Nanoparticles to Heparin Treatment

The resistance of the DNA/peptide particles and controls to heparin treatment was evaluated after 1 and 4 days incubation at 4° C., 20° C. and 40° C. Free plasmid and peptide- or lipid-formulations were treated with heparin (5 µg) for 1 hour at 32° C., then the level of free plasmid was analyzed on agarose gel electrophoresis. Peptide/plasmid particles were formulated at 20:1 molar ratio with the 6.2 Kb plasmid. As shown in Table 10, the percentage of free plasmid was low for peptide/DNA complexes following 1 and 4 days incubation at various temperatures and subsequent heparin treatment. This result demonstrates that in peptide/plasmid particles, the plasmid/peptide interactions mainly involved arginine residues, allowing for stable complexes that are not dissociated by heparin treatment. In contrast, lipid formulations of plasmids were unstable under heparin treatment, with a high percentage of free plasmid released (Table 10).

TABLE 10

Percentage of free plasmid measured after 1 and 4 days storage and heparin treatment measured on agarose gel electrophoresis using standard techniques.

| | Free Plasmid (%) | | | | | |
| --- | --- | --- | --- | --- | --- | --- |
| | 1 Day | | | 4 Days | | |
| | 4° C. | 20° C. | 40° C. | 4° C. | 20° C. | 40° C. |
| DNA alone | 100 | 100 | 100 | 100 | 100 | 100 |
| peptide/DNA | 14 | 0 | 0 | 18 | 10 | 10 |
| Lipofectamine | 78 | 67 | 87 | 82 | 71 | 69 |

Example 5.3: ADGN Peptide/Plasmid DNA Particles Promote Gene Delivery

Efficiency of luciferase expression was evaluated on Hela cells after storage of the peptide/plasmid nanoparticles at 20° C. (Table 11) or 40° C. (Table 12) for 1 and 4 days. Peptide-mediated plasmid delivery efficiency was compared with free plasmid or using a lipid formulation (lipofectamine 2000 Invitrogen). Results were obtained with 6.2 and 3.8 Kb plasmids. ADGN peptide/plasmid DNA particles promoted gene delivery as evidenced by high luciferase expression, with no significant influence of plasmid size. ADGN peptides mediated high luciferase expression even after 4 days incubation of the nanoparticles prior to transfection. In contrast, the efficiency of the lipid formulation for mediating gene delivery and luciferase expression was significantly reduced after 4 days storage of the nanoparticles at 20° C. and 40° C.

TABLE 11

Efficiency of gene expression at 48 hours measured on Hela cells after 1 and 4 days storage of peptide/plasmid nanoparticles at 20° C.:

| | Luciferase expression (RLU) | | | |
|---|---|---|---|---|
| | 6.2 Kb Plasmid | | 3.8 Kb Plasmid | |
| | 1 Day | 4 Days | 1 Day | 4 Days |
| DNA alone | $0.1\ 10^2$ | $2.4\ 10^2$ | $5.3\ 10^1$ | $1.5\ 10^2$ |
| Lipofectamine | $1.5\ 10^7$ | $2.4\ 10^4$ | $4.7\ 10^6$ | $3.8\ 10^5$ |
| peptide/DNA | $5.5\ 10^6$ | $1.7\ 10^6$ | $4.8\ 10^6$ | $2.9\ 10^6$ |

TABLE 12

Efficiency of gene expression measured on Hela cells at 48 hours after 1 and 4 days storage of peptide/plasmid nanoparticles at 40° C.

| | Luciferase expression (RLU) | | | |
|---|---|---|---|---|
| | 6.2 Kb Plasmid | | 3.8 Kb Plasmid | |
| | 1 Day | 4 Days | 1 Day | 4 Days |
| DNA alone | $0.2\ 10^2$ | $0.4\ 10^2$ | $0.3\ 10^2$ | $0.5\ 10^2$ |
| Lipofectamine | $3.2\ 10^6$ | $1.8\ 10^3$ | $2.4\ 10^6$ | $2.4\ 10^4$ |
| peptide/DNA | $2.1\ 10^6$ | $2.1\ 10^6$ | $3.5\ 10^6$ | $2.1\ 10^6$ |

Example 6: ADGN-100 Mediated Gene Transfer into T Cells

Example 6.1

ADGN-100 (Ac-KWRSAGWRWRLWRVRSWSR-Cysteamide; SEQ ID NO: 2, residue 1 acetylated, residue 19 covalently linked to cysteamide), VEPEP-6 (Ac-LWRALWRLWRSLWRLLWKA-cysteamide; SEQ ID NO: 20, residue 1 acetylated, residue 19 covalently linked to cysteamide), and VEPEP-9 (Ac-LRWWLRWASRWFSR-WAWWR-cysteamide, SEQ ID NO: 26, residue 1 acetylated, residue 19 covalently linked to cysteamide) peptides were evaluated for gene delivery into T cells, including Jurkat, 293T, and K562 cells, using a plasmid expressing luciferase. For studying stable gene delivery, a plasmid expressing YFP and containing a positive selection marker to Geneticine (G418) was used. ADGN-100 and VEPEP-9 were found to allow for potent transfection of T-cells, as well as for generation of stable transformed cell lines expressing YFP.

Materials and Methods

Cell lines were obtained from ATCC: Jurkat, Clone E6-1 (ATCC® TIB-152™) 293T/17 [HEK 293T/17] (ATCC® CRL-11268), and K562 (ATCC® CCL243™). Cells were cultured in 75 cm² flasks and 6 well dishes in Dulbecco's Modified Eagle's Medium (DMEM) containing fetal bovine serum to a final concentration of 10%. Cells were passaged every 4 days and freshly passaged 24 hours prior to transfection. Stock solutions of ADGN-100, VEPEP-6 and VEPEP-9 peptides were prepared at 2 mg/mL in distilled water and sonicated for 10 min in a water bath sonicator, then diluted just before use. Stock plasmid solutions were prepared at 100 μM concentrations in 50 mM Tris, 0.5 mM EDTA.

Nanoparticles were prepared by mixing peptide (400 μM stock solution) and plasmid (100 μM stock solution) in pure water for 30 min at 37° C., with final molar ratios of peptide to plasmid of 10:1 or 20:1 with 1 ng or 5 ng plasmid DNA. Complex solutions were then centrifuged for 5 min at 9000 rpm to remove any precipitation and diluted in 50% PBS solution just prior to transfection. Plasmids encoding luciferase (6.2 Kb) and YFP (6.3 Kb) were obtained from New England BioLabs (USA) and Sigma (USA), respectively, and re-cloned.

Cells were freshly passaged 24 hours prior to transfection. Culture medium was removed and cells were washed twice with PBS. Cells were incubated for 5 min with 0.2 or 0.4 mL of plasmid/peptide solution, then 0.4 mL of serum free medium was added. After 30 min, 1.2 mL of full medium was added and serum level was adjusted to 10%. Cultures were incubated at 37° C. for 48 hours, and then YFP or luciferase expression was determined by colorimetric assay, FACS, and fluorescence microscopy.

Forty-eight hours after transfection, cells were cultured in complete growth media containing several G418 concentrations: 0, 100, 200, 500, 800, or 1000 μg/ml. For two weeks, the drug-containing medium was replaced every 4 days (or as needed). During the second week, "islands" of surviving cells were selected. Selected colonies were then evaluated for reporter expression.

ADGN-100 Mediated Gene Expression in Different T Cell Lines

Figure 9:
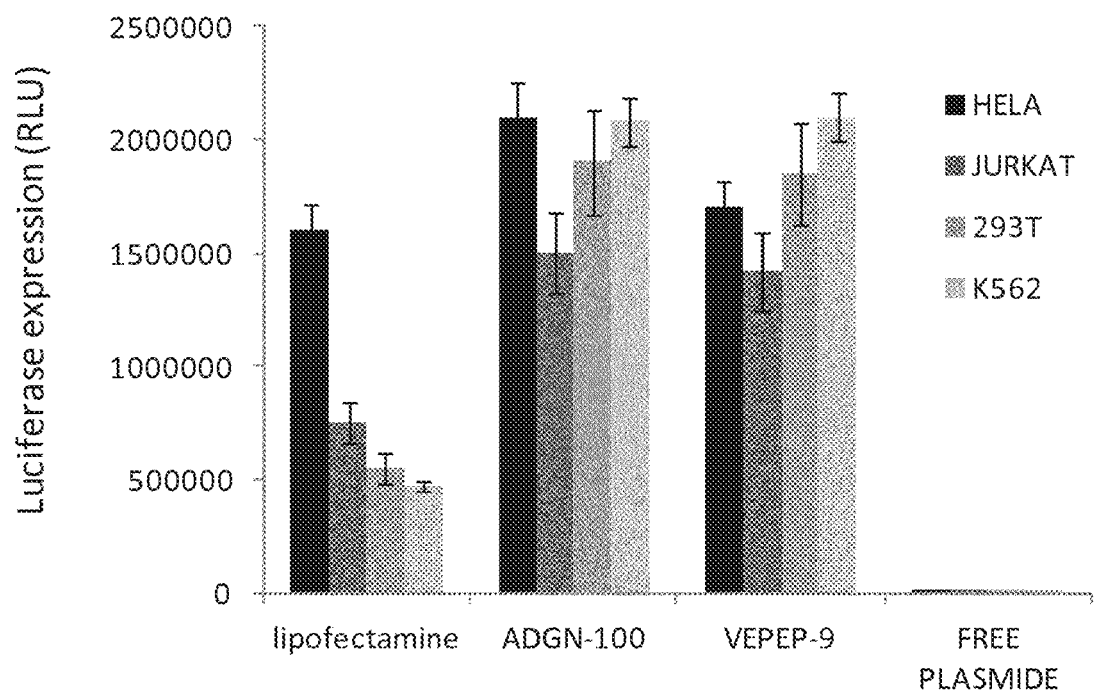
FIG. 9 shows expression of a luciferase reporter in T cell lines following transfection mediated by ADGN-100, VEPEP-9, lipofectamine, or no carrier (free plasmid).
Figure 10:
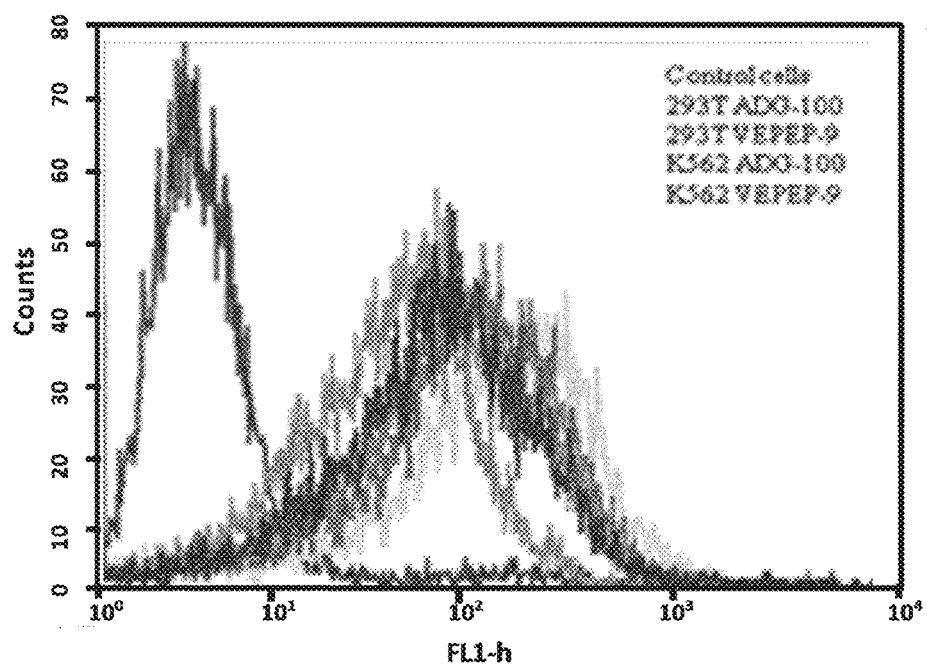
FIG. 10 shows flow cytometry analysis of 293T and K562 cell lines transfected with a YFP reporter complexed with ADGN-100 or VEPEP-9.

The efficiency of YFP and luciferase expression was evaluated for the 3 cell lines (Jurkat, 293T and K562) using 1 and 5 ng plasmid complexes with the different peptides at 10:1 and 20:1 molar ratio. Luciferase expression was monitored by colorimetric assay (FIG. 9) and GFP expression was monitored by FACS (Table 13, FIG. 10). Experiments were performed in triplicate using either free plasmid, lipofectamine (lipid based delivery system, Invitrogen) or free peptides as control.

TABLE 13

Percentages of YFP positive cells as monitored by FACS

| | Cell type | | | | | | | | | | | |
|---|---|---|---|---|---|---|---|---|---|---|---|---|
| | Jurkat | | | | 293T | | | | K562 | | | |
| | Ratio (Molar) | | | | | | | | | | | |
| | 10:1 | | 20:1 | | 10:1 | | 20:1 | | 10:1 | | 20:1 | |
| | DNA (ng) | | | | | | | | | | | |
| | 1 | 5 | 1 | 5 | 1 | 5 | 1 | 5 | 1 | 5 | 1 | 5 |
| Plasmids | 0 | 0 | 0 | 5 ± 5 | 0 | 0 | 5 ± 5 | 10 ± 5 | 0 | 0 | 0 | 0 |
| Lipofectamine | — | — | 15 ± 5 | 34 ± 8 | — | — | 10 ± 5 | 21 ± 3 | — | — | 13 ± 5 | 17 ± 2 |
| ADGN (0) | 0 | 0 | 0 | 0 | 0 | 0 | 0 | 0 | 0 | 0 | 0 | 0 |

TABLE 13-continued

Percentages of YFP positive cells as monitored by FACS

| | Cell type | | | | | | | | | | | |
|---|---|---|---|---|---|---|---|---|---|---|---|---|
| | Jurkat | | | | 293T | | | | K562 | | | |
| | Ratio (Molar) | | | | | | | | | | | |
| | 10:1 | | 20:1 | | 10:1 | | 20:1 | | 10:1 | | 20:1 | |
| | DNA (ng) | | | | | | | | | | | |
| | 1 | 5 | 1 | 5 | 1 | 5 | 1 | 5 | 1 | 5 | 1 | 5 |
| ADGN-100 | 5 ± 5 | 25 ± 5 | 37 ± 5 | 89. ± 8 | 11 ± 2 | 19.6 ± 5 | 36.5 ± 3 | 76.5 ± 5 | 10 ± 5 | 20 ± 4 | 35 ± 4 | 68 ± 5 |
| VEPEP-9 (0) | 0 | 0 | 0 | 0 | 0 | 0 | 0 | 0 | 0 | 0 | 0 | 0 |
| VEPEP-9 | 0 | 20 ± 5 | 12 ± 5 | 79. ± 5 | 0 | 20 ± 5 | 25 ± 4 | 70 ± 5 | 4 ± 5 | 17 ± 5 | 16 ± 5 | 51 ± 7 |
| VEPEP-6(0) | 0 | 0 | 0 | 0 | 0 | 0 | 0 | 0 | 0 | 0 | 0 | 0 |
| VEPEP-6 | 0 | 0 | 5 ± 5 | 13 ± 5 | 0 | 0 | 5 ± 1 | 8 ± 5 | 0 | 0 | 2 ± 5 | 5 ± 1 |

No YFP or luciferase expression was observed using 1 ng of free plasmid and only 5 to 10% positive cells were observed using 5 ng of free plasmid for transfection. No YFP or luciferase expression was observed for the three cell lines with VEPEP-6-mediated transfection, using either 1 or 5 ng of plasmid. By contrast, efficient gene expression was observed for the three cell lines after transfection mediated by either ADGN-100 or VEPEP-9. The highest level of expression was obtained with 5 ng DNA complexed at 20:1 peptide to plasmid ratio. The transfection efficiency varied between 65 to 85% depending on the cell line. ADGN-100 was 2- and 5-fold more efficient than lipofectamine for gene delivery in Jurkat and 293T/K562 cells, respectively.

ADGN-100 Mediated Stable Transfection of T Cells.

The efficiency of ADGN-100-mediated transfection for producing stable YFP-expressing clones was evaluated for both 293T and K562 T cells. Cells were transfected with 5 ng plasmid complexed with ADGN-100 at 20:1 molar ratio. Transfection was performed in complete medium (10% FCS) for 48 hours, and YFP-expressing clones were analyzed by flow cytometry at various timepoints (2, 5, 7, and 14 days) for 2 weeks.

Figure 11:
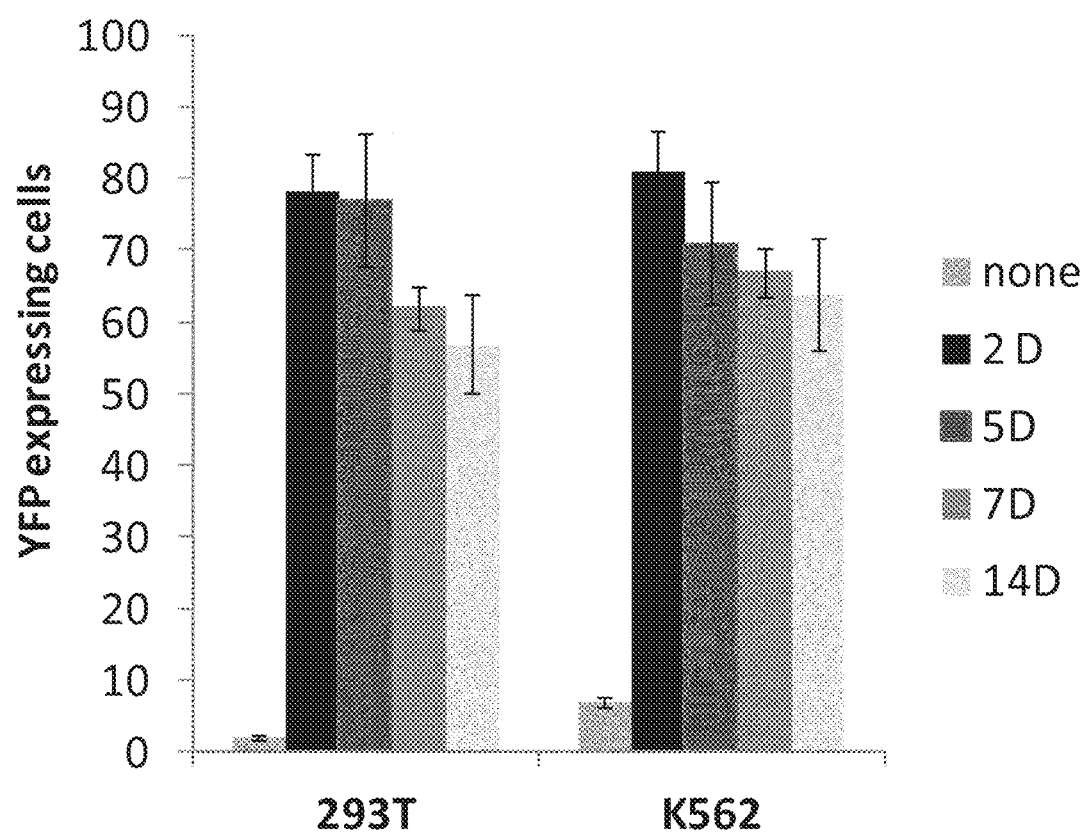
FIG. 11 shows expression over time of a YFP reporter in 293T or K562 cells following transfection mediated by ADGN-100.
Figure 12A:
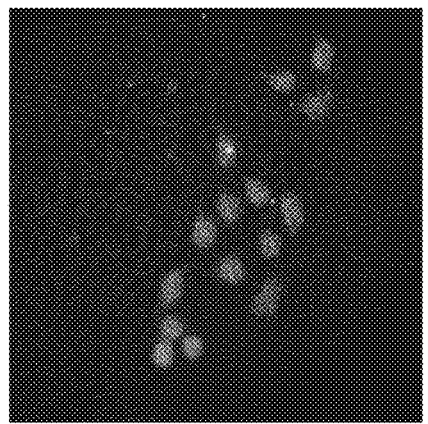
FIG. 12A shows fluorescent microscopy of 293T cells stably expressing a YFP reporter following transfection mediated by ADGN-100.
Figure 12B:
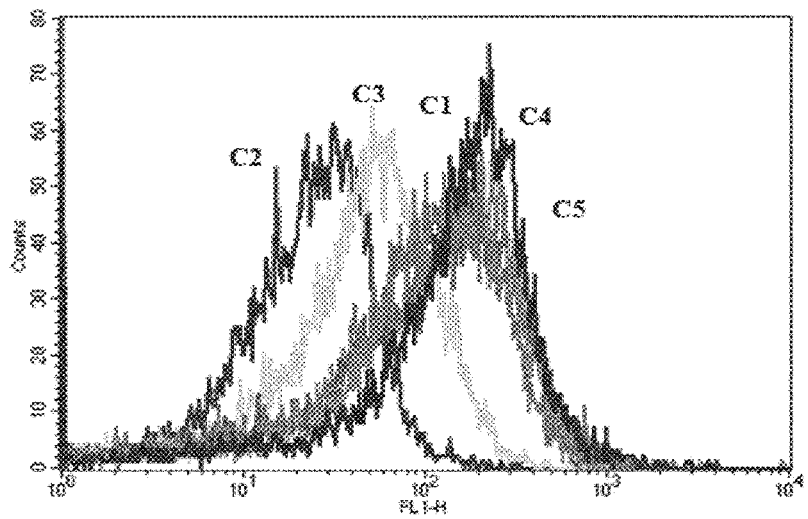
FIG. 12B shows flow cytometry analysis of 293T cells stably expressing a YFP reporter following transfection mediated by ADGN-100.

As shown in FIG. 11, ADGN-100-mediated transfection efficiency was about 80% for both K562 and 293T cells, and YFP expression was stably maintained at 14 days post-transfection, with more than 57% (293T) and 65% (K562) YFP-positive cells. Forty-eight hours after transfection, stable YFP-expressing clones were selected by growth in media containing varying concentrations of G418 for 3 weeks and analyzed by FACS and microscopy. Several individual clones of 293T cells stably expressing YFP were selected and expanded in 96-well tissue culture plates to high confluence. All selected clones expressed high levels of YFP (FIGS. 12A and 12B).

Example 6.2: Stable Gene Delivery in T Cells and Production of Anti-CD19-CAR—T Cells The potency of ADGN-technology for cell engineering and CAR-T cell engineering was evaluated. ADGN-100 peptide was shown to efficiently deliver an anti-CD19 CAR vector expressing plasmid into T cells isolated from peripheral blood mononuclear cell (PBMC) and produce stable anti-CD19 CAR T cells.

Materials and Methods

T cells were isolated from peripheral blood mononuclear cells (PBMCs) with anti-CD3/anti-CD28 antibodies bound to paramagnetic beads (Dynabeads ClinExVivo CD3/CD28, Invitrogen) at a ratio of 3:1 (beads:cells). The T cells were transfected with ADGN-100 particles complexed with a plasmid encoding a CD19-specific chimeric antigen receptor (CAR) having a CD19-specific scFv linked to CD28 and CD3z signaling moieties and under the control of a CMV promoter. T cells were transfected by incubation with peptide/plasmid complex at 2 ratios (20:1 and 30:1) for 48 hours.

On day 4, the level of transfected cells was analyzed, and cells were transferred to fresh T cell expansion medium (AIM V medium supplemented with 5% heat-inactivated human AB Serum, 1% Gluta-Max, 300 IU/mL IL-2). On day 12, cells were harvested using anti-CD3/anti-CD28 paramagnetic beads with the Dynal ClinExVIVO MPC magnet (Invitrogen), washed, and analyzed for viability and anti-CD19 expression by flow cytometry. Expression of the anti-CD19 CAR on the T cells was evaluated by flow cytometry using a Protein L assay. Biotinylated Protein L was purchased from ThermoScientific, reconstituted in sterile water at a stock concentration of 50 ng/μl, and stored at 4° C. 7-AAD (Sigma) was used to determine viability.

Results

Figure 13:
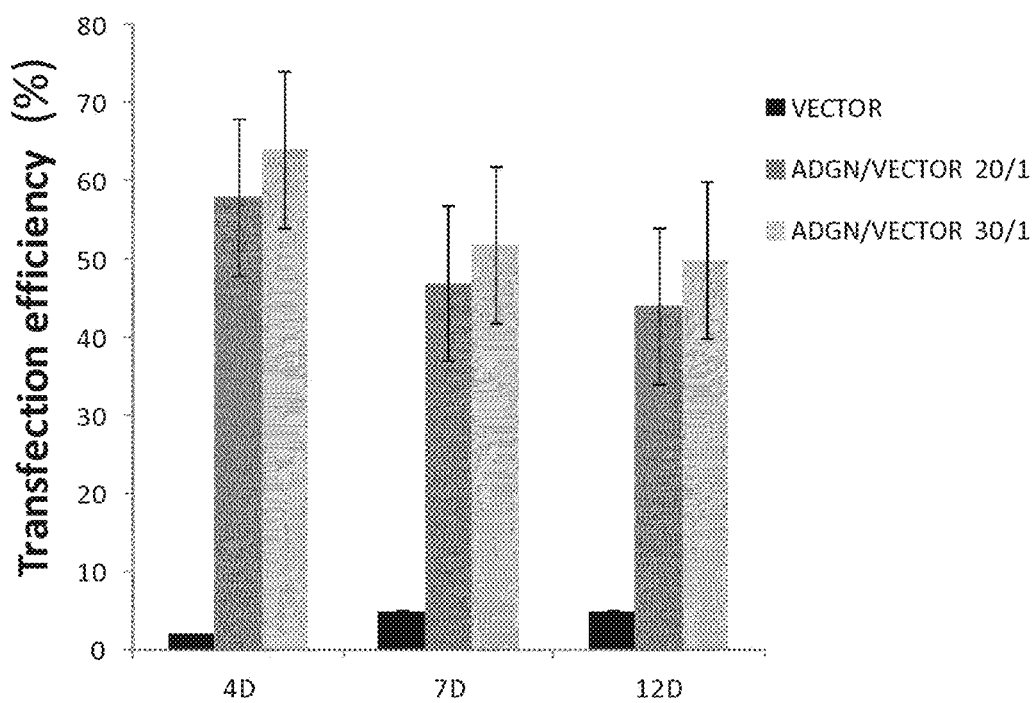
FIG. 13 shows transfection efficiency in primary T cells of ADGN-100/anti-CD-19 CAR vector complex at molar ratios of 20:1 and 30:1; results normalized to untransfected cells.
Figure 14:
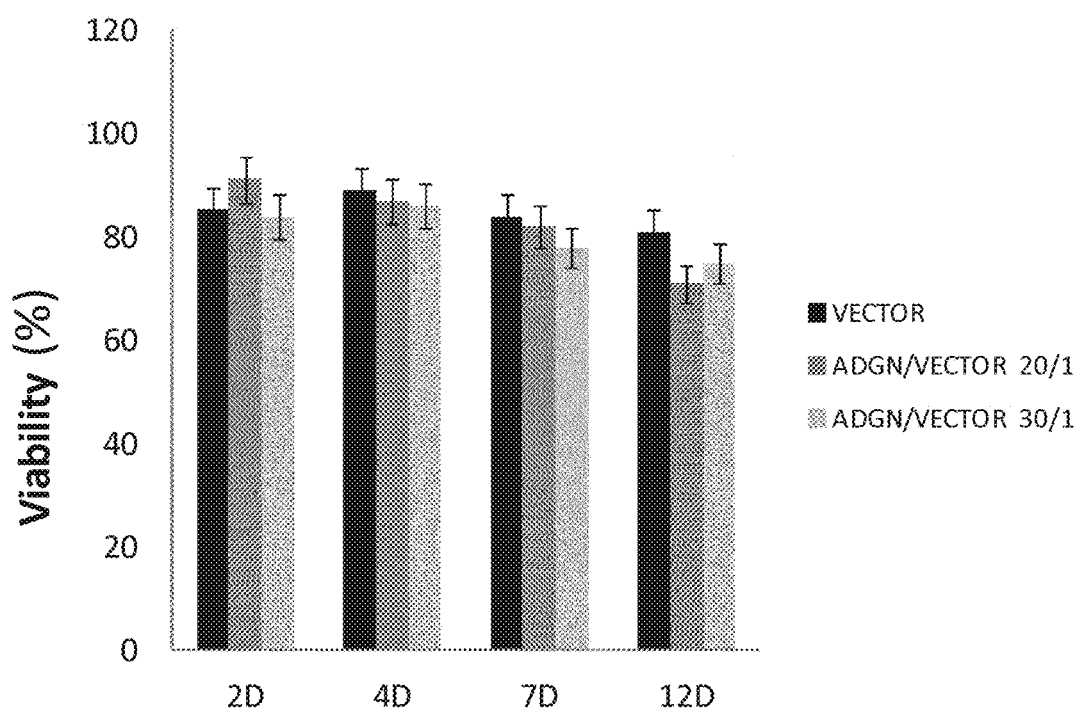
FIG. 14 shows viability of primary T cells following transfection with ADGN-100/anti-CD-19 CAR vector complex assayed by flow cytometry using 7-AAD; results normalized to untransfected cells.

ADGN-100 mediated anti-CD19 CAR vector transfection in T cells isolated from PBMCs with 57% and 63% efficiency at 20:1 and 30:1 molar ratios of peptide to plasmid, respectively (FIG. 13). Results were normalized to untransfected cells and compared to T cells incubated with free plasmid. Stable expression was maintained over 12 days in 41% and 48% of cells at 20:1 and 30:1 molar ratios of peptide/plasmid, respectively. Average viability was approximately 80% or higher in all conditions, indicating no cytotoxicity was associated with ADGN-100 transfection (FIG. 14). Results were normalized to untransfected cells and compared to T cells incubated with free plasmid. These results demonstrate that ADGN-100 technology with a non-viral vector for transfection can be effectively used to produce target specific T cells for immune-based therapies, such as anti-cancer therapies employing tumor-targeting T cells.

Example 7: Comparison of ADGN-100 with Other Secondary Amphipathic Cell Penetrating Peptides (CADY/VEPEP-6/VEPEP-9)

Only 4 out of 19 residues are shared between ADGN-100 peptides and CADY, VEPEP-6, or VEPEP-9 peptides.

Secondary Structure Comparison

Figure 15:
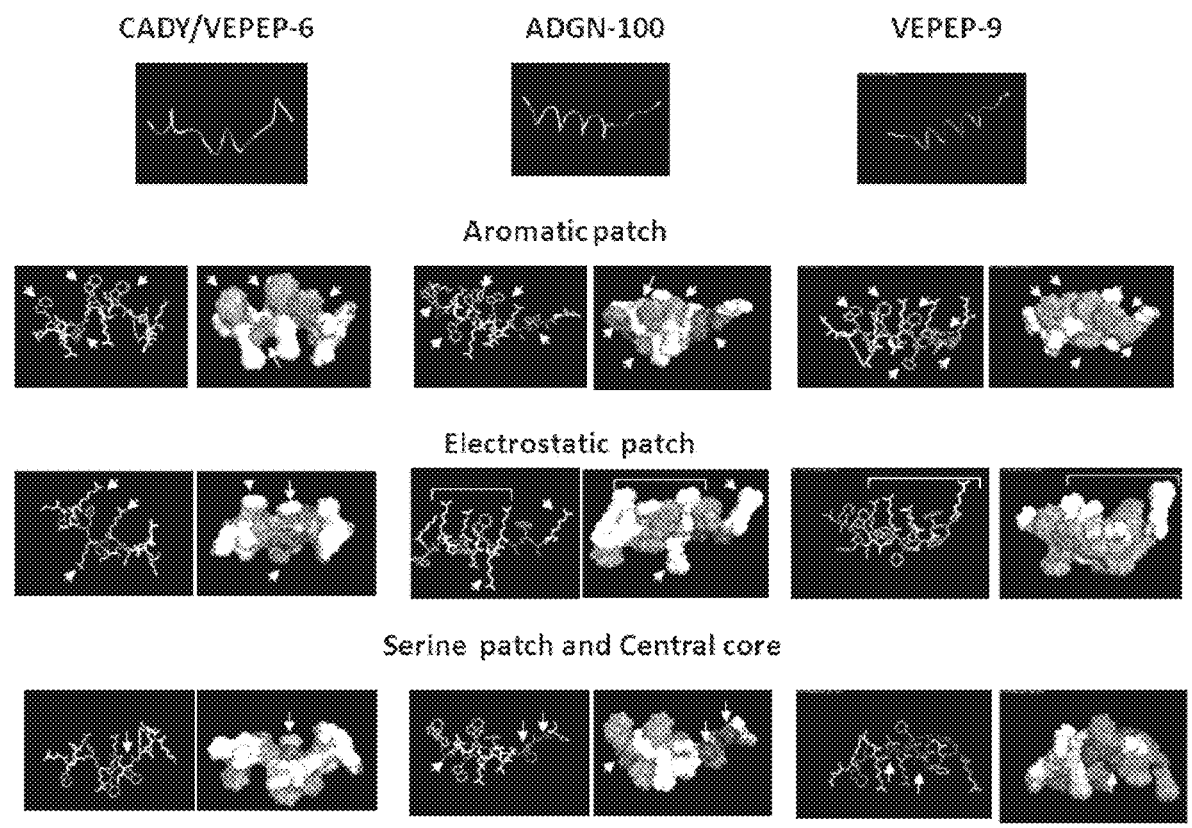
FIG. 15 shows 3-dimensional structural models of ADGN-100, CADY, VEPEP-6, and VEPEP-9 peptides, showing locations of helices and aromatic and electrostatic patches.

Secondary structures were determined using the molecular modeling peplook-Zultim program (Thomas A and Brasseur R., 2006, Prediction of peptide structure: how far are we?, Proteins. 65, 889-97). All four peptides adopt a secondary amphipathic helical conformation within membrane-mimicking environments, exposing Trp-groups on one side, charged residues on the other and hydrophobic residues on yet another (FIG. 15). CADY and VEPEP-6 adopt the same secondary structure, with helical motif in the core, C- and N-terminus of the peptide (Table 14). In contrast ADGN-100 and VEPEP-9 peptides contains a single core helical motif, which is longer in VEPEP-9 and in agreement with Konate et al 2010 (Biochemistry), Crowlet et al 2014 (BBA).

TABLE 14

| Peptide | Secondary structure prediction |
|---|---|
| ADGN-100 | KWRSAGWRWRLWRVRSWSR<br>hhhhhhhhhhhhhhh |
| CADY | GLWRALWRLLRSLWRLLWKV<br>hhh hhhhh hhhh |
| VEPEP-6 | LWRALWRLWRSLWRLLWKA<br>hhh hhhhh hhhh |
| VEPEP-9 | LRWWLRWASRWFSRWAWWR<br>hhhhhhhhhhhhhhhhh | h: helix motif

Nanoparticle Size Comparison

VEPEP-6, CADY and VEPEP-9, at molar ratio 20:1 (peptide:siRNA), form nanoparticles with siRNA with size ranging between 100-200 nm and a mean diameter centered at 150 nm and a positive charged surface (zeta potential of 40 mV, 25 mV and 17 mV for CADY, VEPEP-6 and VEPEP-9 based particles, respectively).

ADGN-100 peptide forms smaller particles with a mean diameter<130 nm and polydispersity index<0.31. Moreover, the charge of ADGN-100/siRNA particle is closer to neutral with zeta potential of 6.0±0.8 mV. This is a major advantage for in vivo applications.

Toxicity

Figure 16:
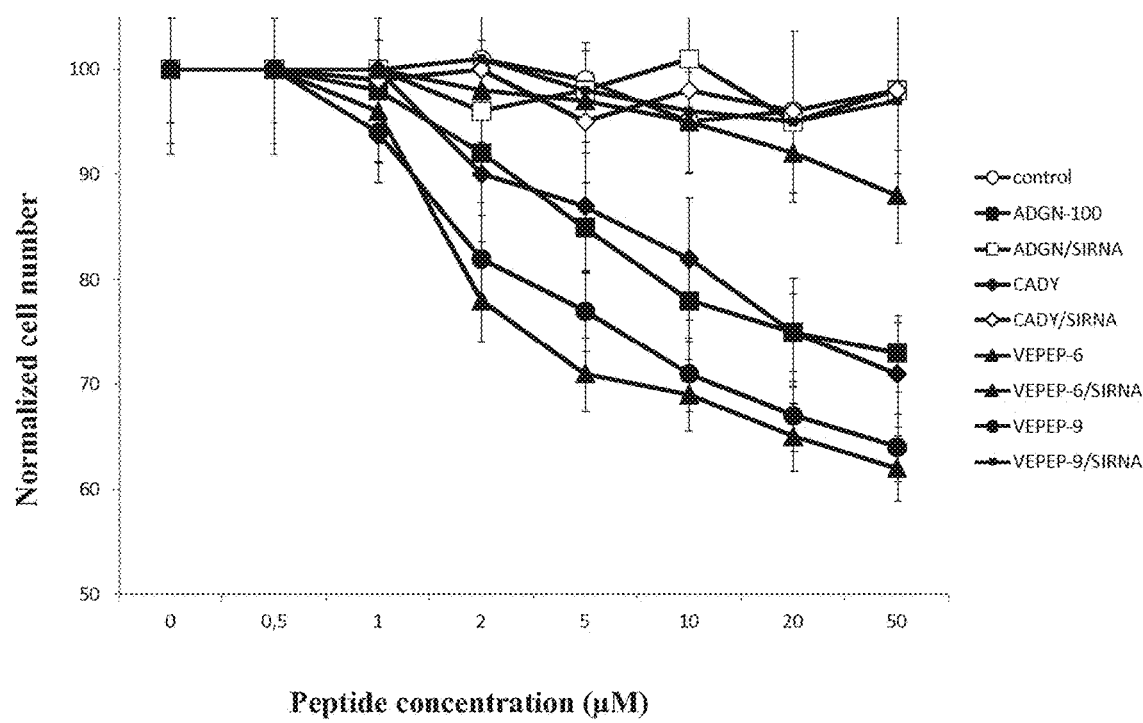
FIG. 16 shows toxicity evaluation of ADGN, CADY, VEPEP-6 and VEPEP-9 peptides and peptide/siRNA complexes on Hela cells by MTT assay. The lines from top to bottom at 20 µM peptide concentration correspond to ADGN-100/siRNA, CADY/siRNA, control, VEPEP-6/siRNA, VEPEP-9/siRNA, ADGN-100, CADY, VEPEP-6, VEPEP-9, respectively.

No toxicity was observed for ADGN-100/siRNA and CADY/siRNA complexes up to 50 µM and 30% toxicity was obtained with free ADGN-100 and CADY at 50 µM (FIG. 16). VEPEP-6 exhibits more toxicity than the other peptides in both complexed (10% toxicity) and free form (40% cell death) at 50 µM. No toxicity wax observed for VEPEP-9/siRNA complexes, and in contrast to ADGN-100, VEPEP-9 exhibits more toxicity in its free form (40% cell death) at 50 µM, which can be attributed to the longer helical structure of VEPEP-9.

Gene Delivery In Vitro

VEPEP-6, VEPEP-9, CADY and ADGN peptides form complexes with plasmid DNA. The efficiency of the peptides in stabilizing 6.2 Kb plasmid DNA was evaluated by following both the integrity of plasmid supercoil structure and the stability of the DNA/peptide particles following heparin treatment after 1 or 4 days incubation at 4° C., 20° C. or 40° C. Free plasmid and complex with a lipid formulation (lipofectamine 2000 Invitrogen) were included for comparison. For heparin treatment, 5 µg heparin was incubated with the sample for 1 hour at 32° C. followed by agarose gel electrophoresis to resolve free plasmid. As shown in Tables 15 and 16, VEPEP-9 and ADGN-100 peptides fully stabilized plasmid DNA in all conditions tested. ADGN-100 fully protected plasmid DNA from degradation and heparin treatment. In comparison VEPEP-6 and lipid formulations were poorly stable after 4 days of incubation at 4, 20 or 40° C.

TABLE 15

| | Supercoil level (%) | | | | | |
|---|---|---|---|---|---|---|
| | Day 1 | | | Day 4 | | |
| Carrier | 4° C. | 20° C. | 40° C. | 4° C. | 20° C. | 40° C. |
| No carrier | 58 | 62 | 53 | 45 | 56 | 41 |
| CADY | 89 | 89 | 100 | 85 | 100 | 100 |
| VEPEP-6 | 98 | 87 | 100 | 100 | 100 | 87 |
| VEPEP-9 | 100 | 100 | 100 | 100 | 100 | 100 |
| ADGN-100 | 100 | 100 | 100 | 100 | 100 | 100 |
| Lipofectamine | 100 | 100 | 89 | 78 | 81 | 67 |

TABLE 16

| | Free plasmid (%) | | | | | |
|---|---|---|---|---|---|---|
| | Day 1 | | | Day 4 | | |
| Carrier | 4° C. | 20° C. | 40° C. | 4° C. | 20° C. | 40° C. |
| No carrier | 100 | 100 | 100 | 100 | 100 | 100 |
| CADY | 17 | 25 | 27 | 21 | 29 | 35 |
| VEPEP-6 | 0 | 0 | 0 | 10 | 5 | 5 |
| VEPEP-9 | 56 | 61 | 69 | 75 | 76 | 67 |
| ADGN-100 | 12 | 0 | 0 | 17 | 10 | 10 |
| Lipofectamine | 78 | 67 | 87 | 82 | 71 | 69 |

Peptide-mediated plasmid delivery efficiency was evaluated in Hela cells by measuring luciferase expression 48 hours post-delivery using peptide/plasmid nanoparticles that had been incubated at 20° C. for 1 or 4 days. Efficiency of gene expression at 48 hr measured on Hela cell after 1 and 4 days storage of peptide/plasmid nanoparticles at 20° C. In each condition tested, ADGN peptide was at least 10- and 2-fold more potent than VEPEP-6 and CADY, respectively (Table 17). ADGN and VEPEP-9 peptides exhibited similar levels of plasmid delivery efficiency, about 100-fold higher than that observed with the lipid formulation after 4 days incubation.

TABLE 17

| | Luciferase expression (RLU) | | | |
|---|---|---|---|---|
| | Plasmid 6.2 Kb | | Plasmid 3.8 Kb | |
| Peptide/lipid | 1 day | 4 days | 1 day | 4 days |
| No peptide/lipid | $0.10 \cdot 10^2$ | $2.31 \cdot 10^2$ | $5.24 \cdot 10^1$ | $1.52 \cdot 10^2$ |
| Lipofectamine | $1.51 \cdot 10^7$ | $2.65 \cdot 10^4$ | $4.81 \cdot 10^6$ | $3.84 \cdot 10^5$ |
| ADGN-100 | $5.51 \cdot 10^6$ | $4.90 \cdot 10^6$ | $4.81 \cdot 10^6$ | $5.90 \cdot 10^6$ |
| CADY | $2.91 \cdot 10^6$ | $3.31 \cdot 10^6$ | $3.85 \cdot 10^6$ | $3.12 \cdot 10^6$ |
| VEPEP-6 | $4.21 \cdot 10^5$ | $2.71 \cdot 10^4$ | $4.41 \cdot 10^5$ | $1.65 \cdot 10^5$ |
| VEPEP-9 | $1.70 \cdot 10^7$ | $4.50 \cdot 10^6$ | $5.42 \cdot 10^6$ | $1.21 \cdot 10^7$ |

Intracellular Delivery In Vitro

Figure 17:
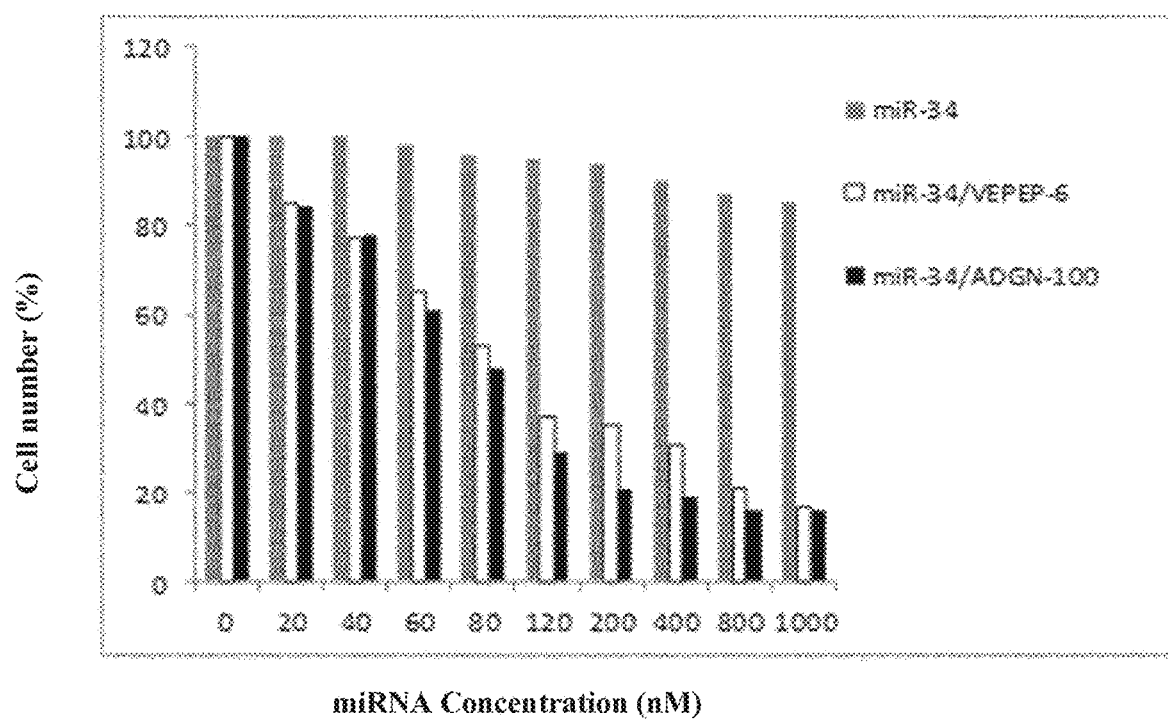
FIG. 17 shows in vitro comparison of miRNA delivery by ADGN and VEPEP-6 peptides.

The human miR-34a microRNA has recently been implicated in cancer, particularly with its expression relating to TP53 status. ADGN-100 or VEPEP-6 peptide/miRNA-34 particles were used in an antiproliferation assay with MCF7 breast cancer cells. Single-stranded miRNA-34 (UGGCAGUGUGGUUAGCUGGUUG, SEQ ID NO: 41) was added to cultured cells free of peptide or in peptide/miRNA particles with either ADGN-100 or VEPEP-6 at a peptide:miRNA ratio of 20:1. Dose responses of free miRNA-34 (gray bars), VEPEP-6/miRNA-34 particles (white bars), and ADGN-100/miRNA-34 particles (black bars) were evaluated (FIG. 17). ADGN-100 greatly improved the antiproliferative property of miRNA-34, having an IC50 of 81 nM.

Intracellular Delivery In Vivo

Figure 18:
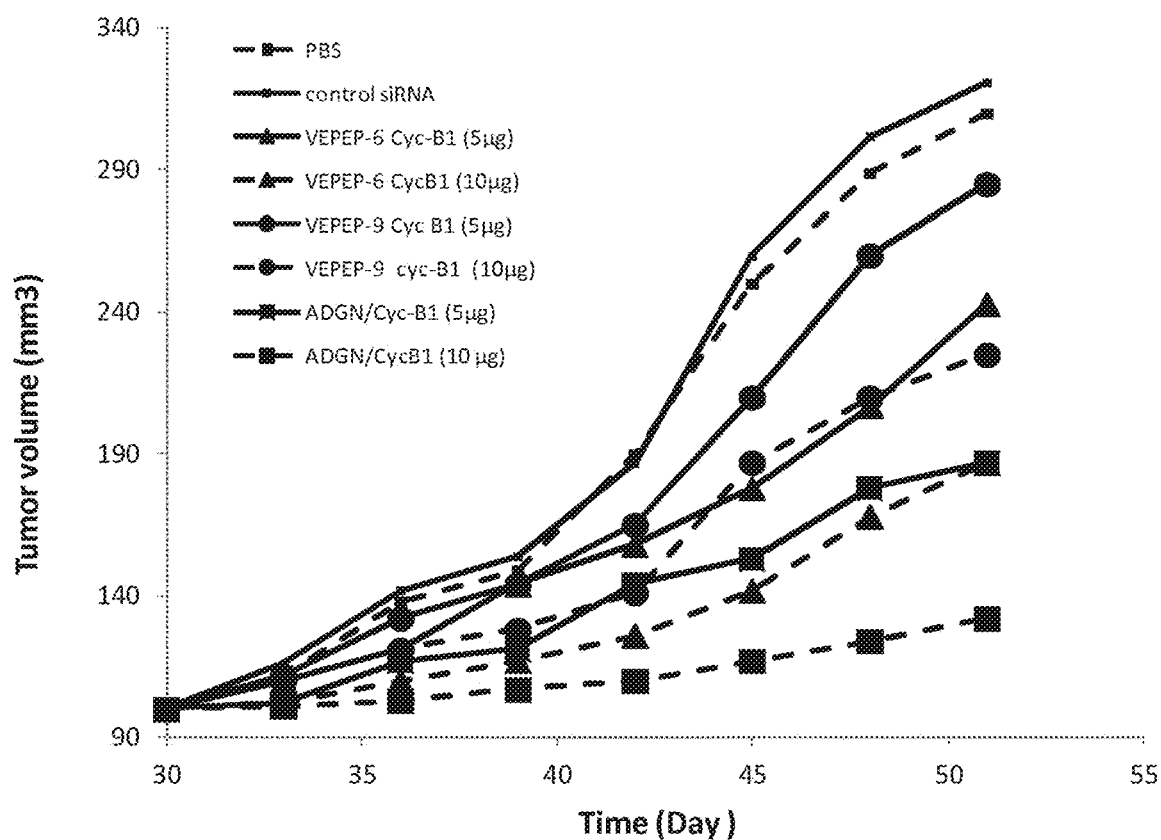
FIG. 18 shows in vivo comparison of siRNA delivery by ADGN, VEPEP-6 and VEPEP-9 peptides. The lines from top to bottom at 51 days correspond to control siRNA, PBS, VEPEP-9/Cyc-B1, VEPEP-6/Cyc-B1, and ADGN/Cyc-B1, respectively.

Particles of siRNA complexed with either ADGN, VEPEP-6 or VEPEP-9 were used for systemic intravenous administration. Five or ten μg (0.25 mg/kg or 0.5 mg/kg) of Cyc B1 siRNA in ADGN peptide particles, VEPEP-6 particles or VEPEP-9 particles was injected intravenously every three days into mice bearing xenograft HT-29 tumors. A significant reduction in tumor size was observed after day 50 using 0.25 mg/kg siRNA, with 61% and 33% inhibition for ADGN and VEPEP-6 particles, respectively (FIG. 18). At day 50, tumor progression was reduced by 87% and 65% when using 0.5 mg/kg of ADGN/siRNA and VEPEP-6/siRNA particles, respectively. By contrast, VEPEP-9/siRNA particles reduced tumor growth by only 12% and 38% at 0.25 mg/kg and 0.5 mg/kg, respectively. ADGN/siRNA particles were 2- and 9-fold more efficient than VEPEP-6 and VEPEP-9 particles, respectively.

SEQUENCE LISTING

ADGN-100
$X_1$KWRS$X_2X_3X_4$RWRLWRX$_5X_6X_7X_8$SR,    SEQ ID NO: 1

ADGN-100 a
KWRSAGWRWRLWRVRSWSR,    SEQ ID NO: 2

ADGN-100 b
KWRSALYRWRLWRSRSWSR,    SEQ ID NO: 3

ADGN-100 c
KWRSALYRWRLWRSALYSR,    SEQ ID NO: 4

ADGN-100 a1
$X_1$KWRSAGWRWRLWRVRSWSR,    SEQ ID NO: 5

ADGN core motif
RWRLWRX$_5X_6X_7X_8$SR,    SEQ ID NO: 6

ADGN-100 aa
KWRS$_s$AGWR$_s$WRLWRVRSWSR,    SEQ ID NO: 7

ADGN-100 ab
KWR$_s$SAGWRWR$_s$LWRVRSWSR,    SEQ ID NO: 8

ADGN-100 ac
KWRSAGWR$_s$WRLWRVR$_s$SWSR,    SEQ ID NO: 9

ADGN-100 ba
KWRS$_s$ALYR$_s$WRLWRSRSWSR,    SEQ ID NO: 10

ADGN-100 bb
KWR$_s$SALYRWR$_s$LWRSRSWSR,    SEQ ID NO: 11

ADGN-100 bc
KWRSALYR$_s$WRLWRSR$_s$SWSR,    SEQ ID NO: 12

ADGN-100 bd
KWRSALYRWR$_s$LWRS$_s$RSWSR,    SEQ ID NO: 13

ADGN-100 be
KWRSALYRWRLWRS$_s$RSWS$_s$R,    SEQ ID NO: 14

ADGN-100 ca
KWR$_s$SALYRWR$_s$LWRSALYSR,    SEQ ID NO: 15

ADGN-100 cb
KWRS$_s$ALYR$_s$WRLWRSALYSR,    SEQ ID NO: 16

ADGN-100 cc
KWRSALYRWR$_s$LWRS$_s$ALYSR,    SEQ ID NO: 17

ADGN-100 cd
KWRSALYRWRLWRS$_s$ALYS$_s$R,    SEQ ID NO: 18

CADY
GLWRALWRLLRSLWRLLWKV,    SEQ ID NO: 19

VEPEP-6a
LWRALWRLWRSLWRLLWKA,    SEQ ID NO: 20

VEPEP-6b
LWRALWRLLRSLWRLWRKA,    SEQ ID NO: 21

VEPEP-6c
LWRALWRLWRSLWRLWRKA,    SEQ ID NO: 22

VEPEP-6d
LWRALWRLLRALWRLLWKA,    SEQ ID NO: 23

VEPEP-6e
LWRALWRLLRNLWRLLWKA,    SEQ ID NO: 24

VEPEP-9
$X_1X_2X_3$WW$X_4X_5$WA$X_6X_3X_7X_8X_9X_{10}X_{11}X_{12}$W$X_{13}$R,    SEQ ID NO: 25

VEPEP-9a
LRWWLRWASRWFSRWAWWR,    SEQ ID NO: 26

VEPEP-9b
LRWWLRWASRWASRWAWFR,    SEQ ID NO: 27

VEPEP-9c
RWWLRWASRWALSWRWWR,    SEQ ID NO: 28

GAPDH sense
CAUCAUCCCUGCCUCUACUTT,    SEQ ID NO: 29

GAPDH antisense
AGUAGAGGCAGGGAUGAUGTT,    SEQ ID NO: 30

Cyc-B1 sense
GGCGAAGAUCAACAUGGCATT,    SEQ ID NO: 31

Cyc-B1 antisense
UGCCAUGUUGAUCUUCGCCTT,    SEQ ID NO: 32

Cyc-B3 sense
GGUGAAGAUCAGCAUGGCATT,    SEQ ID NO: 33

| | |
|---|---|
| Cvc-B3 antisense | SEQ ID NO: 34 |
| UGCCAUGUCGAUCUUCACCTT, | |
| Cdc20 sense | SEQ ID NO: 35 |
| UGCCAUGUCGAUCUUCACCTT, | |
| Cdc20 antisense | SEQ ID NO: 36 |
| UGCCAUGUCGAUCUUCACCTT, | |
| siF7 sense | SEQ ID NO: 37 |
| GCAAAGGCGUGCCAACUCATT, | |
| siF7 antisense | SEQ ID NO: 38 |
| TGAGUUGGCACGCCUUUGCTT, | |
| G1 | SEQ ID NO: 39 |
| CGACGACGA, | |
| G2 | SEQ ID NO: 40 |
| CGACGACGACGA, | |
| miR-34 | SEQ ID NO: 41 |
| UGGCAGUGUGGUUAGCUGGUUG, | |

We claim:

1. A non-naturally occurring peptide comprising the amino acid sequence RWRLWRX$_1$X$_2$X$_3$X$_4$SR (SEQ ID NO: 6), and wherein X$_1$ is V or S, X$_2$ is R, V, or A, X$_3$ is S or L, and X$_4$ is W or Y.

2. The peptide of claim 1, wherein the peptide is no more than 20 amino acids in length.

3. The peptide of claim 2, wherein the peptide is 19 or 20 amino acids in length.

4. The peptide of claim 1, wherein the peptide comprises an acetyl group covalently linked to its N-terminus.

5. The peptide of claim 1, wherein the peptide comprises a cysteamide group covalently linked to its C-terminus.

6. The peptide of claim 1, wherein the peptide comprises two residues separated by three or six residues that are linked by a hydrocarbon linkage.

7. A complex comprising the peptide of claim 1 and a cargo molecule.

8. The complex of claim 7, wherein the cargo molecule is a nucleic acid.

9. The complex of claim 8, wherein the nucleic acid is selected from the group consisting of a siRNA, a miRNA, a DNA plasmid, and an analogue thereof.

10. A nanoparticle comprising the peptide of claim 1 and a cargo molecule.

11. The nanoparticle of claim 10, wherein the cargo molecule is a nucleic acid.

12. The nanoparticle of claim 10, wherein the molar ratio of the cargo molecule to the peptide in the nanoparticle is from 1:5 to 1:40.

13. The nanoparticle of claim 10, wherein the nanoparticle comprises a targeting moiety at the surface.

14. A pharmaceutical composition comprising the complex of claim 7 and a pharmaceutically acceptable carrier.

15. The pharmaceutical composition of claim 14, wherein the pharmaceutically acceptable carrier is a sugar or a protein.

16. The pharmaceutical composition of claim 15, wherein the sugar is selected from the group consisting of sucrose, glucose, mannitol, and a combination thereof, and is present in the pharmaceutical composition at a concentration from 5% to 20%.

17. A method of preparing a nanoparticle, comprising:
   a) combining a composition comprising the peptide of claim 1 with a composition comprising a cargo molecule to form a mixture; and
   b) incubating the mixture to form the nanoparticle.

18. A method of delivering a molecule into a cell comprising contacting the cell with the nanoparticle of claim 10, wherein the nanoparticle comprises the molecule.

19. The method of claim 18, wherein the contacting of the cell with the nanoparticle is carried out in vivo.

20. The method of claim 18, wherein the contacting of the cell with the nanoparticle is carried out ex vivo or in vitro.

21. The method of claim 18, wherein the cell is a granulocyte, a mast cell, a monocyte, a dendritic cell, a B cell, a T cell, or a natural killer cell.

22. The method of claim 21, wherein the molecule is a plasmid encoding a chimeric antigen receptor comprising an extracellular antigen-binding domain that specifically binds to a target antigen, a transmembrane domain, and an intracellular signaling domain.

23. The method of claim 22, wherein the nanoparticle further comprises a siRNA.

24. The method of claim 23, wherein the siRNA specifically targets an RNA molecule encoding PD-1, PD-L1, PD-L2, TIM-3, BTLA, VISTA, LAG-3, or CTLA-4.

25. A method of stabilizing a nucleic acid comprising:
   a) combining a composition comprising the peptide of claim 1 with a composition comprising the nucleic acid to form a mixture; and
   b) incubating the mixture to form a complex comprising the nucleic acid.

* * * * *